United States Patent
Ferguson, Jr. et al.

(10) Patent No.: US 11,284,801 B2
(45) Date of Patent: *Mar. 29, 2022

(54) QUANTIFICATION AND ANALYSIS OF ANGIOGRAPHY AND PERFUSION

(71) Applicant: Stryker European Operations Limited, Carrigtwohill (IE)

(72) Inventors: T. Bruce Ferguson, Jr., Raleigh, NC (US); Cheng Chen, Greenville, NC (US)

(73) Assignee: Stryker European Operations Limited, Carrigtwohill (IE)

( * ) Notice: Subject to any disclaimer, the term of this patent is extended or adjusted under 35 U.S.C. 154(b) by 93 days.

This patent is subject to a terminal disclaimer.

(21) Appl. No.: 16/356,766

(22) Filed: Mar. 18, 2019

(65) Prior Publication Data

US 2019/0374106 A1    Dec. 12, 2019

Related U.S. Application Data

(63) Continuation of application No. 13/922,996, filed on Jun. 20, 2013, now Pat. No. 10,278,585.

(Continued)

(51) Int. Cl.
*A61B 5/00*    (2006.01)
*A61K 49/00*    (2006.01)
(Continued)

(52) U.S. Cl.
CPC .......... *A61B 5/0071* (2013.01); *A61B 5/0261* (2013.01); *A61B 5/0275* (2013.01);
(Continued)

(58) Field of Classification Search
CPC ... A61B 5/0071; A61B 5/0275; A61B 5/0261; A61B 5/7246; G06T 7/0016
See application file for complete search history.

(56) References Cited

U.S. PATENT DOCUMENTS

| 4,109,647 A | 8/1978 | Stern et al. |
| 4,162,405 A | 7/1979 | Chance et al. |

(Continued)

FOREIGN PATENT DOCUMENTS

| AT | 409451 B | 8/2002 |
| CA | 2212257 A1 | 8/1996 |

(Continued)

OTHER PUBLICATIONS

Akintunde, A. et al. (Oct.-Nov. 1992). "Quadruple Labeling of Brain-Stem Neurons: A Multiple Retrograde Fluorescent Tracer Study of Axonal Collateralization," Journal of Neuroscience Methods 45(1-2):15-22.

(Continued)

*Primary Examiner* — James M Kish
(74) *Attorney, Agent, or Firm* — Morrison & Foerster LLP

(57) ABSTRACT

A method to visualize, display, analyze and quantify angiography, perfusion, and the change in angiography and perfusion in real time, is provided. This method captures image data sequences from indocyanine green near infra-red fluorescence imaging used in a variety of surgical procedure applications, where angiography and perfusion are critical for intraoperative decisions.

16 Claims, 25 Drawing Sheets
(22 of 25 Drawing Sheet(s) Filed in Color)

Related U.S. Application Data

(60) Provisional application No. 61/662,885, filed on Jun. 21, 2012.

(51) Int. Cl.
*A61B 5/0275* (2006.01)
*A61B 5/026* (2006.01)
*G06T 7/00* (2017.01)

(52) U.S. Cl.
CPC ...... *A61K 49/0034* (2013.01); *A61B 2505/05* (2013.01); *A61B 2576/023* (2013.01); *G06T 7/0016* (2013.01); *G06T 2207/10064* (2013.01); *G06T 2207/30104* (2013.01)

(56) References Cited

U.S. PATENT DOCUMENTS

| | | |
|---|---|---|
| 4,200,801 A | 4/1980 | Schuresko |
| 4,263,916 A | 4/1981 | Brooks et al. |
| 4,394,199 A | 7/1983 | Barnhard, IV et al. |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |
| 4,619,249 A | 10/1986 | Landry |
| 4,718,417 A | 1/1988 | Kittrell et al. |
| 4,719,508 A | 1/1988 | Sasaki et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,805,597 A | 2/1989 | Iwakoshi |
| 4,815,848 A | 3/1989 | Hadeishi |
| 4,821,117 A | 4/1989 | Sekiguchi |
| 4,827,908 A | 5/1989 | Matsuo |
| 4,852,579 A | 8/1989 | Gilstad et al. |
| 4,858,001 A | 8/1989 | Milbank et al. |
| 4,860,731 A | 8/1989 | Matsuura |
| 4,867,137 A | 9/1989 | Takahashi |
| 4,868,647 A | 9/1989 | Uehara et al. |
| 4,900,934 A | 2/1990 | Peeters et al. |
| 4,930,516 A | 6/1990 | Alfano et al. |
| 4,938,205 A | 6/1990 | Nudelman |
| 4,957,114 A | 9/1990 | Zeng et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,003,977 A | 4/1991 | Suzuki et al. |
| 5,042,494 A | 8/1991 | Alfano |
| 5,071,417 A | 12/1991 | Sinofsky |
| 5,078,150 A | 1/1992 | Hara et al. |
| 5,090,400 A | 2/1992 | Saito |
| 5,091,652 A | 2/1992 | Mathies et al. |
| 5,115,137 A | 5/1992 | Andersson-Engels et al. |
| 5,117,466 A | 5/1992 | Buican et al. |
| 5,125,404 A | 6/1992 | Kittrell et al. |
| 5,131,398 A | 7/1992 | Alfano et al. |
| 5,134,662 A | 7/1992 | Bacus et al. |
| 5,150,292 A | 9/1992 | Hoffmann et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,214,503 A | 5/1993 | Chiu et al. |
| 5,225,883 A | 7/1993 | Carter et al. |
| 5,255,087 A | 10/1993 | Nakamura et al. |
| 5,279,298 A | 1/1994 | Flower |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A | 2/1995 | Flower |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Häfele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,491,343 A | 2/1996 | Brooker |
| 5,496,369 A | 3/1996 | Howard, III |
| 5,507,287 A | 4/1996 | Palcic et al. |
| 5,514,127 A | 5/1996 | Shanks |
| 5,519,534 A | 5/1996 | Smith et al. |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Iijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A | 4/1998 | Hemstreet, III et al. |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,178,340 B1 | 1/2001 | Svetliza |
| 6,179,421 B1 | 1/2001 | Pang |
| 6,186,628 B1 | 2/2001 | Van de Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,217,848 B1 | 4/2001 | Achilefu et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imaizumi et al. |

(56) References Cited

U.S. PATENT DOCUMENTS

| | | |
|---|---|---|
| 6,319,273 B1 | 11/2001 | Chen et al. |
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Thorn Leeson et al. |
| 6,566,641 B1 | 5/2003 | Suda |
| 6,577,884 B1 | 6/2003 | Boas |
| 6,603,552 B1 | 8/2003 | Cline et al. |
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,815,170 B1 | 11/2004 | Morton |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |
| 6,915,154 B1 | 7/2005 | Docherty et al. |
| 6,936,043 B2 | 8/2005 | Peyman |
| 6,944,493 B2 | 9/2005 | Alam et al. |
| 7,113,817 B1 | 9/2006 | Winchester, Jr. et al. |
| 7,236,815 B2 | 6/2007 | Richards-Kortum et al. |
| 7,317,554 B2 | 1/2008 | Ueda et al. |
| 7,364,574 B2 | 4/2008 | Flower |
| 7,381,400 B2 | 6/2008 | Woltering |
| 7,400,753 B2 | 7/2008 | Seino et al. |
| 7,400,755 B2 | 7/2008 | West et al. |
| 7,474,906 B2 | 1/2009 | Rubinstein et al. |
| 7,482,318 B2 | 1/2009 | Aurelian et al. |
| 7,515,953 B2 | 4/2009 | Madar et al. |
| 7,581,191 B2 | 8/2009 | Rice et al. |
| 7,729,750 B2 | 6/2010 | Tromberg et al. |
| 7,774,048 B2 | 8/2010 | Nakaoka et al. |
| 7,881,777 B2 | 2/2011 | Docherty et al. |
| 7,885,438 B2 | 2/2011 | Uppaluri et al. |
| 8,036,437 B2 | 10/2011 | Arditi et al. |
| 8,073,224 B2 | 12/2011 | Strobel et al. |
| 8,144,958 B2 | 3/2012 | Nahm et al. |
| 8,185,176 B2 | 5/2012 | Mangat et al. |
| 8,194,981 B2 | 6/2012 | Suzuki |
| 8,204,579 B2 | 6/2012 | Nielsen et al. |
| 8,285,353 B2 | 10/2012 | Choi et al. |
| 8,361,775 B2 | 1/2013 | Flower |
| 8,406,860 B2 | 3/2013 | Dvorsky et al. |
| 8,480,579 B2 | 7/2013 | Serov et al. |
| 8,521,260 B2 | 8/2013 | Grinvald et al. |
| 8,538,107 B2 | 9/2013 | Röttger |
| 8,647,605 B2 | 2/2014 | Mangat et al. |
| 8,718,747 B2 | 5/2014 | Bjornerud et al. |
| 8,725,225 B2 | 5/2014 | Golijanin et al. |
| 8,892,190 B2 | 11/2014 | Docherty et al. |
| 8,929,974 B2 | 1/2015 | Hauger et al. |
| 8,965,488 B2 | 2/2015 | Dvorsky et al. |
| 9,089,601 B2 | 7/2015 | Golijanin et al. |
| 9,129,366 B2 | 9/2015 | Nahm et al. |
| 9,241,636 B2 | 1/2016 | Koizumi et al. |
| RE45,916 E | 3/2016 | Golijanin et al. |
| 9,351,644 B2 | 5/2016 | Nahm et al. |
| 9,357,931 B2 | 6/2016 | Nahm et al. |
| 9,421,280 B2 | 8/2016 | Mangat et al. |
| 9,451,903 B2 | 9/2016 | Feinberg |
| 9,554,738 B1 | 1/2017 | Gulati et al. |
| 9,610,021 B2 | 4/2017 | Dvorsky et al. |
| 9,642,532 B2 | 5/2017 | Fengler et al. |
| 9,750,441 B2 | 9/2017 | Stamatas et al. |
| 9,816,930 B2 | 11/2017 | Moriyama et al. |
| 9,913,602 B2 | 3/2018 | Weinstein et al. |
| 9,936,887 B2 | 4/2018 | Dvorsky et al. |
| 10,041,042 B2 | 8/2018 | Flower |
| 10,219,742 B2 | 3/2019 | Dvorsky et al. |
| 10,231,624 B2 | 3/2019 | Mangat et al. |
| 10,265,419 B2 | 4/2019 | Golijanin |
| 10,278,585 B2 | 5/2019 | Ferguson, Jr. et al. |
| 10,285,603 B2 | 5/2019 | Flower |
| 10,488,340 B2 | 11/2019 | Moriyama et al. |
| 10,631,746 B2 | 4/2020 | Flower et al. |
| 2002/0007123 A1 | 1/2002 | Balas |
| 2002/0025541 A1 | 2/2002 | Nelson et al. |
| 2002/0038120 A1 | 3/2002 | Duhaylongsod et al. |
| 2002/0049389 A1 | 4/2002 | Abreu |
| 2002/0099279 A1 | 7/2002 | Pfeiffer et al. |
| 2002/0099295 A1 | 7/2002 | Gil et al. |
| 2002/0146369 A1 | 10/2002 | Goldenberg |
| 2002/0181752 A1 | 12/2002 | Wallo et al. |
| 2002/0183621 A1 | 12/2002 | Pfeiffer et al. |
| 2003/0032885 A1 | 2/2003 | Rubinstein et al. |
| 2003/0050543 A1 | 3/2003 | Hartmann |
| 2003/0050678 A1 | 3/2003 | Sierra et al. |
| 2003/0054015 A1 | 3/2003 | Haze et al. |
| 2003/0060718 A1 | 3/2003 | Alam et al. |
| 2003/0060722 A1 | 3/2003 | Pfeiffer et al. |
| 2003/0064025 A1 | 4/2003 | Yang et al. |
| 2003/0093064 A1 | 5/2003 | Peyman |
| 2003/0093065 A1 | 5/2003 | Peyman |
| 2003/0127609 A1 | 7/2003 | El-Hage et al. |
| 2003/0139667 A1 | 7/2003 | Hewko et al. |
| 2003/0156252 A1 | 8/2003 | Morris et al. |
| 2003/0187349 A1 | 10/2003 | Kaneko et al. |
| 2003/0191368 A1 | 10/2003 | Wang et al. |
| 2003/0232016 A1 | 12/2003 | Heinrich |
| 2003/0236458 A1 | 12/2003 | Hochman |
| 2004/0002660 A1 | 1/2004 | Mielekamp |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1 | 9/2004 | Levine |
| 2005/0019744 A1 | 1/2005 | Bertuglia |
| 2005/0020891 A1 | 1/2005 | Rubinstein et al. |
| 2005/0033145 A1 | 2/2005 | Graham et al. |
| 2005/0038471 A1 | 2/2005 | Chan |
| 2005/0065432 A1 | 3/2005 | Kimura |
| 2005/0069525 A1 | 3/2005 | Mikael |
| 2005/0089866 A1 | 4/2005 | Hinuma et al. |
| 2005/0107380 A1 | 5/2005 | Nimmo et al. |
| 2005/0142556 A1 | 6/2005 | Hoon et al. |
| 2005/0182321 A1 | 8/2005 | Frangioni |
| 2005/0182327 A1 | 8/2005 | Petty et al. |
| 2005/0182431 A1 | 8/2005 | Hausen et al. |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0254008 A1 | 11/2005 | Ferguson et al. |
| 2006/0011853 A1 | 1/2006 | Spartiotis et al. |
| 2006/0013768 A1 | 1/2006 | Woltering |
| 2006/0079750 A1 | 4/2006 | Fauci et al. |
| 2006/0108509 A1 | 5/2006 | Frangioni et al. |
| 2006/0118742 A1 | 6/2006 | Levenson et al. |
| 2006/0147897 A1 | 7/2006 | Grinvald et al. |
| 2006/0239921 A1 | 10/2006 | Mangat et al. |
| 2006/0241499 A1 | 10/2006 | Irion et al. |
| 2007/0121099 A1 | 5/2007 | Matsumoto et al. |
| 2007/0122344 A1 | 5/2007 | Golijanin |
| 2007/0122345 A1 | 5/2007 | Golijanin |
| 2007/0203413 A1 | 8/2007 | Frangioni |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0025918 A1 | 1/2008 | Frangioni et al. |
| 2008/0044073 A1 | 2/2008 | Bernhardt et al. |
| 2008/0064925 A1 | 3/2008 | Gill et al. |

(56) References Cited

U.S. PATENT DOCUMENTS

| | | |
|---|---|---|
| 2008/0071176 A1* | 3/2008 | Docherty ............ A61B 5/0071 600/476 |
| 2008/0081990 A1 | 4/2008 | Berenfeld et al. |
| 2008/0124806 A1 | 5/2008 | Noda et al. |
| 2008/0161744 A1 | 7/2008 | Golijanin et al. |
| 2008/0188728 A1 | 8/2008 | Neumann et al. |
| 2008/0194970 A1 | 8/2008 | Steers et al. |
| 2008/0221421 A1 | 9/2008 | Choi et al. |
| 2008/0221648 A1 | 9/2008 | Flower |
| 2008/0239070 A1 | 10/2008 | Westwick et al. |
| 2008/0241841 A1 | 10/2008 | Murakawa et al. |
| 2008/0319309 A1* | 12/2008 | Bredno ............ G01R 33/5601 600/420 |
| 2009/0005693 A1 | 1/2009 | Brauner et al. |
| 2009/0042179 A1 | 2/2009 | Peltie et al. |
| 2009/0048516 A1 | 2/2009 | Yoshikawa et al. |
| 2009/0054788 A1 | 2/2009 | Hauger et al. |
| 2009/0068132 A1 | 3/2009 | Bratescu et al. |
| 2009/0112097 A1 | 4/2009 | Kato et al. |
| 2009/0118623 A1 | 5/2009 | Serov et al. |
| 2009/0137902 A1 | 5/2009 | Frangioni et al. |
| 2009/0252682 A1 | 10/2009 | Hillman |
| 2009/0297004 A1* | 12/2009 | Baumgart ............ G16H 30/20 382/130 |
| 2010/0007727 A1 | 1/2010 | Torre-Bueno |
| 2010/0016669 A1 | 1/2010 | Takaoka et al. |
| 2010/0022898 A1 | 1/2010 | Rubinstein et al. |
| 2010/0036217 A1 | 2/2010 | Choi et al. |
| 2010/0041999 A1 | 2/2010 | Schuhrke et al. |
| 2010/0061604 A1 | 3/2010 | Nahm et al. |
| 2010/0069759 A1 | 3/2010 | Schuhrke et al. |
| 2010/0080757 A1 | 4/2010 | Haaga et al. |
| 2010/0099961 A1 | 4/2010 | Hubner et al. |
| 2010/0222673 A1 | 9/2010 | Mangat et al. |
| 2010/0286529 A1 | 11/2010 | Carroll et al. |
| 2011/0001061 A1 | 1/2011 | Ishihara |
| 2011/0013002 A1 | 1/2011 | Thompson et al. |
| 2011/0063427 A1 | 3/2011 | Fengler et al. |
| 2011/0071403 A1 | 3/2011 | Sevick-Muraca et al. |
| 2011/0098685 A1 | 4/2011 | Flower |
| 2011/0306877 A1 | 12/2011 | Dvorsky et al. |
| 2011/0309275 A1 | 12/2011 | Azimi et al. |
| 2012/0026325 A1 | 2/2012 | Bunker et al. |
| 2012/0078093 A1 | 3/2012 | Flower |
| 2012/0252699 A1 | 4/2012 | Jaffrey et al. |
| 2012/0165627 A1 | 6/2012 | Yamamoto |
| 2012/0165662 A1 | 6/2012 | Nahm et al. |
| 2012/0271176 A1 | 10/2012 | Moghaddam et al. |
| 2012/0323118 A1 | 12/2012 | Gopalakrishna et al. |
| 2013/0035569 A1 | 2/2013 | Heanue et al. |
| 2013/0203082 A1 | 8/2013 | Gonda et al. |
| 2013/0203083 A1 | 8/2013 | Connors et al. |
| 2013/0230866 A1 | 9/2013 | Miyashita et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0342674 A1 | 12/2013 | Dixon |
| 2013/0345560 A1 | 12/2013 | Ferguson, Jr. et al. |
| 2014/0099007 A1 | 4/2014 | Sarkar et al. |
| 2014/0254909 A1 | 9/2014 | Carmi et al. |
| 2014/0308656 A1 | 10/2014 | Flower |
| 2014/0316262 A1 | 10/2014 | Havens |
| 2014/0371583 A1 | 12/2014 | Flower |
| 2015/0112192 A1 | 4/2015 | Docherty et al. |
| 2015/0112193 A1 | 4/2015 | Docherty et al. |
| 2015/0164396 A1 | 6/2015 | Acharya et al. |
| 2015/0182137 A1 | 7/2015 | Flower et al. |
| 2015/0196208 A1 | 7/2015 | Dvorsky et al. |
| 2015/0230710 A1 | 8/2015 | Nahm et al. |
| 2015/0230715 A1 | 8/2015 | Nahm et al. |
| 2015/0248758 A1 | 9/2015 | Pautot |
| 2015/0381909 A1 | 12/2015 | Butte et al. |
| 2016/0038027 A1 | 2/2016 | Brzozowski et al. |
| 2016/0041098 A1 | 2/2016 | Hirawake et al. |
| 2016/0097716 A1 | 4/2016 | Gulati et al. |
| 2016/0199515 A1 | 7/2016 | Flower |
| 2016/0253800 A1 | 9/2016 | Gurevich et al. |
| 2016/0371834 A1 | 12/2016 | Watanabe et al. |
| 2017/0039710 A1 | 2/2017 | Minai et al. |
| 2017/0084024 A1 | 3/2017 | Gurevich |
| 2017/0245766 A1 | 8/2017 | Flower et al. |
| 2017/0303800 A1 | 10/2017 | Flower et al. |
| 2018/0020933 A1 | 1/2018 | Dvorsky et al. |
| 2018/0104362 A1 | 4/2018 | Golijanin et al. |
| 2018/0120230 A1 | 5/2018 | Moriyama et al. |
| 2018/0220907 A1 | 8/2018 | Dvorsky et al. |
| 2018/0234603 A1 | 8/2018 | Moore et al. |
| 2018/0369426 A1 | 12/2018 | Flower et al. |
| 2019/0388565 A1 | 12/2019 | Golijanin |
| 2020/0323439 A1 | 10/2020 | Flower et al. |
| 2021/0169354 A1 | 6/2021 | Dvorsky et al. |

FOREIGN PATENT DOCUMENTS

| | | |
|---|---|---|
| CA | 2413033 A1 | 3/2000 |
| CA | 2711560 A1 | 7/2009 |
| CA | 2913692 A1 | 1/2015 |
| CN | 1049781 A | 3/1991 |
| CN | 1200174 A | 11/1998 |
| CN | 1399528 A | 2/2003 |
| CN | 1406131 A | 3/2003 |
| CN | 1547617 A | 11/2004 |
| CN | 1636506 A | 7/2005 |
| CN | 1678239 A | 10/2005 |
| CN | 101264014 A | 9/2008 |
| CN | 101275164 A | 10/2008 |
| CN | 101451953 A | 6/2009 |
| CN | 101484067 A | 7/2009 |
| CN | 101854903 A | 10/2010 |
| CN | 101936982 A | 1/2011 |
| CN | 102026668 A | 4/2011 |
| CN | 102076911 A | 5/2011 |
| CN | 102288589 A | 12/2011 |
| CN | 102405212 A | 4/2012 |
| CN | 102436648 A | 5/2012 |
| CN | 103519825 A | 1/2014 |
| CN | 103608662 A | 2/2014 |
| CN | 105658138 A | 6/2016 |
| DE | 3906860 A1 | 9/1989 |
| DE | 19608027 A1 | 9/1996 |
| DE | 10028233 A1 | 1/2002 |
| DE | 10120980 A1 | 11/2002 |
| DE | 69727220 T2 | 12/2004 |
| DE | 102005044531 A1 | 3/2007 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0807402 A1 | 11/1997 |
| EP | 0826335 A1 | 3/1998 |
| EP | 1677097 A1 | 7/2006 |
| EP | 1761171 | 3/2007 |
| EP | 1874181 | 1/2008 |
| EP | 3 007 618 A2 | 4/2016 |
| FR | 2944104 A1 | 10/2010 |
| GB | 2203831 A | 10/1988 |
| JP | S52-34584 A | 3/1977 |
| JP | S58-222331 A | 12/1983 |
| JP | S59-069721 A | 4/1984 |
| JP | S59-070903 A | 4/1984 |
| JP | H01-236879 A | 9/1989 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | H07-043303 A | 2/1995 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |

(56) References Cited

FOREIGN PATENT DOCUMENTS

| | | |
|---|---|---|
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | H09-308609 A | 12/1997 |
| JP | H09-309845 A | 12/1997 |
| JP | H10-500479 A | 1/1998 |
| JP | H10-503480 A | 3/1998 |
| JP | H10-085222 A | 4/1998 |
| JP | H10-104070 A | 4/1998 |
| JP | H10-151104 A | 6/1998 |
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2001-198079 A | 7/2001 |
| JP | 2002-219129 A | 8/2002 |
| JP | 2003-510121 A | 3/2003 |
| JP | 2003-144401 A | 5/2003 |
| JP | 2003-187226 A | 7/2003 |
| JP | 2003-329589 A | 11/2003 |
| JP | 2004-528917 A | 9/2004 |
| JP | 2004-325200 A | 11/2004 |
| JP | 2006-503620 A | 2/2006 |
| JP | 2006-192280 A | 7/2006 |
| JP | 2007-021006 A | 2/2007 |
| JP | 3896176 B2 | 3/2007 |
| JP | 2008-023113 A | 2/2008 |
| JP | 2008-525126 A | 7/2008 |
| JP | 2008-220926 A | 9/2008 |
| JP | 2008-535600 A | 9/2008 |
| JP | 2008-231113 A | 10/2008 |
| JP | 2009-095683 A | 5/2009 |
| JP | 2009-519082 A | 5/2009 |
| JP | 2009-291554 A | 12/2009 |
| JP | 2010-505582 A | 2/2010 |
| JP | 2010-521267 A | 6/2010 |
| JP | 2011-19829 A | 2/2011 |
| JP | 2011-509768 A | 3/2011 |
| JP | 2011-519589 A | 7/2011 |
| JP | 2011-528918 A | 12/2011 |
| JP | 5918532 B2 | 5/2016 |
| JP | 2016-521612 A | 7/2016 |
| KR | 90-0005434 B1 | 7/1990 |
| KR | 2002-0064287 A | 8/2002 |
| RU | 2288633 C1 | 12/2006 |
| WO | WO-1986/02730 A1 | 5/1986 |
| WO | WO-1990/10219 A1 | 9/1990 |
| WO | WO-1990/12536 A1 | 11/1990 |
| WO | WO-1993/25141 A1 | 12/1993 |
| WO | WO-1994/12092 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | WO-2001/08552 A1 | 2/2001 |
| WO | WO-2001/17561 A1 | 3/2001 |
| WO | WO-2001/22870 A1 | 4/2001 |
| WO | WO-2001/39764 A2 | 6/2001 |
| WO | WO-2001/69244 A2 | 9/2001 |
| WO | WO-2001/80734 A1 | 11/2001 |
| WO | WO-2001/82786 A2 | 11/2001 |
| WO | WO-2002/061390 A2 | 8/2002 |
| WO | WO-03/000928 A2 | 1/2003 |
| WO | WO-2003/006658 A1 | 1/2003 |
| WO | WO-2004/006963 A1 | 1/2004 |
| WO | WO-2004/052195 A1 | 6/2004 |
| WO | WO-2005/026319 A2 | 3/2005 |
| WO | WO-2005/034747 A1 | 4/2005 |
| WO | WO-2005/036143 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/012301 A1 | 2/2007 |
| WO | WO-2007/028032 A2 | 3/2007 |
| WO | WO-2008/039968 A2 | 4/2008 |
| WO | WO-2008/044822 A1 | 4/2008 |
| WO | WO-2008/070269 A2 | 6/2008 |
| WO | WO-2008/070269 A3 | 6/2008 |
| WO | WO-2008/087869 A1 | 7/2008 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2009/154898 A1 | 12/2009 |
| WO | WO-2012/038824 A1 | 3/2012 |
| WO | WO 2012/096878 * | 7/2012 ............... A61B 5/00 |
| WO | WO-2012/096878 A2 | 7/2012 |
| WO | WO-2015/001427 A2 | 1/2015 |
| WO | WO-2013/002350 A1 | 2/2015 |

OTHER PUBLICATIONS

Alander, J.T. et al. (Jan. 1, 2012). "A Review of Indocyanine Green Fluorescent Imaging in Surgery," International Journal of Biomedical Imaging 2012:1-26, article ID 940585.

Alfano et al. (Oct. 1987). "Fluorescence Spectra from Cancerous and Normal Human Dreast and Lung Tissues," IEEE Journal of Quantum Electronics QE-23(10):1806-1811.

Alm, A. et al. (Jan. 1, 1973). "Ocular and Optic Nerve Blood Flow at Normal and Increased Intraocular Pressures in Monkeys (*Macaca irus*): A Study with Radioactively Labelled Microspheres Including Flow Determinations in Brain and Some Other Tissues," Experimental Eye Research 15(1):15-29.

Alonso-Burgos, A. et al.(2006). "Preoperative planning of deep inferior epigastric artery perforator flap reconstruction with multi-slice-CT angiography: imaging findings and initial experience," Journal of Plastic, Reconstructive & Aesthetic Surgery 59:585-593.

Alvarez, F. J. et al. (Apr. 1996). "Behaviour of Isolated Rat and Human Red Blood Cells Upon Hypotonic-Dialysis Encapsulation of Carbonic Anhydrase and Dextran," Biotechnology and Applied Biochemistry 23(2): 173-179.

Ancalmo, N. et al. (1997). "Minimally invasive coronary artery bypass surgery: really minimal?" Ann. Thorac. Surg. 64:928-929.

Andersson-Engels, S. et al. (1991). "Fluorescence Characteristics of Atherosclorotic Plaque and Malignant Tumors," in Optical Methods for Tumor Treatment and Early Diagnosis Mechanisms and Techniques, T. J. Dougherty (Ed.), The Society of Photo-optical Instrumentation Engineers (SPIE) 1426:31-43, fourteen pages.

Andersson-Engels, S. et al. (Mar. 1989). "Tissue Diagnostics Using Laser-Induced Fluorescence," Berichte der Bunsengesellschaft für physikalische Chemie 93(3):335-342.

(56) References Cited

OTHER PUBLICATIONS

Angelov, D.N. et al. (Apr. 1999). "Contralateral Trigeminal Nerve Lesion Reduces Polyneuronal Muscle Innervation after Facial Nerve Repair in Rats," European Journal of Neuroscience 11 (4):1369-1378.
Annese, V. et al. (2005). "Erthrocytes-Mediated Delivery of Dexamethasone in Steroid-Dependent IBD Patients-a Pilot Uncontrolled Study," American Journal of Gastroenterology 100:1370-1375.
Argus-50/CA, Intercellular CA2+ (calcium ion) Image Analysis system (Feb. 1992). "Observation and 2-dimensional analysis of Ca2+ concentration distribution. Fura-2 and lndo-1 compatible. Ca2+ concentrations are calculated from the fluorescence ratio," pp. 1-10.
Australian Notice of Allowance dated Sep. 17, 2018 for Australian Patent Application No. 2015327665, filed on Mar. 23, 2017, three pages.
Australian Notice of Allowance dated Jul. 3, 2019 for Australian Patent Application No. 2014408488, filed on Mar. 31, 2017, three pages.
Australian Office Action dated Jun. 26, 2018 for Australian Patent Application No. 2014408488, filed on Mar. 31, 2017, nine pages.
Author Unknown. (Jun. 4, 2008)."Invitrogen," Material Safety Data Sheet, p. 1-4.
Awano, T. et al. (Jun. 2010). "Intraoperative EC-IC Bypass Blood Flow Assessment with Indocyanine Green Angiography in Moyamoya and Non-moyamoya Ischemic Stroke," World Neurosurg. 73(6):668-674.
Azuma, R. et al. (2008, presented in part Jun. 2007). "Detection of Skin Perforators by Indocyanine Green Fluorescence Nearly Infrared Angiography," PRS Journal 122(4):1062-1067.
Balacumarswami, L. et al. (Aug. 2004). "Does Off-Pump Total Arterial Grafting Increase the Incidence of Intraoperative Graft Failure?," The Journal of Thoracic and Cardiovascular Surgery 128(2):238-244.
Barton, J.K. et al. (1999) "Simultaneous irradiation and imaging of blood vessels during pulsed laser delivery," Lasers in Surgery and Medicine 24(3):236-243.
Bassingthwaighte, J.B. et al. (Apr. 1974). "Organ Blood Flow, Wash-in, Washout, and Clearance of Nutrients and Metabolites," Mayo Clin. Proc. 49(4):248-255.
Batliwala, H. et al. (Apr. 15, 1995). "Methane-Induced Haemolysis of Human Erythrocytes," Biochemical J. 307(2):433-438.
Baumgartner, R. et al. (1987). "Section V—In vivo Localization and Photodynamic Therapy: A Fluorescence Imaging Device for Endoscopic Detection of Early Stage Cancer—Instrumental and Experimental Studies", Photochemistry and Photobiology 46(5):759-763.
Baumgartner, R. et al. (Jan. 1, 1990). "A Fluorescence Imaging Device for Endoscopic Detection of Early Stage Cancer Instrumental and Experimental Studies," Section Five in SPIE. Press, ed. Abraham Katzir, pp. 513-517, eight pages. Reprinted by Permission By SPIE. Press from Photochemistry and Photobiology 46(5):759-763, (1987).
Bek, T. (1999). "Diabetic Maculopathy Caused by Disturbances in Retinal Vasomotion: A New Hypothesis," Acta Ophthalmologica Scandinavica 77:376-380.
Benson, R.C. et al. (1978). "Fluorescence Properties of Indocyanine Green as Related to Angiography," Phys. Med. Biol. 23(1):159-163.
Black's Medical Dictionary, "Perfusion," 42nd Edition (2009), two pages.
Boer, F. et al. (1994). "Effect of Ventilation on First-Pass Pulmonary Retention of Alfentaril and Sufentanil in Patients Undergoing Coronary Artery Surgery," British Journal Anesthesia 73:458-463.
Boldt, .J. et al. (Feb. 1990). "Lung management during cardiopulmonary bypass influence on extravascular lung water," Journal of Cardiothoracic Anesthesia 4(1):73-79.
Boldt, J. et al. (1991). "Does the technique of cardiopulmonary bypass affect lung water content?" European Journal of Cardio-Thoracic Surgery 5:22-26.
Brazilian Office Action dated May 14, 2019 for Brazilian Application No. PI 0907272-1, filed on Oct. 14, 2010, five pages.
Bütter, A. et al. (May 2005). "Melanoma in Children and the Use of Sentinel Lymph Node Biopsy," Journal of Pediatric Surgery 40(5):797-800.
C2741, Compact High Performance video camera for industrial applications with Built-in contrast enhancement circuit, Jun. 1998, six pages.
Canada Health. (1997). "Coronary Bypass Surgery and Angioplasty, 1982-1995, Heart Disease and Stroke in Canada," Canada Health, located at <http://www.hc-sc.gc.ca/hpb>, eighty two pages.
Canadian Notice of Allowance dated Jan. 4, 2018 for Canadian Application No. 2,750,760, filed on Jul. 25, 2008, one page.
Canadian Notice of Allowance dated Sep. 27, 2017 for Canadian Application No. 2,811,847, filed on Mar. 20, 2013, one page.
Canadian Office Action dated Dec. 12, 2018 for CA Application No. 2,963,987 filed on Mar. 27, 2017, four pages.
Canadian Office Action dated Dec. 28, 2018 for CA Application No. 2,963,450 filed on Apr. 3, 2017, four pages.
Canadian Office Action dated Feb. 13, 2018 for CA Application No. 2,963,450 filed on Apr. 3, 2017, three pages.
Canadian Office Action dated Feb. 27, 2017 for Canadian Application No. 2,750,760, filed on Jul. 25, 2011, three pages.
Canadian Office Action dated Feb. 28, 2018 for CA Application No. 2,963,987 filed on Mar. 27, 2017, five pages.
Canadian Office Action dated Jan. 19, 2017 for Canadian Application No. 2,914,778 filed on Dec. 8, 2015, four pages.
Canadian Office Action dated Mar. 16, 2016 for CA Application No. 2,750,760 filed on Jan. 23, 2009, five pages.
Canadian Office Action dated May 28, 2019 for Canadian Application No. 3,011,310, filed on Jul. 11, 2018, four pages.
Canadian Office Action dated Nov. 28, 2017 for Canadian Application No. 2,914,778 filed on Dec. 8, 2015, six pages.
Canadian Office Action dated Nov. 28, 2018 for CA Application No. 2,750,760 filed on Jan. 23, 2009, three pages.
Canadian Office Action dated Oct. 25, 2016 for Canadian Patent Application No. 2,811,847, filed on Sep. 20, 2011, three pages.
Canadian Office Action dated Sep. 30, 2015 for CA Application No. 2,811,847, filed on Sep. 20, 2011, four pages.
Chinese Office Action dated Jul. 3, 2012, issued in counterpart Chinese Application No. 200980123414.0, eight pages.
Chinese Office Action dated Apr. 6, 2017 for Chinese Application No. 201510214021.8, filed on May 14, 2009, fifteen pages.
Chinese Office Action dated Apr. 17, 2019 for Chinese Application No. 201510214021.8, filed on May 14, 2009, sixteen pages.
Chinese Office Action dated Apr. 26, 2019 for CN Application No. 201580064648.8 filed on May 26, 2017, twenty six pages.
Chinese Office Action dated Aug. 8, 2016 for Chinese Application No. 201180057244.8 filed on Sep. 20, 2011, eighteen pages.
Chinese Office Action dated Dec. 19, 2017 for Chinese Application No. 201180057244.8 filed on Sep. 20, 2011, eleven pages.
Chinese Office Action dated Feb. 8, 2018 for Chinese Application No. 201510214021.8, filed on May 14, 2009, seventeen pages.
Chinese Office Action dated Mar. 13, 2017 for Chinese Application No. 201180057244.8 filed on Sep. 20, 2011, twenty pages.
Chinese Office Action dated May 23, 2013, issued in counterpart Chinese Application No. 200980123414.0, nineteen pages.
Chinese Office Action dated Nov. 12, 2015 for Chinese Patent Application No. 201180057244.8, filed on Sep. 20, 2010, five pages, (English Translation).
Chinese Office Action dated Sep. 27, 2018 for Chinese Application No. 201510214021.8, filed on May 14, 2009, seventeen pages.
Coffey, J.H. et al. (1984). "Evaluation of Visual Acuity During Laser Photoradiation Therapy of Cancer," Lasers in Surgery and Medicine 4(1):65-71.
Conley, M.P. et al. (Oct. 2004). "Anterograde Transport of Peptide-Conjugated Fluorescent Beads in the Squid Giant Axom Identifies a Zip-Code for Synapse," Biological Bulletin 207(2):164, one page.
Costa, R.A. et al. (Oct. 2001). "Photodynamic Therapy with Indocyanine Green for Occult Subfoveal Choroidal Neovascularization Caused by Age-Related Macular Degeneration," Curr. Eye Res. 23(4):274-275.

(56) References Cited

OTHER PUBLICATIONS

Cothren, R.M. et al. (Mar. 1990). "Gastrointestinal Tissue Diagnosis by Laser-Induced Fluorescence Spectroscopy at Endoscopy," Gastrointestinal Endoscopy 36(2):105-111.
Dail, W.G. et al. (Oct. 1999). "Multiple Vasodilator Pathways from the Pelvic Plexus to the Penis of the Rat," International Journal of Impotence Research 11(5):277-285.
Dan, A.G. et al. (Nov. 2004). "1% Lymphazurin vs 10% Fluorescein for Sentinel Node Mapping in Colorectal Tumors," Arch Surg. 139(11):1180-1184.
Daniels, G. et al. (Apr. 2007). "Towards Universal Red Blood Cell," Nature Biotechnology 25(4):427-428.
De Flora, A. (Sep. 1986). "Encapsulation of Adriamycin in human erythrocytes," Proc. Natl. Acad. Sci., USA 83(18):7029-7033.
Declaration of Brian Wilson dated Aug. 22, 2017 for Inter Partes Review No. IPR2017-01426, twelve pages, [EXHIBIT 2002].
Definition of "Expose," Excerpt of Merriam Webster's Medical Desk Dictionary (1993), four pages, [EXHIBIT 2004].
Definition of "Graft," Excerpt of Stedman's Medical Dictionary for the Health Professions and Nursing; 6th Ed. (2008), three pages, [EXHIBIT 2003].
De-Grand, A.M. et al. (Dec. 2003). "An Operational Near Infrared Fluorescence Imaging System Prototype for Large Animal Surgery," Technology in Cancer Research & Treatment 2(6):1-10.
Deloach, J.R. (ed.) et al. (1985). Red Blood Cells as Carriers for Drugs. A Method for Disseminating Chemotherapeutics, Hormones, Enzymes and Other Therapeutic Agents via the Circulatory System, Karger, Basel, CH, pp. v-vii, (Table of Contents), seven pages.
Deloach, J.R. (Jun. 1983). "Encapsulation of Exogenous Agents in Erythrocytes and the Circulating Survival of Carrier Erythrocytes," Journal of Applied Biochemistry 5(3):149-157.
Demos (May/Jun. 2004). "Near-Infrared Autofluorescence Imaging for Detection of Cancer," Journal of Biomedical Optics 9(3):587-592.
Desai, N.D. et al. (Oct. 18, 2005, e-published on Sep. 28, 2005) "Improving the Quality of Coronary Bypass Surgery with Intraoperative Angiography," Journal of the American College of Cardiology 46(8):1521-1525.
Detter, C. et al. (Aug. 28, 2007). "Fluorescent Cardiac Imaging: A Novel Intraoperative Method for Quantitative Assessment of Myocardial Perfusion During Graded Coronary Artery Stenosis," Circulation 116(9):1007-1014.
Detter, C. et al. (Jun. 2002). "Near-Infrared Fluorescence Coronary Angiography: A New Noninvasive Technology for Intraoperative Graft Patency Control." The Heart Surgery Forum #2001-6973 5(4):364-369.
Dietz, F.B. et al. (Feb. 2003). "Indocyanine Green: Evidence of Neurotoxicity in Spinal Root Axons," Anesthesiology 98(2):516-520.
Digital CCD Microscopy (date unknown). Chapter 14, pp. 259-282.
Dougherty, T.J. et al. (1990). "Cutaneous Phototoxic Occurrences in Patients Receiving Photofrin," Lasers in Surgery and Medicine 10(5):485-488.
Draijer, M.J. et al. (Jun. 17-19, 2007). "Laser Doppler Perfusion Imaging with a High-Speed CMOS-Camera," in Novel Optical Instrumentation for Biomedical Applications III, C. Depeursinge, ed., Proceedings of SPIE-OSA Biomedical Optics (Optical Society of America, 2007), SPIE-OSA, 6631:0N1-0N7, eight pages.
Dünne, A. et al. (Nov. 2001)."Value of Sentinel lymphonodectomy in Head and Neck Cancer Patients without Evidence of Lymphogenic Metastatic Disease," Auris Nasus Larynx 28(4):339-344.
Ekstrand, M.I. et al. (Feb. 14, 2008). "The Alpha-Herpesviruses: Molecular Pathfinders in Nervous System Circuits," Trends in Molecular Medicine, Elsevier Current Trends 14(3):134-140.
Emery R.W. et al. (Aug. 1996). "Revascularization Using Angioplasty and Minimally Invasive Techniques Documented by Thermal Imaging," The Annals of Thoracic Surgery 62(2):591-593.
Enquist, L.W. et al. (2002). "Directional Spread of an α-Herpesvirus in the Nervous System," Veterinary Microbiology 86:5-16.
Eren, S. et al. (Dec. 1995). "Assessment of Microcirculation of an Axial Skin Flap Using Indocyanine Green Fluorescence Angiography," Plast. Reconstr. Surg. 96(7):1636-1649. [EXHIBIT 1008].
European Notice of Allowance dated Oct. 21, 2015 for EP Application No. 11 826 475.3, filed on Sep. 20, 2010, eight pages.
European Decision in Opposition Proceeding Revoking (Jun. 10, 2010). European Patent No. 1 143 852, thirty pages.
European Decision of European Patent Office Technical Board of Appeal Revoking Counterpart Patent No. 1143852, dated Oct. 23, 2013. [EXHIBIT-1009].
European Notice of Allowance dated Jul. 16, 2019 for EP Application No. 18166591.0, filed on May 1, 2009, eight pages.
European Notice of Allowance dated Apr. 21, 2017 for EP Application No. 09732993.2, filed on Nov. 8, 2010, two pages.
European Notice of Allowance dated Dec. 1, 2017 for European patent Application No. 09739980.2, filed on Nov. 30, 2010, seven pages.
European Notice of Allowance dated Mar. 15, 2018 for EP Application No. 09739980.2 filed on Nov. 30, 2010, two pages.
European Notice of Allowance dated Nov. 21, 2017 for European Patent Application No. 15160177.0, filed on Aug. 11, 2000, seven pages.
European Notice of Allowance dated Oct. 29, 2015 for EP Application No. 09 704 642.9, filed on Jan. 25, 2008, two pages.
European Office Action dated Apr. 6, 2018 for EP Application No. 15188378.2 filed on Oct. 5, 2015, four pages.
European Office Action dated Aug. 31, 2017 for EP Application No. 09739980.2 filed on Nov. 30, 2010, four pages.
European Office Action dated Mar. 9, 2016 for European Patent Application No. 09739980.2 filed on May 1, 2009, five pages.
European Office Action dated Mar. 27, 2015 for EP Application No. 09 732 993.2, filed on Apr. 14, 2008, six pages.
European Office Action dated May 15, 2014 in EP Application No. 09732993.2, one page.
European Office Action dated May 27, 2016 for EP Application No. 15160177.0 filed on Aug. 11, 2000, five pages.
European Office Action dated May 28, 2018 for EP Application No. 16183434.6 filed on Aug. 9, 2016, four pages.
European Office Action dated Nov. 14, 2016 in EP Application No. 16163909.1, two pages.
European Office Action dated Sep. 21, 2017 for European Application No. 16163909.1 filed on Apr. 5, 2016, three pages.
European Opposition of European Patent No. EP1143852 lodged by Hamamatsu Photonics, Inc., Jul. 30, 2008.
European Search Report dated Apr. 28, 2014 for EP Application No. 09 732 993.2, filed on Apr. 14, 2008, eight pages.
European Search Report dated Dec. 16, 2010 for European Application No. 10186218.3 filed on Aug. 11, 2000, seven pages.
European Search Report dated Feb. 22, 2012 for EP Application No. 09 704 642.9, filed on Jan. 25, 2008, fifteen pages.
European Search Report dated Jan. 10, 2018 for EP Application No. 17171383.7 filed on May 16, 2017, eleven pages.
European Search Report dated Jan. 28, 2014 for EP Application No. 11 826 475.3, filed on Sep. 20, 2010, six pages.
European Search Report dated Jul. 6, 2004 for EP Application No. 00955472.6 filed on Aug. 11, 2000, five pages.
European Search Report dated Jul. 16, 2018 for EP Application No. 15846111.1, filed on Apr. 25, 2017, thirteen pages.
European Search Report dated Jun. 6, 2018 for EP Application No. 18166591.0 filed on Apr. 10, 2018, six pages.
European Search Report dated Jun. 11, 2014 for European Application No. 13178642.8, filed on May 1, 2009, five pages.
European Search Report dated Jun. 28, 2016 for European Application No. 16163909.1 filed on Apr. 5, 2016, six pages.
European Search Report dated May 23, 2018 for EP Application No. 14903635.2 filed on May 2, 2017, nine pages.
European Search Report dated Oct. 14, 2015 for EP Application No. 13806313.6 filed on Jun. 20, 2013, nine pages.
European Search Report dated Sep. 16, 2016 for EP Application No. 16183434.6 filed on Aug. 9, 2016, ten pages.
European Summons to attend Oral Proceedings pursuant to Rule 115(1) EPC issued on Apr. 25, 2016 for European patent application No. 09732993.2, filed on Apr. 14, 2009, 5 pages.

(56) References Cited

OTHER PUBLICATIONS

European Summons to attend Oral Proceedings pursuant to Rule 115(1) EPC mailed on Dec. 16, 2016 for European patent application No. 15160177.0, filed on Aug. 11, 2000, seven pages.
European Summons to Attend the Oral Proceedings mailed on May 31, 2019 for European Application No. 16163909.1 filed on Apr. 5, 2016, two pages.
European Summons to Attend the Oral Proceedings mailed on Oct. 24, 2018 for European Application No. 16163909.1 filed on Apr. 5, 2016, four pages.
Falk, T. et al. (Apr. 15, 2001). "A Herpes Simplex Viral Vector Expressing Green Fluorescent Protein can be Used to Visualize Morphological Changes in High-density Neuronal Culture," Electronic Journal of Biotechnology 4(1):34-45.
Flower, R. et al. (Apr.-Jun. 1999). "Effects of free and liposome-encapsulated hemoglobin on choroidal vascular plexus blood flow, using the rabbit eye as a model system," European Journal of Ophthalmology 9(2):103-114.
Flower, R.W. (1992). "Choroidal Angiography Today and Tomorrow," Retina 12(3):189-190.
Flower, R.W. (Apr. 2000). "Experimental Studies of Indocyanine Green Dye-Enhanced Photocoagulation of Choroidal Neovascularization Feeder Vessels," American Journal of Ophthalmology 129(4):501-512.
Flower, R.W. (Aug. 2002). "Optimizing Treatment of Choroidal Neovascularization Feeder Vessels Associated with Age-Related Macular Degeneration," American Journal of Ophthalmology 134(2):228-239.
Flower, R.W. (Dec. 1973). "Injection Technique for Indocyanine Green and Sodium Fluorescein Dye Angiography of the Eye," Investigative Opthamology 12(12):881-895.
Flower, R.W. (Sep. 1, 1994). "Does Preinjection Binding of Indocyanine Green to Serum Actually Improve Angiograms?", Arch Ophthalmol. 112(9):1137-1139.
Flower, R.W. et al. (Aug. 1977). "Quantification of Indicator Dye Concentration in Ocular Blood Vessels," Exp. Eye Res. 25(2):103-111.
Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," Investigative Ophthalmology, & Visual Science 49(12):5510-5516.
Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).
Forrester et al. (Nov. 1, 2002). "Comparison of Laser Speckle and Laser Doppler Perfusion Imaging: Measurement in Human Skin and Rabbit Articular Tissue," Medical and Biological Engineering and Computing 40(6):687-697.
Frangioni, J.V. (Oct. 2003). "In Vivo Near-Infrared Fluorescence Imaging," Current Opinion in Chemical Biology 7(5):626-634.
Frenzel H. et al. (Apr. 18, 2008). "In Vivo Perfusion Analysis of Normal and Dysplastic Ears and its Implication on Total Auricular Reconstruction," Journal of Plastic, Reconstructive and Aesthetic Surgery 61 (Supplement1):S21-S28.
Friizsch, B. et al. (Aug. 1991)."Sequential Double Labeling With Different Fluorescent Dyes Coupled to Dextran Amines as a Tool to Estimate the Accuracy of Tracer Application and of Regeneration," Journal of Neuroscience Methods 39(1):9-17.
Gagnon, A.R. et al. (2006). "Deep and Superficial Inferior Epigastric Artery Perforator Flaps," Cirugia Plástica Ibero-Latinoamericana 32(4):7-13.
Gardner, T.J. (1993). "Coronary Artery Disease and Ventricular Aneurysms," in Surgery, Scientific Principles and Practice, Greenfield, L.J. (ed.) et al., J.B. Lippincott Co., Philadelphia, PA, pp. 1391-1411, twenty three pages.
Garrett, W.T. et al. (Jul. 8, 1991). "Fluoro-Gold's Toxicity makes it Inferior to True Blue for Long-Term Studies of Dorsal Root Ganglion Neurons and Motoneurons," Neuroscience Letters 128(1):137-139.
Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," Journal Of Physical Chemistry A 107(18):3443-3449.
Gipponi, M. et al. (Mar. 1, 2004). "New Fields of Application of the Sentinel Lymph Node Biopsy in the Pathologic Staging of Solid Neoplasms: Review of Literature and Surgical Perspectives," Journal of Surgical Oncology 85(3):171-179.
Giunta, R.E. et al. (Jul. 2005). "Prediction of Flap Necrosis with Laser Induced Indocyanine Green Fluorescence in a Rat Model," British Journal of Plastic Surgery 58(5):695-701.
Giunta, R.E. et al. (Jun. 2000). "The Value of Preoperative Doppler Sonography for Planning Free Perforator Flaps," Plastic and Reconstructive Surgery 105(7):2381-2386.
Glossary, Nature, downloaded from the internet <http://www.nature.com/nrg/journal/v4/nl0/glossary/nrgl 183_glossary.html» HTML on Jun. 30, 2014, three pages.
Glover, J.C. et al. (Nov. 1986). "Fluorescent Dextran-Amines Used as Axonal Tracers in the Nervous System of the Chicken Embryo," Journal of Neuroscience Methods 18(3):243-254.
Goldstein, J.A. et al. (Dec. 1998). "Intraoperative Angiography to Assess Graft Patency After Minimally Invasive Coronary Bypass," Ann. Thorac. Surg. 66(6):1978-1982. [EXHIBIT 1007].
Gothoskar A.V. (Mar. 2004). "Resealed Erythrocytes: A Review," Pharmaceutical Technology pp. 140, 142, 144, 146, 148, 150, 152 and 154-158, twelve pages.
Granzow, J.W. et al. (Jul. 2007)."Breast Reconstruction with Perforator Flaps", Plastic and Reconstructive Surgery 120(1):1-12.
Green, H.A. et al. (Jan. 1992). "Burn Depth Estimation Using Indocyanine Green Fluorescence," Arch Dermatol 128(1):43-49.
Haglund, M. et al. (Feb. 1996). "Enhanced Optical Imaging of Human Gliomas and Tumor Margins," Neurosurgery 38(2):308-317.
Haglund, M.M. et al. (Nov. 1994). "Enhanced Optical Imaging of Rat Gliomas and Tumor Margins," Neurosurgery 35(5):930-941.
Hallock, G.G. (Jul. 2003). "Doppler Sonography and Color Duplex Imaging for Planning a Perforator Flap," Clinics in Plastic Surgery 30(3):347-357. (Per J. Liebes cite with a later OA e-mail dated Mar. 24, 2016).
Hamamatsu Brochure. (May 1997). Specifications for Real-time Microscope Image Processing System: ARGUS-20 with C2400-75i, four pages [EXHIBIT 1006].
Hamamatsu. (Date unknown). Microscope Video Camera, For Fluorescent Observation, Easy Fluorescent Image Analysis C2400-73I, -75I Series a CCD Camera, seven pages.
Hayashi, J. et al. (Nov. 1993). "Transadventitial Localization of Atheromatous Plaques by Fluorescence Emission Spectrum Analysis of Mono-L Aspartyl-Chlorin e6," Cardiovascular Research 27(11):1943-1947.
Hayata, Y. et al. (Jul. 1982). "Fiberoptic Bronchoscopic Laser Photoradiation for Tumor Localization in Lung Cancer," Chest 82(1):10-14.
He, Z. (Feb. 2009). "Fluorogold Induces Persistent Neurological Deficits and Circling Behavior in Mice Over-Expressing Human Mutant Tau," Current Neurovascular Research 6(1):54-61.
Herts, B.R. (May 2003). "Imaging for Renal Tumors," Current Opin..Urol. 13(3):181-186.
Hirano, T. et al. (1989). "Photodynamic Cancer Diagnosis and Treatment System Consisting of Pulse Lasers and an Endoscopic Spectro-Image Analyzer," Laser in Life Sciences 3(2):99-116.
Holm, C. et al. (2002). "Monitoring Free Flaps Using Laser-Induced Fluorescence of Indocyanine Green: A Preliminary Experience," Microsurgery 22(7):278-287.
Holm, C. et al. (Apr. 2003, e-published on Feb. 25, 2003). "Laser-Induced Fluorescence of Indocyanine Green: Plastic Surgical Applications," European Journal of Plastic Surgery 26(1):19-25.
Holm, C. et al. (Dec. 1, 2002). "Intraoperative Evaluation of Skin-Flap Viability Using Laser-Induced Fluorescence of Indocyanine Green," British Journal of Plastic Surgery 55(8):635-644.

(56) References Cited

OTHER PUBLICATIONS

Humblet, V. et al. (Oct. 2005). "High-Affinity Near-Infrared Fluorescent Small-Molecule Contrast Agents for In Vivo Imaging of Prostate-Specific Membrane Antigen," Molecular Imaging 4(4):448-462.
Hung, J. et al. (1991). "Autofluorescence of Normal and Malignant Bronchial Tissue," Lasers in Surgery and Medicine 11(2):99-105.
Hyvärinen, L. et al. (1980). "Indocyanine Green Fluorescence Angiography." Acta ophthalmologica 58(4):528-538. [EXHIBIT 1014].
Ikeda, S. (Jul. 1989). "Bronichial Telivision Endoscopy," Chest 96(1):41S-42S.
Indian Office Action dated Jan. 16, 2018 for Indian Application No. 2993/DELNP/2011, filed on Apr. 25, 2011, eleven pages.
Indian Office Action dated Jul. 28, 2017 for Indian Application No. 1983/MUMNP/2007, filed on Nov. 27, 2007, seven pages.
Indian Office Action dated Sep. 22, 2016 for Indian Application No. 7566/DELNP/2010, filed on Oct. 27, 2010, nine pages.
International Preliminary Examination Report completed on Aug. 22, 2019, for PCT/CA2017/050564, filed on May 10, 2017, nine pages.
International Preliminary Examination Report completed on Jul. 1, 2001 for PCT/US00/22088, filed on Aug. 11, 2000, three pages.
International Preliminary Report on Patentability dated Apr. 4, 2017 for PCT Application No. PCT/CA2015/050973 filed on Sep. 28, 2015, six pages.
International Search Report and the Written Opinion of the International Searching Authority, or the Declaration dated Apr. 3, 2008 for PCT/US07/77892, filed on Sep. 7, 2007, ten pages.
International Search Report and Written Opinion dated Jul. 29, 2009 for PCT/US2009/043975 filed on May 14, 2009, eleven pages.
International Search Report and Written Opinion dated Oct. 24, 2017 for PCT Application No. PCT/CA2017/050564 filed on May 10, 2017, fourteen pages.
International Search Report dated Dec. 3, 2009 for PCT Patent Application No. PCT/IB2009/005700, filed on Apr. 14, 2009, three pages.
International Search Report dated Dec. 3, 2015 for PCT Application No. PCT/CA2015/050973 filed on Sep. 28, 2015, three pages.
International Search Report dated Feb. 1, 2012 for PCT Patent Application No. PCT/IB2011/002381, filed on Sep. 20, 2011, five pages.
International Search Report dated Jan. 22, 2014 for PCT Application No. PCT/IB2013/001934, filed on Jun. 20, 2013, four pages.
International Search Report dated Jul. 4, 2008 for PCT Patent Application No. PCT/US2007/080847, filed on Oct. 9, 2007, three pages.
International Search Report dated Jun. 2, 2009 for PCT Application No. PCT/EP2008/008547, filed on Oct. 9, 2008, five pages.
International Search Report dated Jun. 8, 2009 for PCT Patent Application No. PCT/CA2009/000073, filed on Jan. 23, 2009, three pages.
International Search Report dated Oct. 18, 2000 for PCT Application No. PCT/US2000/22088, filed on Aug. 11, 2000, one page.
International Search Report dated Sep. 11, 2009 for Application No. PCT/US2009/042606 filed on May 1, 2009, five pages.
Invitation to Pay Additional Fees and, Where Applicable, Protest Fee mailed on Jul. 4, 2017 for PCT/CA2017/050564, filed on May 10, 2017, two pages.
Jaber, S.F. et al. (Sep. 1998). "Role of Graft Flow Measurement Technique in Anastomotic Quality Assessment in Minimally Invasive CABG," Ann. Thorac. Surg. 66(3):1087-1092.
Jagoe, J.R. et al. (1989). "Quantification of retinal damage during cardiopulmonary bypass," Third International Conference on Image Processing and its Applications (Conf. Publ. No. 307), IEE, pp. 319-323.
Jamis-Dow, C.A. et al. (Mar. 1996). "Small (< or = 3-cm) Renal Masses: Detection with CT versus US and Pathologic Correlation," Radiology 198(3):785-788.

Japanese Final Office Action dated Feb. 5, 2018 for Japanese Patent Application No. 2016-014503, filed on Jan. 28, 2016, six pages.
Japanese Final Office Action dated Jan. 28, 2019 for Japanese Patent Application No. 2016-014503, filed on Jan. 28, 2016, 3 pages.
Japanese Final Office Action dated Sep. 25, 2018 for Japanese Application No. 2017-518785 filed on Apr. 7, 2017, six pages.
Japanese Notice of Allowance dated Jan. 25, 2019 for Japanese Application No. 2017-518785 filed on Apr. 7, 2017, six pages.
Japanese Notice of Allowance dated Jun. 7, 2019 for Japanese Patent Application No. 2017-516925 filed on Mar. 28, 2017, six pages.
Japanese Notice of Allowance dated Jun. 8, 2018 for Japanese Patent Application No. 2016-203798 filed on Oct. 17, 2016, six pages.
Japanese Notice of Allowance dated Jun. 21, 2019 for Japanese Patent Application No. 2018-129970, filed on Jul. 9, 2018, six pages.
Japanese Notice of Allowance dated May 10, 2019 for Japanese Patent Application No. 2017-205499, filed on Nov. 24, 2017, six pages.
Japanese Notice of Allowance dated Sep. 16, 2016 for Japanese Patient Application No. 2015-517876 filed on Jun. 20, 2013, six pages.
Japanese Notice of Allowance dated Sep. 25, 2017 for Japanese Patent Application No. 2013-529729, filed on Mar. 21, 2013, six pages.
Japanese Office Action dated Apr. 1, 2016 for Japanese Patent Application No. 2013-529729, filed on Mar. 21, 2013, seven pages.
Japanese Office Action dated Aug. 20, 2018 for Japanese Patent Application No. 2017-205499, filed on Nov. 24, 2017, six pages.
Japanese Office Action dated Feb. 1, 2016 for Japanese Patent Application No. 2015-517876 filed on Jun. 20, 2013, eight pages.
Japanese Office Action dated Jul. 28, 2017 for Japanese Patent Application No. 2016-203798 filed on Oct. 17, 2016, four pages.
Japanese Office Action dated Jul. 30, 2013, issued in counterpart Japanese Application No. 2011-504574, filed on Apr. 14, 2009, six pages.
Japanese Office Action dated Mar. 3, 2017 for Japanese Patent Application No. 2016-014503, filed on Jan. 28, 2016, ten pages.
Japanese Office Action dated Mar. 19, 2018 for Japanese Application No. 2017-518785 filed on Apr. 7, 2017, eight pages.
Japanese Office Action dated Mar. 31, 2017 for Japanese Patent Application No. 2013-529729, filed on Mar. 21, 2013, eleven pages.
Japanese Office Action dated May 7, 2018 for Japanese Patent Application No. 2017-516925 filed on Mar. 28, 2017, four pages.
Japanese Office Action dated Nov. 19, 2018 for Japanese Patent Application No. 2017-516925 filed on Mar. 28, 2017, four pages.
Japanese Office Action dated Sep. 14, 2015 for Japanese Patent Application No. 2011-504574, filed on Apr. 14, 2009, three pages.
Jolion, J. et al. (Aug. 1991). "Robust Clustering with Applications in Computer Vision," IEEE Transactions on Pattern Analysis and Machine Intelligence 13(8):791-802.
Kamolz, L.-P. et al. (Dec. 2003). "Indocyanine Green Video Angiographies Help to Identify Burns Requiring Operation," Burns 29(8):785-791.
Kapadia, C.R. et al. (Jul. 1990). "Laser-Induced Fluorescence Spectroscopy of Human Colonic Mucosa. Detection of Adenomatous Transformation," Gastroenterology 99(1):150-157.
Kato, H. et al. (Jun. 1985). "Early Detection of Lung Cancer by Means of Hematoporphyrin Derivative Fluorescence and Laser Photoradiation," Clinics in Chest Medicine 6(2):237-253.
Kato, H. et al. (Jun. 1990). "Photodynamic Diagnosis in Respiratory Tract Malignancy Using an Excimer Dye Laser System," Journal of Photochemistry and Photobiology, B. Biology 6(1-2):189-196.
Keon, W.J. et al. (Dec. 1979). "Coronary Endarterectomy: An Adjunct to Coronary Artery Bypass Grafting," Surgery 86(6):859-867.
Kim, S. et al. (Jan. 2004, e-published Dec. 7, 2003). "Near-Infrared Fluorescent Type II Quantum Dots for Sentinel Lymph Node Mapping," Nature Biotechnology 22(1):93-97.
Kiryu, J. et al. (Sep. 1994). "Noninvasive Visualization of the Choriocapillaris and its Dynamic Filling," Investigative Ophthalmology & Visual Science 35(10):3724-3731.

(56) References Cited

OTHER PUBLICATIONS

Kitai, T. et al. (Jul. 2005). "Fluorescence Navigation with Indocyanine Green for Detecting Sentinel Lymph Nodes in Breast Cancer," Breast Cancer 12(3):211-215.
Kleszcyńska, H. et al. (Mar. 2005). "Hemolysis of Erythrocytes and Erythrocyte Membrane Fluidity Changes by New Lysosomotropic Compounds," Journal of Fluorescence 15(2):137-141.
Köbbert, C. et al. (Nov. 2000). "Current Concepts in Neuroanatomical Tracing," Progress in Neurobiology 62(4):327-351.
Kokaji, K. et al. (Date Unknown). "Intraoperative Quality Assessment by Using Fluorescent Imaging in Off-pump Coronary Artery Bypass Grafting," The Department of Cardiovascular Surgery, University of Keio, Tokyo, Japan, one page (Abstract only).
Kömürcü, F. et al. (Feb. 2005). "Management Strategies for Peripheral Iatrogenic Nerve Lesions," Annals of Plastic Surgery 54(2):135-139.
Korean Notice of Allowance dated Apr. 27, 2017 for Korean Patent Application No. 10-2016-7007994, filed on Mar. 25, 2016, three pages.
Korean Notice of Allowance dated Apr. 29, 2016 for Korean Patent Application No. 10-2010-7024977, filed on Apr. 14, 2009, three pages.
Korean Notice of Allowance dated May 20, 2019 for Korean Patent Application No. 2019-7005800, filed on Feb. 26, 2019, three pages.
Korean Notice of Allowance dated Nov. 30, 2018 for Korean Patent Application No. 10-2017-7012463, filed on May 8, 2017, three pages.
Korean Office Action dated Apr. 17, 2018 for Korean Patent Application No. 10-2017-7012463, filed on May 8, 2017, six pages.
Korean Office Action dated Dec. 4, 2018 for Korean Patent Application No. 2017-7011565, filed on Apr. 4, 2017, nine pages.
Korean Office Action dated Jun. 25, 2014 in Korean Patent Application No. 10-2013-7035027, filed on May 14, 2009, fifteen pages.
Korean Office Action dated Nov. 30, 2015 for Korean Patent Application No. 10-2010-7024977, filed on Apr. 14, 2009, two pages.
Krishnan, K. G. et al. (Apr. 1, 2005). "The Role of Near-Infrared Angiography in the Assessment of Post-Operative Venous Congestion in Random Pattern, Pedicled Island and Free Flaps", British Journal of Plastic Surgery 58(3):330-338.
Kuipers, J.A. et al. (1999). "Recirculatory and Compartmental Pharmacokinetic Modeling of Alfentanil Pigs, the Influence of Cardiac Output," Anesthesiology 90(4):1146-1157.
Kupriyanov, V.V. et al. (Nov. 2004, e-publication Sep. 28, 2004). "Mapping Regional Oxygenation and Flow in Pig Hearts In Vivo Using Near-infrared Spectroscopic Imaging," Journal of Molecular and Cellular Cardiology 37(5):947-957.
Kurihara, K. et al. (Jun. 1984). "Nerve Staining with Leucomethylene Blue: An Experimental Study," Plastic and Reconstruction Surgery 73(6):960-964.
Kyo, S. (Date Unknown). "Use of Ultrasound Cardiology during Coronary Artery Bypass Surgery," Heart and Blood Vessel Imaging II, three pages.
Lam, S. et al. (1991). "Mechanism of Detection of Early Lung Cancer by Ratio Fluorometry," Lasers in Life Sciences 4(2):67-73.
Lam, S. et al. (Feb. 1990). "Detection of Early Lung Cancer Using Low Dose Photofrin II," Chest 97(2):333-337.
Lam, S. et al. (Jul. 1, 1990). "Detection of Lung Cancer by Ratio Fluorometry With and Without Photofrin II," Proc. SPIE—Optical Fibers in Medicine V 1201:561-568.
Lam, S. et al. (Nov. 1-4, 1990). "Fluorescence Imaging of Early Lung Cancer," Annual International Conference of the IEEE Engineering in Medicine and Biology Society 12(3):1142-1143.
Lam, S.C. et al. (1993). "Fluorescence Detection," Chapter 20 in Lung Cancer, Roth, J.A. Ked.), et al., Blackwell Scientific Publications Inc., 238 Main Street, Cambridge, Massachusetts, 02142, pp. 325-338, sixteen pages.
Lanciego, J.L. et al. (Jun. 1998). "Multiple Neuroanatomical Tracing in Primates," Brain Research Protocols 2(4):323-332.
Lanciego, J.L. et al. (Oct. 1998). "Multiple Axonal Tracing: Simultaneous Detection of Three Tracers in the Same Section," Histochemistry and Cell Biology 110(5):509-515.
Laub, G.W. et al. (Nov./Dec. 1989). "Experimental Use of Fluorescein for Visualization of Coronary Arteries," Vascular and Endovascular Surgery 23(6):454-457.
Lee, E.T. et al. (Mar. 1997). "A New Method For Assessment of Changes in Retinal Blood Flow," Medical Engineering & Physics 19(2):125-130.
Leissner, J. et al. (Jan. 2004). "Extended Radical Lymphadenectomy in Patients with Urothelial Bladder Cancer: Results of a Prospective Multicenter Study," The Journal of Urology 171(1):139-144.
Leithner, C. (Jul. 14, 2003). "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet <http://edoc.hu-berlin.de/d issertationen/leith nerch ristoph-2003-07-14/>, two hundred and eight pages [English Abstract and Machine Translation].
Li, X. et al. (May 12, 2004). "Method for Retinal Vessel Detection and Diameter Measurement," Presented at Medical Imaging 2004:Image Processing, San Diego, CA, Proceedings of SPIE 5370:1746-1754.
Liedberg, F. et al. (2003). "Sentinel-Node-Diagnostik Beim Invasiven (Bladder Cancer and the Sentinel Node Concept)," Aktuel Urol. 34:115-118 (English Abstract Only).
Liedberg, F. et al. (Jan. 2006). "Intraoperative Sentinel Node Detection Improves Nodal Staging in Invasive Bladder Cancer," The Journal of Urology 175(1):84-89.
Lippincott's New Medical Dictionary. "Perfusion," p. 707 (1897), three pages.
Liptay, M.J. (Mar. 2004). "Sentinel Node Mapping in Lung Cancer," Annals of Surgical Oncology 11(Supplement3):271S-274S.
Little, J.R. et al. (May 1979). "Superficial Temporal Artery to Middle Cerebral Artery Anastomosis: Intraoperative Evaluation by Fluorescein Angiography and Xenon—133 Clearance," Journal of Neurosurgery 50(5):560-569. [EXHIBIT 1002].
Liu, Q.P. et al. (Apr. 2007). "Bacterial Glycosidases for the Production of Universal Red Blood Cells" Nature Biotechnology 25(7):454-464.
Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," Clinical Physiology 17(6):619-633.
Mack, M.J. et al. (Sep. 1998). "Arterial Graft Patency in Coronary Artery Bypass Grafting: What Do We Really Know?," Ann. Thorac. Surg. 66(3):1055-1059.
Magnani, M. et al. (1998). "Erythrocyte Engineering for Drug Delivery and Targeting," Biotechnol. Appl. Biochem. 28:1-6.
Magnani, M. et al. (Jul. 15, 1992). "Targeting Antiretroviral Nucleoside Analogues in Phosphorylated Form to Macrophasges: In Vitro and In Vivo Studies," Proc. Natl. Acad. Sci. USA 89(14):6477-6481.
Malmstrom et al. (Nov. 2002). "Early Metastatic Progression of Bladder Carcinoma Molecular Profile of Primary Tumor and Sentinel Lymph Node," The Journal of Urology 168(5):2240-2244.
Malmström, P.U. et al. (Jul. 2004). "RE: Extended Radical Lymphadenectomy in Patients With Urothelial Bladder Cancer: Results of a Prospective Multicenter Study," J. of Urol. 172(1):386, one page.
Marangos, N. et al. (Dec. 2001). "In Vivo Visualization of the Cochlear Nerve and Nuclei with Fluorescent Axonal Tracers," Hearing Research 162(1-2):48-52.
Martinez-Pérez, M. et al. (Sep. 19, 1996). "Unsupervised Segmentation Based on Robust Estimation and Cooccurrence Data," Proceedings of the International Conference on Miage Processing (ICIP) Lausanne 3:943-945.
Martinez-Perez, M.E. et al. (Aug. 2002). "Retinal Vascular Tree Morphology: A Semi-Automatic Quantification," IEEE Transactions of Biomedical Engineering 49(8):912-917.
May, S. (May/Jun. 1995). "Photonic Approaches to Burn Diagnostics," Biophotonics International pp. 44-50.

(56) References Cited

OTHER PUBLICATIONS

McKee, T.D. et al. (Mar. 1, 2006). "Degradation of Fibrillar Collagen in a Human Melanoma Xenograft Improves the Efficacy of an Oncolytic Herpes Simplex Virus Vector," Cancer Research 66(5):2509-2513.

Merriam Webster Medline Plus Medical Dictionary. "Perfusion," located at http://www.merriam-webster.com/medlineplus/perfusion, last visited on Apr. 15, 2015, one page.

Mexican Office Action dated May 30, 2013, issued in counterpart Mexican Application No. MX/a/2010/011249. no translation.

Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" Journal of Neuroscience Methods 38(2-3):183-191.

Mitaka USA, Inc. (2015). "PDE Breast Free Flap Evaluation," located at <http://mitakausa.com/category/pde_education/flaps/>, last visited on Oct. 7, 2016, four pages.

Mitaka USA, Inc. (2015). "PDE-Neo" located at <http://mitakausa.com/pde-neo/>, last visited on Oct. 7, 2016, two pages.

Mohr, F.W. et al. (May 1997). "Thermal Coronary Angiography: A Method for Assessing Graft Patency and Coronary Anatomy in Coronary Bypass Surgery," Ann Thorac. Surgery 63(5):1506-1507.

Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," Optics Letters 10(2):56-58.

Mothes, H. et al. (Nov. 2004). "Indocyanine-Green Fluorescence Video Angiography Used Clinically to Evaluate Tissue Perfusion in Microsurgery," The Journal of Trauma Injury, Infection, and Critical Care 57(5):1018-1024.

Motomura, K. et al. (1999). "Sentinel Node Biopsy Guided by Indocyanine Green Dye in Breast Cancer Patients," Japan J. Clin. Oncol. 29(12):604-607.

Mullooly, V.M. et al. (1990). "Dihematoporphyrin Ether-Induced Photosensitivity in Laryngeal Papilloma Patients," Lasers in Surgery and Medicine 10(4):349-356.

Murphy (2001). "Digital CCD Microscopy," Chapter 14 in Fundamentals of Light Microscopy and Electronic Imaging, John Wiley and Sons, pp i-xi and 259-281.

Nahlieli, O. et al. (Mar. 2001). "Intravital Staining with Methylene Blue as an Aid to Facial Nerve Identification in Parotid Gland Surgery" J. Oral Maxillofac. Surgery 59(3):355-356.

Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366, seventeen pages.

Nakayama, A. et al. (Oct. 2002). "Functional Near-Infrared Fluorescence Imaging for Cardiac Surgery and Targeted Gene Therapy," Molecular Imaging 1(4):365-377.

Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," Journal of Neuroscience Methods 103(1):11-21.

Newman et al. (Oct. 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pages.

Nimura, H et al. (May 2004, e-published on Mar. 22, 2004). "Infrared Ray Electronic Endoscopy Combined with Indocyanine Green Injection for Detection of Sentinel Nodes of Patients with Gastric Cancer," British Journal of Surgery 91 (5):575-579.

Novadaq Technologies Inc. (Jan. 29, 2007). "Novadaq Imaging System Receives FDA Clearance for use During Plastic Reconstructive Surgery," PR Newswire three pages.

Novadaq Technologies Inc. (Jan. 19, 2005). 510(k) Summary—Showing X-Ray Fluoroscopy as Predicate Device, Fluorescent Angiographic System, six pages, [EXHIBIT 1012].

Novadaq Technologies Inc.'s Preliminary Response filed on Aug. 23, 2017 to Petition for Inter Partes Review of U.S. Pat. No. 8,892,190, sixty one pages.

Oddi, A. et al. (Jun. 1996). "Intraoperative Biliary Tree Imaging with Cholyl-Lysyl-Fluorescein: An Experimental Study in the Rabbit" Surgical Laparoscopy & Endoscopy 6(3):198-200.

Ogata, F. et al. (Jun. 2007). "Novel Lymphography Using Indocyanine Green Dye for Near-Infrared Fluorescence Labeling," Annals of Plastic Surgery 58(6):652-655.

Ohnishi, S. et al. (Jul.-Sep. 2005). "Organic Alternatives to Quantum Dots for Intraoperative Near-Infrared Fluorescent Lymph Node Mapping" Molecular Imaging 4(3):172-181.

Ooyama, M. (Oct. 12-15, 1994). The 8th Congress Of International YAG Laser Symposium, The 15th Annual Meeting of Japan Society for Laser Medicine, Sun Royal Hotel, Japan, eight pages.

Ott, P. (1998). "Hepatic Elimination of Indocyanine Green with Special Reference to Distribution Kinetics and the Influence of Plasma Protein Binding," Pharmacology & Toxicology 83(Supp. II):5-48.

Oxford Concise Medical Dictionary. "Perfusion," p. 571 (1980), three pages.

Pagni, S. et al. (Jun. 1997). "Anastomotic Complications in Minimally Invasive Coronary Bypass Grafting," Ann. Thorac. Surg. 63(6 Suppl):S64-S67.

Palcic et al. (1991). "Lung Imaging Fluorescence Endoscope: A Device for Detection of Occult Lung Cancer," Medical Design and Material, thirteen pages.

Palcic, B. et al. (1990). "Development of a Lung Imaging Fluorescence Endoscope," Annual International Conference of the IEEE Engineering in Medicine and Biology Society 12(1):0196-0197.

Palcic, B. et al. (Aug. 1, 1990). "The Importance of Image Quality for Computing Texture Features in Biomedical Specimens," Proc. SPIE 1205:155-162.

Palcic, B. et al. (Jun. 1, 1991). "Lung Imaging Fluorescence Endoscope: Development and Experimental Prototype," Proc. SPIE 1448:113-117.

Palcic, B. et al. (Mar. 1991). "Detection and Localization of Early Lung Cancer by Imaging Techniques," Chest 99(3):742-743.

Pandharlpande, P.V. et al. (Mar. 2005). "Perfusion Imaging of the Liver: Current Challenges and Future Goals," Radiology 234(3):661-673.

Paques, M. et al. (Mar. 2003). "Axon-Tracing Properties of Indocyanine Green," Arch Ophthalmol. 121(3):367-370.

Parungo, C.P. et al. (Apr. 2005). "Intraoperative Identification of Esophageal Sentinel Lymph Nodes with Near-Infrared Fluorescence Imaging," The Journal of Thoracic and Cardiovascular Surgery 129(4):844-850.

Parungo, C.P. et al. (Dec. 2004, e-published on Nov. 15, 2004). "In Vivo Optical Imaging of Pleural Space Drainage to Lymph Nodes of Prognostic Significance," Annals of Surgical Oncology 11(12):1085-1092.

Peak, M.J. et al. (1986). "DNA-to-Protein Crosslinks and Backbone Breaks Caused by FAR-and NEAR-Ultraviolet and Visible Light Radiations in Mammalian Cells," in Mechanism of DNA Damage and Repair, Implications for Carcinogenesis and Risk Assessment, Simic, M.G. (ed.) et al., Plenum Press, 233 Spring Street, New York, N.Y. 10013, pp. 193-202.

Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (abstract), three pages.

Peiretti, E. et al. (May 2005). "Human Erythrocyte-Ghost-Mediated Choroidal Angiography and Photocoagulation," Investigative Ophthalmology & Visual Science, ARVO Annual Meeting Abstract 46(13):4282, located at <http://iovs.arvojournals.org/article.aspx?articleid=2403707>, last visited on Oct. 7, 2016, two pages.

Perez, M.T. et al. (Sep. 2002). "In Vivo Studies on Mouse Erythrocytes Linked to Transferrin," IUBMB Life 54(3):115-121.

Petition for Inter Partes Review of U.S. Pat. No. 8,892,190 (May 11, 2017), filed on by Visionsense Corp., fifty four pages.

Pfister, A.J. et al. (Dec. 1992). "Coronary Artery Bypass Without Cardiopulmonary Bypass," Ann. Thorac. Surg. 54(6):1085-1092, (Discussion by S.R. Gundry).

(56) References Cited

OTHER PUBLICATIONS

Phillips, R.P. et al. (1991). "Quantification of Diabetic Maculopathy by Digital Imaging of the Fundus," Eye 5(1):130-137.

Piermarocchi, S. et al. (Apr. 2002). "Photodynamic Therapy Increases the Eligibility for Feeder Vessel Treatment of Choroidal Neovascularization Caused by Age-Related Macular Degeneration," American Journal of Ophthalmology 133(4):572-575.

Profio, A.E. et al. (Jul.-Aug. 1984). "Fluorometer for Endoscopic Diagnosis of Tumors," Medical Physics 11(4):516-520.

Profio, A.E. et al. (Jun. 1, 1991). "Endoscopic Fluorescence Detection of Early Lung Cancer," Proc. SPIE 1426:44-46.

Profio, A.E. et al. (Nov./Dec. 1979). "Laser Fluorescence Bronchoscope for Localization of Occult Lung Tumors," Medical Physics 6:523-525.

Profio, A.E. et al. (Sep.-Oct. 1986). "Digital Background Subtraction for Fluorescence Imaging," Medical Physics 13(5):717-721.

Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," Journal of Neuroscience Methods 115(2):115-127.

Pyner, S. et al. (Nov. 2001). "Tracing Functionally Identified Neurones in a Multisynaptic Pathway in the Hamster and Rat Using Herpes Simplex Virus Expressing Green Fluorescent Protein," Experimental Physiology 86(6):695-702.

Raabe et al. (2009, e-published on Nov. 12, 2008). "Laser Doppler Imaging for Intraoperative Human Brain Mapping", NeuroImage 44:1284-1289.

Raabe, A. et al. (Jan. 2003). "Near-Infrared Indocyanine Green Video Angiography: A New Method for Intraoperative Assessment of Vascular Flow," Neurosurgery 52(1):132-139.

Rava, R.P. et al. (Jun. 1, 1991). "Early Detection of Dysplasia in Colon and Bladder Tissue Using Laser-Induced Fluorescence," Proc. SPIE 1426:68-78.

Razum, N. et al. (Nov. 1987). "Skin Photosensitivity: Duration and Intensity Following Intravenous Hematoporphyrin Derivatives, HpD and DHE," Photochemistry and Photobiology 46(5):925-928.

Report on Observation by C2400-75i and ARGUS20 Under Low illumination conditions, Jan. 17, 2008, six pages.

Request for Invalidation mailed on Jun. 29, 2007 for Japanese Patent No. JP-3881550, filed by Hamamatsu Photonics, Inc., eighty five pages (with English Translation).

Reuthebuch, O et al. (Feb. 2004). "Novadaq SPY: Intraoperative Quality Assessment in Off Pump Coronary Artery Bypass Grafting," Chest 125(2):418-424.

Reuthebuch, O.T. et al. (May 2003). "Graft Occlusion After Deployment of the Symmetry Bypass System," Ann. Thorac. Surg. 75(5):1626-1629.

Richards-Kortum, R. et al. (Jun. 1991). "Spectroscopic Diagnosis of Colonic Dysplasia Spectroscopic Analysis," Biochemistry and Photobiology 53(6):777-786.

Roberts, W.W. et al. (Dec. 1997). "Laparoscopic Infrared Imaging," Surg. Endoscopy 11(12):1221-1223.

Rodnenkov, O.V. et al. (May 2005). "Erythrocyte Membrane Fluidity and Haemoglobin Haemoporphyrin Conformation: Features Revealed in Patients with Heart Failure," Pathophysiology 11(4):209-213.

Ropars, C. (ed.) et al. (1987). Red Blood Cells as Carriers for Drugs. Potential therapeutic Applications, Pergamon Press, Oxford, New York, pp. v-vii, (Table of Contents only), four pages.

Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," The British Journal of Radiology 75(900):950-958.

Ross, G.L. et al. (Jul. 2004, e-published on Jun. 14, 2000). "Sentinel Node Biopsy in Head and Neck Cancer: Preliminary Results of a Multicenter Trial," Annals of Surgical Oncology 11(7):690-696.

Rossi, L. et al. (2001). "Erythrocyte-Mediated Delivery of Dexamethasone in Patients with Chronic Obstructive Pulmonary Disease," Biotechnol. Appl. Biochem. 33:85-89.

Rossi, L. et al. (1999). "Heterodimer-Loaded Erthrocytes as Bioreactors for Slow Delivery of the Antiviral Drug Azidothymidine and the Antimycobacterial Drug Ethambutol," Aids Research and Human Retroviruses 15(4):345-353.

Rossi, L. et al. (2004). "Low Doses of Dexamethasone Constantly Delivered by Autologous Erythrocytes Slow the Progression of Lung Disease in Cystic Fibrosis Patients," Blood Cells, Molecules, and Diseases 33:57-63.

Rozen, W.M. et al. (Jan. 2008). "Preoperative Imaging for DIEA Perforator Flaps: A Comparative Study of Computed Tomographic Angiography and Doppler Ultrasound," Plastic and Reconstructive Surgery 121(1):9-16.

Rübben, A. et al. (Mar. 1994). "Infrared Videoangiofluorography of the Skin with Indocyanine Green—Rat Random Cutaneous Flap Model and Results in Man," Microvascular Research 47(2):240-251.

Rubens, F.D. et al. (2002). "A New and Simplified Method for Coronary and Graft Imaging During CABG," The Heart Surgery Forum 5(2):141-144.

Russian Notice of Allowance dated Jul. 29, 2013, issued in counterpart Russian Application No. 2011111078.14, five pages.

Russian Office Action dated Mar. 29, 2013, issued in counterpart Russian Application No. 2011111078.14, three pages.

Sakatani, K. et al. (Nov. 1997). "Noninvasive Optical Imaging of the Subarchnoid Space and Cerebrospinal Fluid Pathways Based on Near Infrared Fluorescence," J. Neurosurg. 87(5):738-745.

Salmon, E.D. et al. (Oct. 1994). "High Resolution Multimode Digital Imaging System for Mitosis Studies In Vivo and In Vitro," Biol. Bull 187(2):231-232.

Sato, M. et al., (1991). "Development of a Visualization Method for the Microcirculation of Deep Viscera Using an Infrared Intravital Microscope System," Research on ME Devices and ME Technology (with English Translation), five pages.

Satpathy G.R. et al. (Oct. 2004; e-publication Aug. 7, 2004). "Loading Red Blood Cells with Trehalose: A Step Towards Biostabilization," Cryobiology 49(2):123-136.

Schaff, H.V. et al. (Oct. 15, 1996). "Minimal Thoracotomy for Coronary Artery Bypass Value of Immediate Postprocedure Graft Angiography," Supplement to Circulation 94(8):1-51, (Abstract No. 0289), two pages.

Schellingerhout, D. et al. (Oct. 2000). "Quantitation of HSV Mass Distribution in a Rodent Brain Tumor Model," Gene Therapy 7(19):1648-1655.

Schmued, L. et al. (Aug. 27, 1990). "In Vivo Anterograde and Retrograde Axonal Transport of the Fluorescent Rhodamine-Dextran-Amine, Fluoro-Ruby, Within the CNS," Brain Research 526(1):127-134.

Schmued, L.C. et al. (Oct. 29, 1993). "Intracranial Injection of Fluoro-Gold Results in the Degeneration of Local but not Retrogradely Labeled Neurons," Brain Research 626(1-2):71-77.

Schneider Jr., H.C. et al. (Jan. 1975). "Fluorescence of Testicle, An Indication of Viability of Spermatic Cord After Torsion," Urology V(1):133-136.

Seeman, P. (Jan. 1, 1967). "Transient Holes in the Erythrocyte Membrane During Hypotonic Hemolysis and Stable Holes in the Membrane After Lysis by Saponin and Lysolecithin," Journal of Cell Biology 32(1):55-70.

Sekijima, M. et al. (Sep. 2004). "An Intraoperative Fluorescent Imaging System in Organ Transplantation," Transplantation Proceedings 36(7):2188-2190.

Serov, A. et al. (Mar. 1, 2002). "Laser Doppler Perfusion Imaging with a Complimentary Metal Oxide Semiconductor Image Sensor," Optics Letters 27(5):300-302.

Serov, A.N. et al. (Sep. 23, 2003). "Quasi-Parallel Laser Doppler Perfusion Imaging Using a CMOS Image Sensor," Proc. SPIE 5067:73-84.

Sezgin, M. et al. (Jan. 2004). "Survey Over Image Thresholding Techniques and Quantitative Performance Evaluation," Journal of Electronic Imaging 13(1):146-165.

Sherif, A. et al. (Sep. 2001). "Lymphatic Mapping and Detection of Sentinel Nodes in Patients with Bladder Cancer," The Journal of Urology 166(3):812-815.

(56) References Cited

OTHER PUBLICATIONS

Sheth, S.A. et al. (Apr. 22, 2004). "Linear and Nonlinear Relationships between Neuronal Activity, Oxygen Metabolism, and Hemodynamic Responses," Neuron 42(2):347-355.
Shoaib, T. et al. (Jun. 1, 2001). "The Accuracy of Head and Neck Carcinoma Sentinel Lymph Node Biopsy in the Clinically No. Neck," Cancer 91 (11):2077-2083.
Siemers, B.M. et al. (Nov. 2001). "The Acoustic Advantage of Hunting at Low Heights Above Water: Behaviorual Experiments on the European 'Trawling' Bats Myotis Capaccinii, M Dasycneme and M. Daubentonii," J. Experimental Biol. 204(Pt. 22):3843-3854.
Skalidis, E.I. et al. (Nov. 16, 2004). "Regional Coronary Flow and Contractile Reserve in Patients with Idiopathic Dilated Cardiomyopathy," Journal of the American College of Cardiology 44(10):2027-2032.
Slakter, J.S. et al. (Jun. 1995). "Indocyanine-Green Angiography," Current Opinion in Ophthalmology 6(III):25-32.
Smith, G.A. et al. (Mar. 13, 2001). "Herpesviruses Use Bidirectional Fast-Axonal Transport to Spread in Sensory Neurons," Proceedings of the National Academy of Sciences of the United States of America 98(6):3466-3470.
Soltesz, E.G. et al. (Jan. 2005). "Intraoperative Sentinel Lymph Node Mapping of the Lung Using Near-Infrared Fluorescent Quantum Dots," Ann. Thorac. Surg. 79(1):269-277.
Sony Corporation. The Sony U-Matic Videocassette Recorder, VO-9800, ten pages, [EXHIBIT 1015].
Staurenghi, G. et al. (Dec. 2001)."Combining Photodynamic Therapy and Feeder Vessel Photocoagulation: A Pilot Study," Seminars in Ophthalmology 16(4):233-236.
Stern, M.D. (Mar. 6, 1975). "In Vivo Evaluation of Microcirculation by Coherent Light Scattering," Nature 254(5495):56-58.
Still, J. et al. (Mar. 1999). "Evaluation of the Circulation of Reconstructive Flaps Using Laser-Induced Fluorescence of Indocyanine Green," Ann. Plast. Surg. 42(3):266-274.
Still, J.M. et al. (Jun. 2001). "Diagnosis of Burn Depth Using Laser-Induced Indocyanine Green Fluorescence: A Preliminary Clinical Trial," Burns 27(4):364-371.
Stoeckli, S.J. et al. (Sep. 2001). "Sentinel Lymph Node Evaluation in Squamous Cell Carcinoma of the Head and Neck," Otolaryngol Head Neck Surg. 125(3):221-226.
Subramanian, V.A. et al. (Oct. 15, 1995). "Minimally Invasive Coronary Bypass Surgery: A Multi-Center Report of Preliminary Clinical Experience," Supplement to Circulation 92(8):I-645, (Abstract No. 3093), two pages.
Sugi, K. et al. (Jan. 2003). "Comparison of Three Tracers for Detecting Sentinel Lymph Nodes in Patients with Clinical N0 Lung Cancer," Lung Cancer 39(1):37-40.
Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," Journal of Virology 82(11):5198-5211.
Suma, H. et al. (2000). "Coronary Artery Bypass Grafting Without Cardiopulmonary Bypass in 200 Patients," J. Cardiol. 36(2):85-90, (English Abstract only).
Summary of Invention Submitted to EPO, "Development of Novadaq SPY™Cardiac Imaging Invention," five pages, EXHIBIT 1011].
Taggart, D.P. et al. (Mar. 2003). "Preliminary Experiences with a Novel Intraoperative Fluorescence Imaging Technique to Evaluate the Patency of Bypass Grafts in Total Arterial Revascularization," Ann Thorac Surg. 75(3):870-873.
Taichman, G.C. et al. (Jun. 1987). "The Use of Cardio-Green for Intraoperative Visualization of the Coronary Circulation: Evaluation of Myocardial Toxicity," Texas Heart Institute Journal 14(2):133-138.
Takahashi, M. et al. (Sep. 2004). "SPY™: An Innovative Intra-Operative Imaging System to Evaluate Graft Patency During Off-Pump Coronary Artery Bypass Grafting," Interactive Cardio Vascular and Thoracic Surgery 3(3):479-483.
Takayama, T. et al. (Apr. 1992). "Intraoperative Coronary Angiography Using Fluorescein Basic Studies and Clinical Application," Vascular and Endovascular Surgery 26(3):193-199.
Takayama, T. et al. (Jan. 1991). "Intraoperative Coronary Angiography Using Fluorescein" The Annals of Thoracic Surgery 51(1):140-143. [EXHIBIT 1013].
Tanaka, E. et al. (Jul. 2009). "Real-time Assessment of Cardiac Perfusion, Coronary Angiography, and Acute Intravascular Thrombi Using Dual-channel Near-infrared Fluorescence Imaging," The Journal of Thoracic and Cardiovascular Surgery 138(1):133-140.
Tang, G.C. et al. (1989). "Spectroscopic Differences between Human Cancer and Normal Lung and Breast Tissues," Lasers in Surgery and Medicine 9(3):290-295.
Taylor, K.M. (Apr. 1998). "Brain Damage During Cardiopulmonary Bypass," Annals of Thoracic Surgery 65(4):S20-S26.
The American Heritage Medical Dictionary. "Perfuse." p. 401 (2008), three pages.
Thelwall, P.E. et al. (Oct. 2002). "Human Erythrocyte Ghosts: Exploring the Origins of Multiexponential Water Diffusion in a Model Biological Tissue with Magnetic Resonance," Magnetic Resonance in Medicine 48(4):649-657.
Torok, B. et al. (May 1996). "Simultaneous Digital Indocyanine Green and Fluorescein Angiography," Klinische Monatsblatter Fur Augenheilkunde 208(5):333-336, (Abstract only), two pages.
Translation of Decision of Japanese Patent Office Trial Board revoking Counterpart Patent No. Patent No. 3,881,550, twenty six pages, [EXHIBIT 1010].
Tsutsumi, D. et al. "Moisture Detection of road surface using infrared camera," Reports of the Hokkaido Industrial Research Institute (No. 297), Issued on Nov. 30, 1998, two pages.
Tubbs, R.S. et al. (Apr. 2005). "Anatomic Landmarks for Nerves of the Neck: A Vade Mecum for Neurosurgeons," Neurosurgery 56(2 Suppl.):ONS256-ONS260.
U.S. Final Office Action dated Apr. 2, 2013 for U.S. Appl. No. 13/419,368, filed Mar. 13, 2012, five pages.
U.S. Final Office Action dated Apr. 4, 2017 for U.S. Appl. No. 12/933,477, filed Sep. 20, 2010, twelve pages.
U.S. Final Office Action dated Apr. 10, 2008 for U.S. Appl. No. 11/106,154, filed Apr. 14, 2005, six pages.
U.S. Final Office Action dated Apr. 12, 2017 for U.S. Appl. No. 14/543,429, filed Nov. 17, 2014, nine pages.
U.S. Final Office Action dated Apr. 20, 2016 for U.S. Appl. No. 14/543,429, filed Nov. 17, 2014, seven pages.
U.S. Final Office Action dated Apr. 27, 2011 for U.S. Appl. No. 11/515,419, filed Sep. 1, 2006, nine pages.
U.S. Final Office Action dated Aug. 10, 2012 for U.S. Appl. No. 11/912,877, filed Aug. 13, 2008, ten pages.
U.S. Final Office Action dated Dec. 4, 2014 for U.S. Appl. No. 12/776,835, filed May 10, 2010, thirteen pages.
U.S. Final Office Action dated Dec. 31, 2015 for U.S. Appl. No. 14/177,050, filed Feb. 10, 2014, eighteen pages.
U.S. Final Office Action dated Feb. 1, 2013 for U.S. Appl. No. 12/776,835, filed May 10, 2010, thirteen pages.
U.S. Final Office Action dated Feb. 4, 2015 for U.S. Appl. No. 13/314,418, filed on Dec. 8, 2011, six pages.
U.S. Final Office Action dated Feb. 13, 2015 for U.S. Appl. No. 14/543,429, filed Nov. 17, 2014, six pages.
U.S. Final Office Action dated Feb. 18, 2010 for U.S. Appl. No. 11/106,154, filed Apr. 14, 2005, six pages.
U.S. Final Office Action dated Jul. 9, 2015 for U.S. Appl. No. 14/543,356, filed Nov. 17, 2014, eight pages.
U.S. Final Office Action dated Jul. 21, 2016 for U.S. Appl. No. 14/543,356, filed Nov. 17, 2014, seven pages.
U.S. Final Office Action dated Jun. 1, 2015 for U.S. Appl. No. 14/543,429, filed Nov. 17, 2014, nine pages.
U.S. Final Office Action dated Jun. 13, 2014 for U.S. Appl. No. 12/776,835, filed May 10, 2010, thirteen pages.
U.S. Final Office Action dated Jun. 25, 2014 for U.S. Appl. No. 12/933,477, filed Sep. 20, 2010, fifteen pages.
U.S. Final Office Action dated Mar. 20, 2017 for U.S. Appl. No. 14/177,050, filed Feb. 10, 2014, twenty three pages.
U.S. Final Office Action dated Mar. 28, 2013 for U.S. Appl. No. 12/063,349, filed May 12, 2010, twenty pages.
U.S. Final Office Action dated May 29, 2013 for U.S. Appl. No. 12/933,477, filed Sep. 20, 2010, twelve pages.

(56) References Cited

OTHER PUBLICATIONS

U.S. Final Office Action dated Nov. 6, 2013 for U.S. Appl. No. 13/419,368, filed Mar. 13, 2012, five pages.
U.S. Final Office Action dated Oct. 7, 2011 for U.S. Appl. No. 11/851,312, filed Sep. 6, 2007, ten pages.
U.S. Final Office Action dated Sep. 13, 2011 for U.S. Appl. No. 11/106,154, filed Apr. 14, 2005, five pages.
U.S. Final Office Action dated Sep. 17, 2014 for U.S. Appl. No. 11/515,419, filed Sep. 1, 2006, eleven pages.
U.S. Final Office Action dated Sep. 17, 2015 for U.S. Appl. No. 12/933,477, filed Sep. 20, 2010, six pages.
U.S. Final Office Action dated Sep. 23, 2004 for U.S. Appl. No. 09/744,034, filed Apr. 27, 2001, seven pages.
U.S. Final Office Action dated Sep. 29, 2016 for U.S. Appl. No. 13/922,996, filed Jun. 20, 2013, fourteen pages.
U.S. Non-Final Office Action dated Aug. 6, 2019 for U.S. Appl. No. 15/591,909, filed May 10, 2017, nine pages.
U.S. Non-Final Office Action dated Jul. 23, 2019, for U.S. Appl. No. 15/517,895, thirteen pages.
U.S. Non-Final Office Action dated Apr. 1, 2015 for U.S. Appl. No. 12/933,477, filed Sep. 20, 2010, fourteen pages.
U.S. Non-Final Office Action dated Apr. 26, 2012 for U.S. Appl. No. 12/776,835, filed May 10, 2010, nine pages.
U.S. Non-Final Office Action dated Apr. 28, 2010 for U.S. Appl. No. 11/946,672, filed Nov. 28, 2007, nine pages.
U.S. Non-Final Office Action dated Aug. 10, 2016 for U.S. Appl. No. 14/177,050, filed Feb. 10, 2014, twenty pages.
U.S. Non-Final Office Action dated Aug. 29, 2014 for U.S. Appl. No. 12/063,349, filed May 12, 2010, nineteen pages.
U.S. Non-Final Office Action dated Dec. 16, 2016 for U.S. Appl. No. 14/868,369, filed Sep. 28, 2015, seven pages.
U.S. Non-Final Office Action dated Dec. 20, 2013 for U.S. Appl. No. 12/933,477, filed Sep. 20, 2010, thirteen pages.
U.S. Non-Final Office Action dated Dec. 30, 2010 for U.S. Appl. No. 11/106,154, filed Apr. 14, 2005, six pages.
U.S. Non-Final Office Action dated Feb. 1, 2011 for U.S. Appl. No. 11/851,312, filed Sep. 6, 2007, seven pages.
U.S. Non-Final Office Action dated Feb. 5, 2016 for U.S. Appl. No. 14/543,356, filed Nov. 17, 2014, seven pages.
U.S. Non-Final Office Action dated Jan. 8, 2018 for U.S. Appl. No. 15/077,677, filed Mar. 22, 2016, nine pages.
U.S. Non-Final Office Action dated Jan. 9, 2009 for U.S. Appl. No. 11/106,154, filed Apr. 14, 2005, six pages.
U.S. Non-Final Office Action dated Jan. 22, 2014 for U.S. Appl. No. 11/851,312, filed Sep. 6, 2007, ten pages.
U.S. Non-Final Office Action dated Jan. 27, 2012 for U.S. Appl. No. 11/912,877, filed Aug. 13, 2008, eleven pages.
U.S. Non-Final Office Action dated on Jan. 31, 2018 for U.S. Appl. No. 15/799,727, filed Oct. 31, 2017, seven pages.
U.S. Non-Final Office Action dated Jul. 2, 2015 for U.S. Appl. No. 14/177,050, filed Feb. 10, 2014, nineteen pages.
U.S. Non-Final Office Action dated Jul. 8, 2014 for U.S. Appl. No. 13/314,418, filed on Dec. 8, 2011, seven pages.
U.S. Non-Final Office Action dated Jul. 22, 2015 for U.S. Appl. No. 13/314,418, filed on Dec. 8, 2011, six pages.
U.S. Non-Final Office Action dated Jun. 11, 2013 for U.S. Appl. No. 11/515,419, filed Sep. 1, 2006, eleven pages.
U.S. Non-Final Office Action dated Jun. 28, 2012 for U.S. Appl. No. 12/063,349, filed May 12, 2010, seventeen pages.
U.S. Non-Final Office Action dated Mar. 6, 2007 for U.S. Appl. No. 11/106,154, filed Apr. 14, 2005, eight pages.
U.S. Non-Final Office Action dated Mar. 10, 2004 for U.S. Appl. No. 09/744,034, filed Apr. 27, 2001, seven pages.
U.S. Non-Final Office Action dated Mar. 13, 2015 for U.S. Appl. No. 14/543,356, filed Nov. 17, 2014, eight pages.
U.S. Non-Final Office Action dated Mar. 22, 2018 for U.S. Appl. No. 15/610,102, filed May 31, 2017, eleven pages.
U.S. Non-Final Office Action dated Mar. 22, 2019 for U.S. Appl. No. 15/799,727, filed Oct. 31, 2017, eight pages.
U.S. Non-Final Office Action dated May 6, 2015 for U.S. Appl. No. 12/063,349, filed May 12, 2010, seventeen pages.
U.S. Non-Final Office Action dated May 21, 2015 for U.S. Appl. No. 13/922,996, filed Jun. 20, 2013, fourteen pages.
U.S. Non-Final Office Action dated Nov. 9, 2015 for U.S. Appl. No. 14/177,045, filed Feb. 10, 2014, seven pages.
U.S. Non-Final Office Action dated Nov. 18, 2016 for U.S. Appl. No. 12/933,477, filed Sep. 20, 2010, six pages.
U.S. Non-Final Office Action dated Nov. 27, 2015 for U.S. Appl. No. 14/543,429, filed Nov. 17, 2014, six pages.
U.S. Non-Final Office Action dated Oct. 3, 2013 for U.S. Appl. No. 12/776,835, filed May 10, 2010, twelve pages.
U.S. Non-Final Office Action dated Oct. 12, 2016 for U.S. Appl. No. 14/543,429, filed Nov. 17, 2014, nine pages.
U.S. Non-Final Office Action dated Oct. 13, 2017 for U.S. Appl. No. 13/922,996, filed Jun. 20, 2013, seventeen pages.
U.S. Non-Final Office Action dated Oct. 26, 2017 for U.S. Appl. No. 14/543,429, filed Nov. 17, 2014, nine pages.
U.S. Non-Final Office Action dated Oct. 28, 2016 for U.S. Appl. No. 14/543,356, filed Nov. 17, 2014, eight pages.
U.S. Non-Final Office Action dated Sep. 5, 2012 for U.S. Appl. No. 12/933,477, filed Sep. 20, 2010, seven pages.
U.S. Non-Final Office Action dated Sep. 15, 2010 for U.S. Appl. No. 11/106,154, filed Apr. 14, 2005, six pages.
U.S. Non-Final Office Action dated Sep. 27, 2017 for U.S. Appl. No. 14/177,050, filed Feb. 10, 2014, twenty two pages.
U.S. Non-Final Office Action dated Sep. 30, 2010 for U.S. Appl. No. 11/515,419, filed Sep. 1, 2006, eleven pages.
U.S. Notice of Allowance dated Jul. 16, 2019, for U.S. Appl. No. 12/776,835, filed May 10, 2010, seven pages.
U.S. Notice of Allowance dated Apr. 17, 2014 for U.S. Appl. No. 13/419,368, filed Mar. 13, 2012, five pages.
U.S. Notice of Allowance dated Aug. 7, 2014 for U.S. Appl. No. 13/850,063, filed Mar. 25, 2013, nine pages.
U.S. Notice of Allowance dated Dec. 2, 2016 for U.S. Appl. No. 14/598,832, filed Jan. 16, 2015, seven pages.
U.S. Notice of Allowance dated Dec. 4, 2018 for U.S. Appl. No. 11/515,419, filed Sep. 1, 2006, seven pages.
U.S. Notice of Allowance dated Dec. 6, 2017 for U.S. Appl. No. 15/476,290, filed Mar. 31, 2017, nine pages.
U.S. Notice of Allowance dated Dec. 18, 2018 for U.S. Appl. No. 13/922,996, filed Jun. 20, 2013, six pages.
U.S. Notice of Allowance dated Jan. 10, 2019 for U.S. Appl. No. 15/610,102, filed May 31, 2017, five pages.
U.S. Notice of Allowance dated Jul. 12, 2017 for U.S. Appl. No. 14/868,369, filed Sep. 28, 2015, nine pages.
U.S. Notice of Allowance dated Jul. 13, 2016 for U.S. Appl. No. 14/598,832, filed Jan. 16, 2015, seven pages.
U.S. Notice of Allowance dated Jun. 15, 2018 for U.S. Appl. No. 11/515,419, filed Sep. 1, 2006, five pages.
U.S. Notice of Allowance dated Mar. 7, 2005 for U.S. Appl. No. 09/744,034, filed Apr. 27, 2001, five pages.
U.S. Notice of Allowance dated Mar. 15, 2016 for U.S. Appl. No. 14/598,832, filed Jan. 16, 2015, seven pages.
U.S. Notice of Allowance dated Mar. 29, 2018 for U.S. Appl. No. 14/177,050, filed Feb. 10, 2014, ten pages.
U.S. Notice of Allowance dated May 15, 2019 for U.S. Appl. No. 15/610,102, filed May 31, 2017, eight pages.
U.S. Notice of Allowance dated May 26, 2016 for U.S. Appl. No. 14/177,045, filed Feb. 10, 2014, eight pages.
U.S. Notice of Allowance dated Nov. 25, 2015 for U.S. Appl. No. 14/598,832, filed Jan. 16, 2015, seven pages.
U.S. Notice of Allowance dated Nov. 30, 2010 for U.S. Appl. No. 11/946,672, filed Nov. 28, 2007, six pages.
U.S. Notice of Allowance dated Oct. 4, 2013 for U.S. Appl. No. 11/912,877, filed Aug. 13, 2008, nine pages.
U.S. Notice of Allowance dated Oct. 6, 2014 for U.S. Appl. No. 13/419,368, filed Mar. 13, 2012, five pages.
U.S. Notice of Allowance dated Oct. 16, 2014 for U.S. Appl. No. 13/850,063, filed Mar. 25, 2013, eight pages.
U.S. Notice of Allowance dated Oct. 17, 2018 for U.S. Appl. No. 12/933,477, filed Sep. 20, 2010, seven pages.

(56) References Cited

OTHER PUBLICATIONS

U.S. Notice of Allowance dated Oct. 18, 2012 for U.S. Appl. No. 12/841,659, filed Jul. 22, 2010, seven pages.
U.S. Notice of Allowance dated Oct. 29, 2018 for U.S. Appl. No. 12/063,349, filed May 12, 2010, eight pages.
U.S. Notice of Allowance dated Sep. 6, 2018 for U.S. Appl. No. 12/776,835, filed May 10, 2010, five pages.
U.S. Notice of Allowance dated Sep. 6, 2018 for U.S. Appl. No. 13/922,996, filed Jun. 20, 2013, nine pages.
U.S. Notice of Allowance dated Sep. 11, 2018 for U.S. Appl. No. 15/799,727, filed Oct. 31, 2017, eight pages.
U.S. Notice of Allowance dated Sep. 26, 2018 for U.S. Appl. No. 15/610,102, filed May 31, 2017, eight pages.
U.S. Notice of Allowance dated Jul. 10, 2019 for U.S. Appl. No. 15/799,727, filed Oct. 31, 2017, seven pages.
U.S. Appl. No. 16/291,930, filed Mar. 4, 2019. (Copy not submitted herewith pursuant to the waiver of 37 C.F.R. §1.98(a)(2)(iii) issued by the Office on Sep. 21, 2004).
U.S. Appl. No. 16/356,766, filed Mar. 18, 2019. (Copy not submitted herewith pursuant to the waiver of 37 C.F.R. §1.98(a)(2)(iii) issued by the Office on Sep. 21, 2004).
U.S. Restriction Requirement dated Jan. 17, 2019 for U.S. Appl. No. 15/591,909, filed May 10, 2017, seven pages.
U.S. Restriction Requirement dated Jun. 26, 2017 for U.S. Appl. No. 15/077,677, filed Mar. 22, 2016, seven pages.
Unno, N. et al. (Feb. 2008, e-published on Oct. 26, 2007). "Indocyanine Green Fluorescence Angiography for intraoperative assessment of Blood flow: A Feasibility Study," Eur J Vasc Endovasc Surg. 35(2):205-207.
Uren, R.F. (Jan. 2004). "Cancer Surgery Joins the Dots," Nature Biotechnology 22(1):38-39.
Valero-Cabré, A. et al. (Jan. 15, 2001). "Superior Muscle Reinnervation after Autologous Nerve Graft or Poly-L-Lactide-e-Caprolactone (PLC) Tube Implantation in Comparison to Silicone Tube Repair," Journal of Neuroscience Research 63(2):214-223.
Van Son, J.A.M. et al. (Nov. 1997). "Thermal Coronary Angiography for Intraoperative Testing of Coronary Patency in Congenital Heart Defects," Ann Thorac Surg. 64(5):1499-1500.
Verbeek, X. et al. (2001). "High-Resolution Functional Imaging With Ultrasound Contrast Agents Based on RF Processing in an In Vivo Kidney Experiment", Ultrasound in Med. & Biol. 27(2):223-233.
Wachi, A. et al. (Apr. 1995). "Characteristics of Cerebrospinal Fluid Circulation in Infants as Detected With MR Velocity Imaging," Child's Nerv Syst 11 (4):227-230.
Wagnieres, G.A. et al. (Jul. 1, 1990). "Photodetection of Early Cancer by Laser Induced Fluorescence of a Tumor-Selective Dye: Apparatus Design and Realization," Proc. SPIE 1203:43-52.
Weinbeer, M. et al. (Nov. 25, 2013). "Behavioral Flexibility of the Trawling Long-Legged Bat, Macrophyllum Macrophyllum (Phyllostomidae)," Frontiers in Physiology 4(Article 342):1-11.
What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8Hv02FPGj>, last visited on Jan. 7, 2016, two pages.
Wise, R.G. et al. (Nov. 2005). "Simultaneous Measurement of Blood and Myocardial Velocity in the Rat Heart by Phase Contrast MRI Using Sparse q-Space Sampling" Journal of Magnetic Resonance Imaging 22(5):614-627.
Woiizik, J. et al. (Apr. 2005). "Intraoperative Control of Extracranial-Intracranial Bypass Patency by Near-Infrared Indocyanine Green Videoangiography," J. Neurosurg. 102(4):692-698.
Wollert, H.G. et al. (Dec. 1989). "Intraoperative Visualization of Coronary Artery Fistula Using Medical Dye," The Thoracic and Cardiovascular Surg. 46(6):382-383.
Written Opinion of the International Searching Authority dated Dec. 3, 2009 for PCT Patent Application No. PCT/IB2009/005700, filed on Apr. 14, 2009, six pages.

Written Opinion of the International Searching Authority dated Dec. 3, 2015 for PCT Patent Application No. PCT/CA2015/050973 filed on Sep. 28, 2015, five pages.
Written Opinion of the International Searching Authority dated Feb. 1, 2012 for PCT Patent Application No. PCT/IB2011/002381, filed on Sep. 20, 2011, four pages.
Written Opinion of the International Searching Authority dated Jan. 22, 2014 for PCT Patent Application No. PCT/IB2013/001934, filed on Jun. 20, 2013, six pages.
Written Opinion of the International Searching Authority dated Jul. 4, 2008 for PCT Patent Application No. PCT/US2007/080847, filed on Oct. 9, 2007, six pages.
Written Opinion of the International Searching Authority dated Jun. 2, 2009 for PCT Patent Application No. PCT/EP2008/008547, filed on Oct. 9, 2008, eleven pages.
Written Opinion of the International Searching Authority dated Jun. 8, 2009 for PCT Patent Application No. PCT/CA2009/000073, filed on Jan. 23, 2009, four pages.
Wu, C. et al. (Apr. 15, 2005). "cGMP (Guanosine 3',5'-Cyclic Monophosphate) Transport Across Human Erythrocyte Membranes," Biochemical Pharmacology 69(8):1257-1262.
Yada, T. et al. (May 1993). "In Vivo Observation of Subendocardial Microvessels of the Beating Porcine Heart Using a Needle-Probe Videomicroscope with a CCD Camera," Circulation Research 72(5):939-946.
Yamaguchi, S. et al. (Apr. 2005). "Evaluation of Skin Perfusion After Nipple-Sparing Mastectomy by Indocyanine Green Dye" Journal of Saitama Medical University, Japan, 32(2):45-50, (With English Abstract).
Yoneya, S. et al. (Jun. 1998). "Binding Properties of Indocyanine Green in Human Blood," IOVS 39(7):1286-1290.
Yoneya, S. et al. (Sep. 1993). "Improved Visualization of the Choroidal Circulation with Indocyanine Green Angiography," Arch Opthalmol. 111(9):1165-1166.
Young. I.T. et al. (1993). "Depth of Focus in Microscopy," SCIA '93, Proc. of the 8th Scandinavian Conference on Image Analysis, Tromso, Norway, pp. 493-498, six pages.
Golijanin, U.S. Office Action dated May 18, 2021, directed to U.S. Appl. No. 16/291,930; 19 pages.
Golijanin, U.S. Office Action dated Aug. 30, 2021, directed to U.S. Appl. No. 16/291,930; 11 pages.
Brzozowski et al., U.S. Restriction Requirement dated May 7, 2018, directed to U.S. Appl. No. 14/379,290; 7 pages.
Extended European Search Report dated Sep. 8, 2020, directed to EP Application No. 20176346.3; 9 pages.
Summons to attend oral proceedings pursuant to Rule 115(1) EPC dated Nov. 28, 2019, directed to EP Application No. 15188378.2; 7 pages.
Office Action dated Jun. 24, 2020, directed to EP Application No. 16 183 434.6; 3 pages.
Office Action dated Nov. 11, 2019, directed to EP Application No. 13 806 313.6; 7 pages.
Notice of Allowance dated Jul. 22, 2020, directed to CA Application No. 2,914,778; 1 page.
Office Action dated Nov. 18, 2019, directed to CA Application No. 2,914,778; 4 pages.
Flower et al., U.S. Notice of Allowance and Fee(s) Due dated Jan. 14, 2020, directed to U.S. Appl. No. 15/517,895; 13 pages.
Office Action dated Dec. 11, 2019, directed to CA Application No. 2,963,450; 3 pages.
Office Action dated Dec. 16, 2020, directed to CA Application No. 2,963,450; 3 pages.
Notification to Grant Patent Right for Invention dated Mar. 1, 2021, directed to CN Application No. 201480083915.1; 10 pages.
Second Office Action dated Aug. 13, 2020, directed to CN Application No. 201480083915.1; 10 pages.
First Office Action dated Nov. 22, 2019, directed to CN Application No. 201480083915.1; 17 pages.
Intention to Grant dated Jul. 28, 2020, directed to EP Application No. 14 903 635.2; 7 pages.
Office Action dated Feb. 21, 2020, directed to EP Application No. 14 903 635.2; 4 pages.

(56) References Cited

OTHER PUBLICATIONS

Intention to Grant dated Jan. 22, 2021, directed to EP Application No. 14 903 635.2; 7 pages.
Notice of Reasons for Refusal dated Sep. 13, 2019, directed to JP Application No. 2018-153572; 6 pages.
Decision to Grant a Patent dated Jan. 5, 2021, directed for JP Application No. 2020-019061; 6 pages.
Second Office Action dated Apr. 23, 2020, directed to CN Application No. 201580064648.8; 20 pages.
Third Office Action dated Oct. 21, 2020, directed to CN Application No. 201580064648.8; 13 pages.
Notification to Grant Patent Right for Invention dated Feb. 19, 2021, directed to CN Application No. 201580064648.8; 5 pages.
Decision of Refusal dated Sep. 25, 2019, directed to KR Application No. 10-2017-7011565; 7 pages.
Kolaman, A et al. (2016). "Amplitude Modulated Video Camera—Light Separation in Dynamic Scenes," IEEE Conference on Computer Vision and Pattern Recognition (CVPR) 3698-3706.
Murray et al., U.S. Office Action dated Apr. 3, 2020, directed to U.S. Appl. No. 16/746,539; 16 pages.
Intention to Grant dated Sep. 26, 2019, directed to EP Application No. 16 163 909.1; 7 pages.
Decision to Grant dated Feb. 13, 2020, directed to EP Application No. 16 163 909.1 2 pages.
Intention to Grant dated Jun. 4, 2020, directed to EP Application No. 15 846 111.1; 7 pages.
Decision to Grant dated Dec. 3, 2020, directed to EP Application No. 15 846 111.1 2 pages.
Dvorsky et al., U.S. Notice of Allowance and Fee(s) Due mailed Jul. 10, 2020, directed to U.S. Appl. No. 15/947,221; 11 pages.

* cited by examiner

Top:

Bottom:

Figure 21D

| Explanation | Page 4 of 4 | |
|---|---|---|
| | Pre Injection #1 | Post Injection #2 |
| Note: Images did not pass all quality tests (See page 3 for details) | | |

1. IMA graft
   (1). If result > 1.5
       It is usually considered to be a large perfusion increase.
       It normally happens in large stenosis and/or serve ischemia.
   (2). If result > 1 and < 1.5
       It is usually considered to be a marginal perfusion increase.
       It normally happens in relatively non serve ischemia.
   (3). If result < 1
       The possibilities are as follows:
           a. There is a technical problem in the graft.
           b. There is significant competitive flow in the IMA graft with pulsatile flow observed in the video loop.
              Because there is a delay between ICG reaching the coronary arteries and IMA,
              there is a dilution effect at the early stage of the arterial phase.
              It normally happens in relatively small stenosis without serve ischemia.
All above conclusions are based on the assumption that the Spy protocols have been strictly followed
and no other technical problems have been involved.

2. SVG/RA graft
   (1). If result > 1.5
       It is usually considered to be a large perfusion increase.
       It normally happens in large stenosis and/or serve ischemia.
   (2). If result > 1 and < 1.5
       It is usually considered to be a marginal perfusion increase.
       It normally happens in relatively non serve ischemia.
   (3). If result < 1
       The possibilities are as follows:
           a. There is a technical problem in the graft.
           b. If the stabilizing device has been used, especially in the RCA/CX region,
              sometimes, the positioning of the heart with the urchin/starfish-type retractor
              places "interesting" tension on the epicardium.
All above conclusions are based on the assumption that the Spy protocols have been strictly followed
and no other technical problems have been involved.

QUANTIFICATION AND ANALYSIS OF ANGIOGRAPHY AND PERFUSION

CROSS REFERENCE TO RELATED APPLICATION

This application is a continuation of U.S. application Ser. No. 13/922,996, filed Jun. 13, 2013, which claims the benefit of U.S. Provisional Application No. 61/662,885, filed Jun. 21, 2012, the disclosures of which are incorporated herein by reference.

BACKGROUND OF THE INVENTION

Variations in tissue perfusion have critically important consequences throughout medicine. This can be evident when not enough perfusion is available to keep tissues alive, when perfusion is restored to tissue after an acute event interrupting flow to that tissue, and when an additional source of blood flow, such as a bypass graft, is created to increase perfusion to the tissue supplied by a diseased vessel.

There are two general classifications of tissue perfusion variation, revascularization and devascularization.

Revascularization occurs when an intervention is performed to increase or restore blood flow to tissue, either by pharmacologic, catheter-based, or surgical interventions. The physiological benefit of successful revascularization is not only angiographic vessel patency, but in addition a demonstrable increase in tissue perfusion in the tissue supplied by flow within that vessel. In both circumstances, angiographic patency (vessel or graft) is one traditional marker of success. A more recently emerging consideration in the literature is the functional or physiologic success of revascularization, which is an index of the increase in perfusion to the tissue supplied by the vessel that was revascularized.

Devascularization is when tissue is deprived, either artificially or through a disease process, of enough blood flow and perfusion to compromise tissue viability. This can occur in a wide variety of surgical procedures, such as when tissue reconstruction flaps are created, or when a bowel tumor is removed and an anastomosis is performed. In these cases, maintenance of a normal threshold of perfusion to all parts of the tissue is critical to overall clinical procedural success, and to the avoidance of complications.

An example of revascularization that illustrates this principle is the setting of coronary artery bypass grafs (CABG). Here, where a stenotic area of narrowing in the vessel is bypassed, the increase in tissue perfusion results from a combination of flow down the bypass graft and the native vessel.

An example of devascularization that illustrates this principle is breast reconstruction after mastectomy, where removal of all or part of the breast is performed because of cancer. The remaining skin and underlying tissue needs to be stretched ("expanded") to create a new breast; these skin and tissue edges can be devascularized in this process, resulting in wound breakdown and scar tissue formation.

In both these examples, the ability to directly assess perfusion at the time of surgery creates the opportunity to generate new, important information for decision-making. Examples include 1) measurement of the physiologic benefit of revascularization in CABG in a way quite distinctive and supplemental to angiographic graft patency alone; and 2) measurement leading to the avoidance of areas of tissue devascularization, which would decrease the incidence of complications from this surgical procedure.

Accordingly, there is a need for an analysis platform to intra-operatively visualize, display, analyze, and quantify angiography, perfusion, and the change in angiography and perfusion in real-time in tissues imaged by indocyanine green (ICG) near-infrared (NIR) fluorescence angiography technology (ICG-N I R-FA).

BRIEF SUMMARY OF THE INVENTION

Some embodiments of the present invention provide for the derivation of unique analyzed data from ICG-NIR-FA that describes simple and complex angiography and perfusion, and their combination, across multiple clinical applications of the imaging technology.

In all embodiments, we define the term Full Phase Angiography (FPA) as consisting of three phases: 1) an arterial phase, 2) a micro-vascular phase, and 3) a venous phase. More specifically, the arterial phase is an arteriographic inflow phase, 2) the micro-vascular phase is a tissue perfusion phase in between phases 1 and 3, and 3) the venous phase is the venous outflow phase.

In some embodiments, Full Phase Angiography can be derived from any ICG-NIR-FA video, if properly captured. A properly captured video in this context would be one captured according to a protocol standardized with respect to time, dosage and image parameters.

In further embodiments, it has been determined that these three phases can be captured and elucidated in essentially all applications of the ICG-NIR-FA studied clinically thus far, and should be present in all applications of the technology assessing tissue perfusion with angiography. The characteristics of the real-time video generated by the NIR-FA system will vary according to the clinical application, in terms of length and image capture characteristics, but included in each image video are data for these three phases in all application areas. Importantly, the image capture characteristics need to be optimized in order to capture data from all three phases for the subsequent analysis platform to be accurate in its application. Therefore, the specific image capture characteristics are linked to the subsequent analysis. This approach substantially reduces the need for surgeons to make subjective judgments regarding perfusion and patency.

In still other embodiments, using our discovery of these full phase angiographic characteristics in fluorescent angiography, we have developed a core analytic platform for combined angiography and perfusion analysis, using these and other embodiments described herein. The core analytic platform is the basis for all assessments of perfusion across surgical specialties.

In still other embodiments, the core platform has been and can be extended to be applicable across Clinical Application Areas studied to date, and has been designed to be extended to new Clinical Application Areas where angiography and perfusion are important for intraoperative and experimental decision-making. Examples of Clinical Application Areas, not intended to be limiting in any way, are plastic and reconstructive surgery, wound care, vascular surgery and GI surgery.

In still other embodiments, this core analytic platform and its Clinical Application Area-specific component secondary applications are based on the following principles:

1) In some embodiments, by analyzing the arterial phase, angiographic inflow can be assessed (similar to conventional angiography). However, unlike some conventional angiography studies, the real-time characteristics of this inflow under true physiologic conditions can be readily imaged, assessed and evaluated. An example of this type of analysis is the real-time, intra-operative imaging of competitive flow in the context of CABG.

2) In some embodiments, by analyzing both the arterial phase and the microvascular phase, tissue perfusion can be imaged, assessed and quantified. An example in this context is the imaging of limb perfusion in vascular surgery.

3) In some embodiments, by analyzing the venous phase, venous congestion and outflow from tissue problems can be imaged, assessed and quantified. An example in this context is the assessment of possible venous congestion in breast reconstruction surgery.

4) In some embodiments, by capturing all three phases, with the appropriate image acquisition protocol, a complete description of the combination of angiography and perfusion as applied to that clinical application setting can be acquired and analyzed in real-time. This type of analysis might be performed in the context of esophageal or GI surgery.

5) In some embodiments, by capturing all three phases, with the appropriate image acquisition protocol, this complete description of the combination of angiography and perfusion can be evaluated against important, physiologic changes in hemodynamics and/or other conditions that would affect these angiography and perfusion comparison results.

6) In some embodiments, because this NIR imaging technology allows for capture of real-time physiology and changes over time, a dynamic analysis platform is necessary to fully describe these changes over time and accurately reflect physiology. A static, single "snapshot" analytical approach can't and won't accurately describe these physiologic changes, and is not representative of the physiologic changes that are captured by this full phase angiography analysis.

In still other embodiments, each Clinical Application Area and procedure within that Clinical Application Area relies on a certain combination of phase information derived from the FPA; this combination may be relatively specific for that procedure. All Clinical Application Areas and procedures, however, rely at a minimum on information from at least two phases, emphasizing the requirement for a dynamic analytical approach.

In further embodiments, because the anatomy and physiology varies across these Clinical Application Areas, a core analytic platform has been developed with characteristics that are applicable across all applications; additions to this core analytic platform make up the specific analytical toolkits used in each of the Clinical Application Areas.

In further embodiments, because this fluorescence technology captures information in the near-infrared (NIR) spectrum, the standard display is in 255 grey scale black and white. With the development of the analysis platform, new color schemes based on the full phase angiography components have been developed to highlight the arterial, microvascular (perfusion) and venous phases differently, based on the same NIR image. An accurate depiction of the underlying physiology requires more than just the NIR black and white image display.

In still further embodiments, because in some Clinical Application Areas there is a need to evaluate perfusion to multiple anatomic areas at the same operative setting, capturing the metadata imbedded in each of the individual analyses and combining these data into 2-D and 3-D representations is an important component and attribute of the analytic platform. These representations, in turn, are best presented as dynamic displays. Solely by way of example, in the cardiac surgery context, NIR fluorescence imaging can be performed on multiple coronary artery grafts and the data can be aggregated together to produce a dynamic 3D image of the heart showing all of the grafts and the resulting changes in perfusion of the heart muscle.

It is noted that aspects of the invention described with respect to some embodiments, may be incorporated in different embodiments although not specifically described relative thereto. That is, all embodiments and/or features of any embodiment can be combined in any way and/or combination. These and other objects and/or aspects of the present invention are explained in detail in the specification set forth below. Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 is an idealized FPA curve indicating the necessary parameters to determine the three phases (arterial, microvascular and venous), in accordance with various embodiments of the present invention.

FIG. 21, Panel A shows the Overview Display of the synchronized IDSs in standard color display (both angiography and perfusion), in accordance with various embodiments of the present invention.

FIG. 21, Panel B includes all the analysis results in accordance with various embodiments of the present invention.

FIG. 21, Panel C is the Quality Report for the data and analysis in accordance with various embodiments of the present invention.

FIG. 21, Panel D offers an explanation for the different perfusion comparison results as shown in Panel B in accordance with various embodiments of the present invention.

DETAILED DESCRIPTION OF THE PREFERRED EMBODIMENTS

Figure 1:
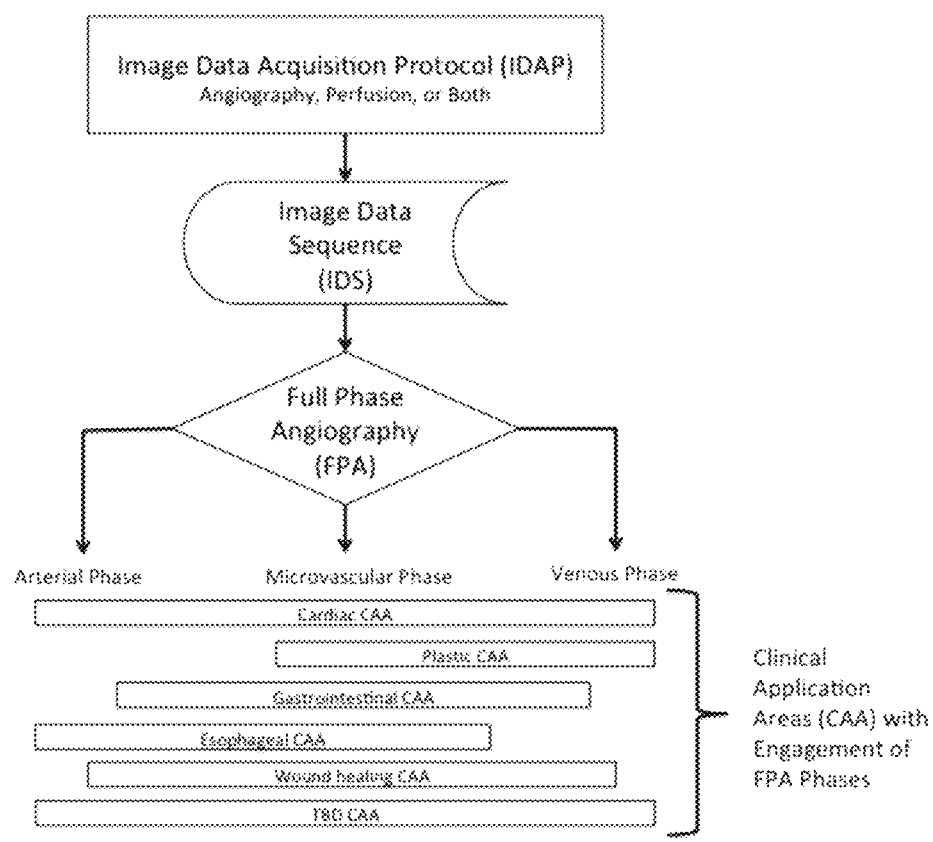
FIG. 1 is a block flow chart diagram of how the Image Data Acquisition Protocol (IDAP) and the Image Data Sequence (IDS) are critically linked to Full Phase Angiography (FPA), in accordance with various embodiments of the present invention.

Embodiments of the present invention will now be described more fully hereinafter with reference to the accompanying figures, in which preferred embodiments of the invention are shown. The invention may, however, be embodied in many different forms and should not be construed as limited to the embodiments set forth herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention. The sequence of operations (or steps) is not limited to the order presented in the claims or figures unless specifically indicated otherwise.

As will be appreciated by one of skill in the art, embodiments of the present invention may be embodied as a method, system, data processing system, or computer program product. Accordingly, the present invention may take the form of an embodiment combining software and hardware aspects. Furthermore, the present invention may take the form of a computer program product on a non-transitory computer usable storage medium having computer usable program code embodied in the medium. Any suitable computer readable medium may be utilized including hard disks, CD ROMs, optical storage devices, or other electronic storage devices.

Computer program code for carrying out operations of the present invention may be written in an object oriented programming language such as Matlab, Mathematica, Java, Smalltalk, C or C++. However, the computer program code for carrying out operations of the present invention may also be written in conventional procedural programming languages, such as the "C" programming language or in a visually oriented programming environment, such as Visual Basic.

Certain of the program code may execute entirely on one or more of a user's computer, partly on the user's computer, as a standalone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to flowchart illustrations and/or block diagrams of methods, devices, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

FIG. 1 shows the relationship between FPA and existing ICG-NIR-FA technology. In addition to the IDAP and IDS links to the FPA, FIG. 1 illustrates the FPA phase components of Arterial, Microvascular (Perfusion), and Venous Phases. Each of the currently known Clinical Application Areas (CAA) engages a minimum of two of these phases, illustrating the need for a dynamic analysis of FPA to assess both angiography and perfusion. In addition, the FPA characteristics specific for that CAA acts as a 'filter' for the IDS video loops captured for analysis.

The IDSs produced are DICOM or AVI video loops of variable duration, depending upon the Clinical Application of the imaging technology. The invention is applicable to IDSs generated from ICG-NIR-FA clinical and non-clinical research applications of the imaging technology where arteriography and/or perfusion assessment is important.

Figure 2:
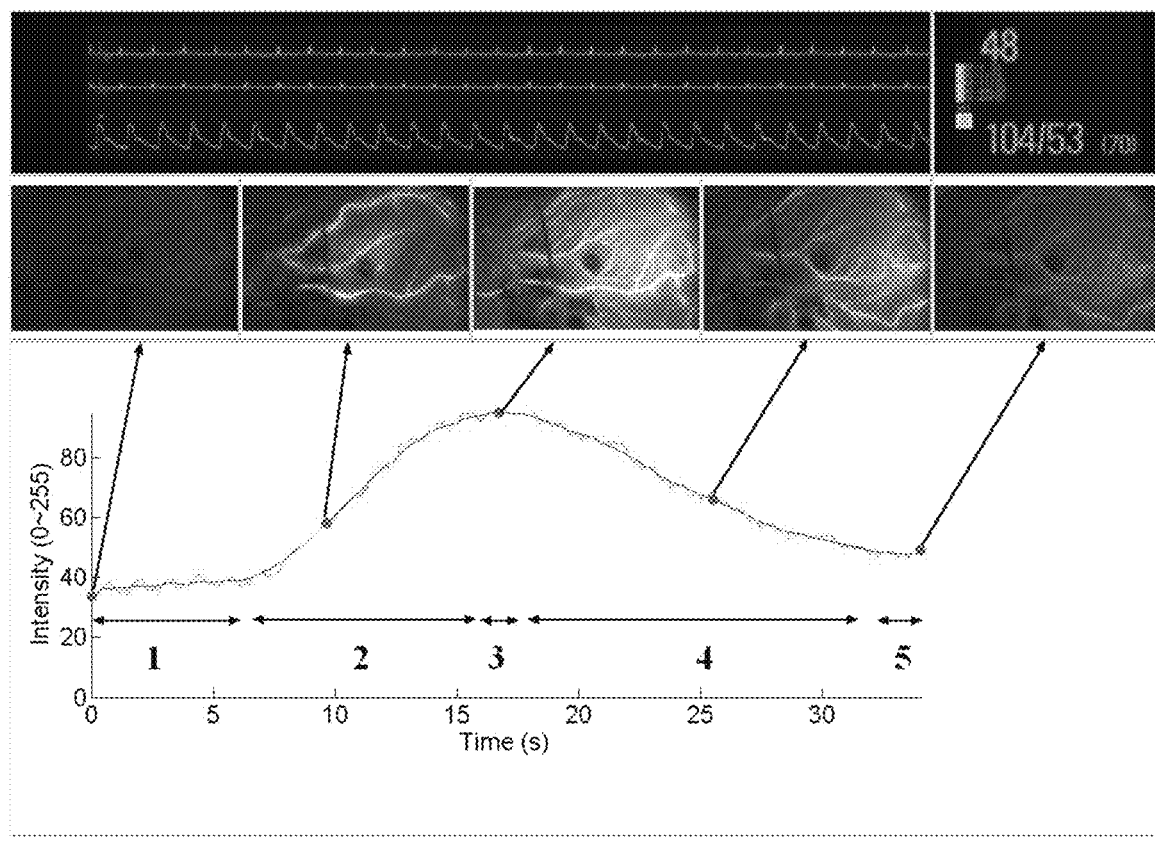
FIG. 2 is an illustration of ICG Fluorescence imaging full phase angiography (FPA) in the cardiac application, in accordance with various embodiments of the present invention.

FIG. 2 demonstrates the average intensity vs. time curve (one FPA cycle) of the 34 sec fluorescent angiography Image Data Sequence (IDS) video loop in the cardiac context. These data are fundamental to the Combined Angiographic and Perfusion Analysis (CAPA) core analysis platform. Five individual frames from the total of 1020 frames in the video loop are illustrated to illustrate the phases (1=baseline, 2=arterial phase, 3=micro-vascular phase, 4=venous phase, 5=residue of florescent dye). The ECG (green tracing) and BP (red tracing) from the continuous 26 cardiac cycles are shown.

Figure 3:
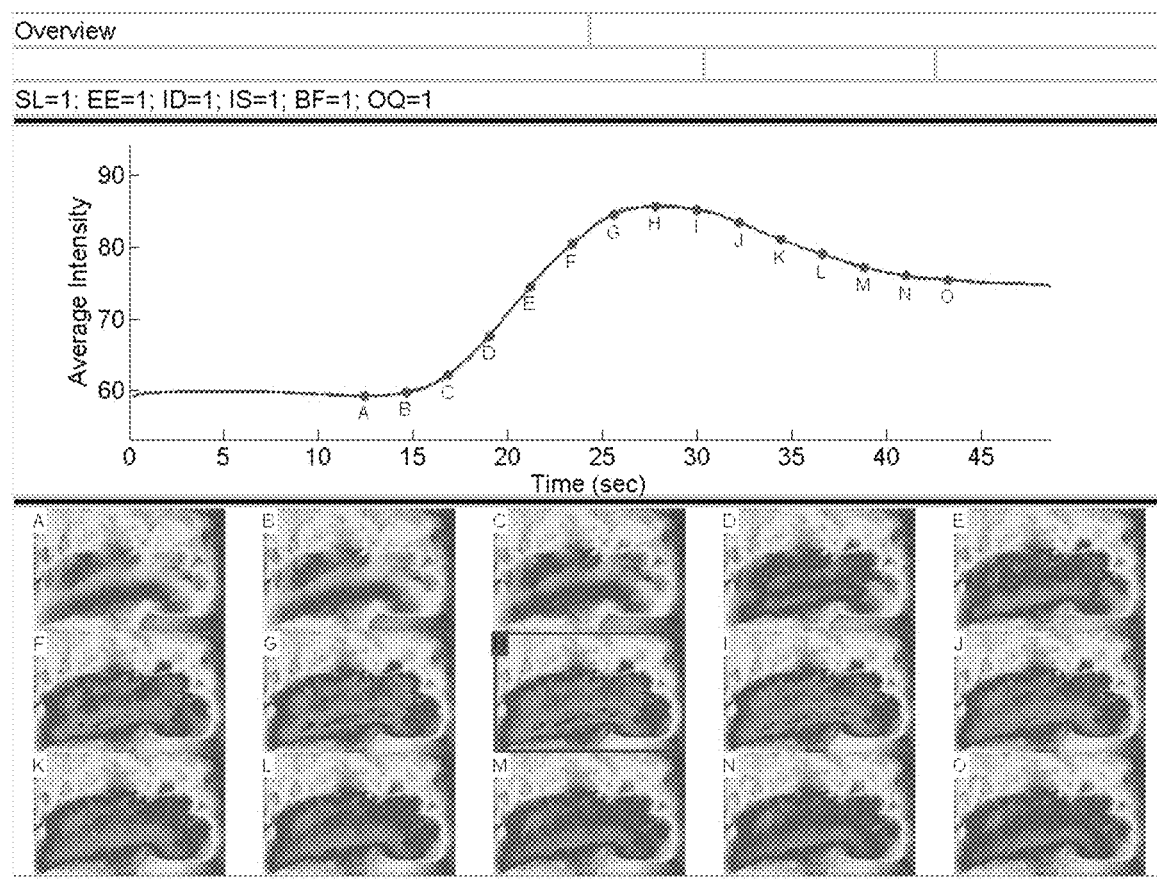
FIG. 3 illustrates full phase angiography (FPA) in the GI surgery application, in accordance with various embodiments of the present invention.

FIG. 3 illustrates FPA in the GI surgery context. Here, the three FPA phases are shown as follows: panels A-D are baseline background fluorescence; panels E-G are the arterial phase; panel H is the microvascular phase; panels I-L are the venous phase. These data are fundamental to the Combined Angiographic and Perfusion Analysis (CAPA) core platform. Shown is a segment of large bowel being imaged at the time of surgery, in the near-infrared 255 grey scale black and white Overview Display format. The peak of average fluorescence intensity for this Clinical Application Window (CAW) is in panel H. Note the IDS in this case is 45 seconds.

Figure 4:
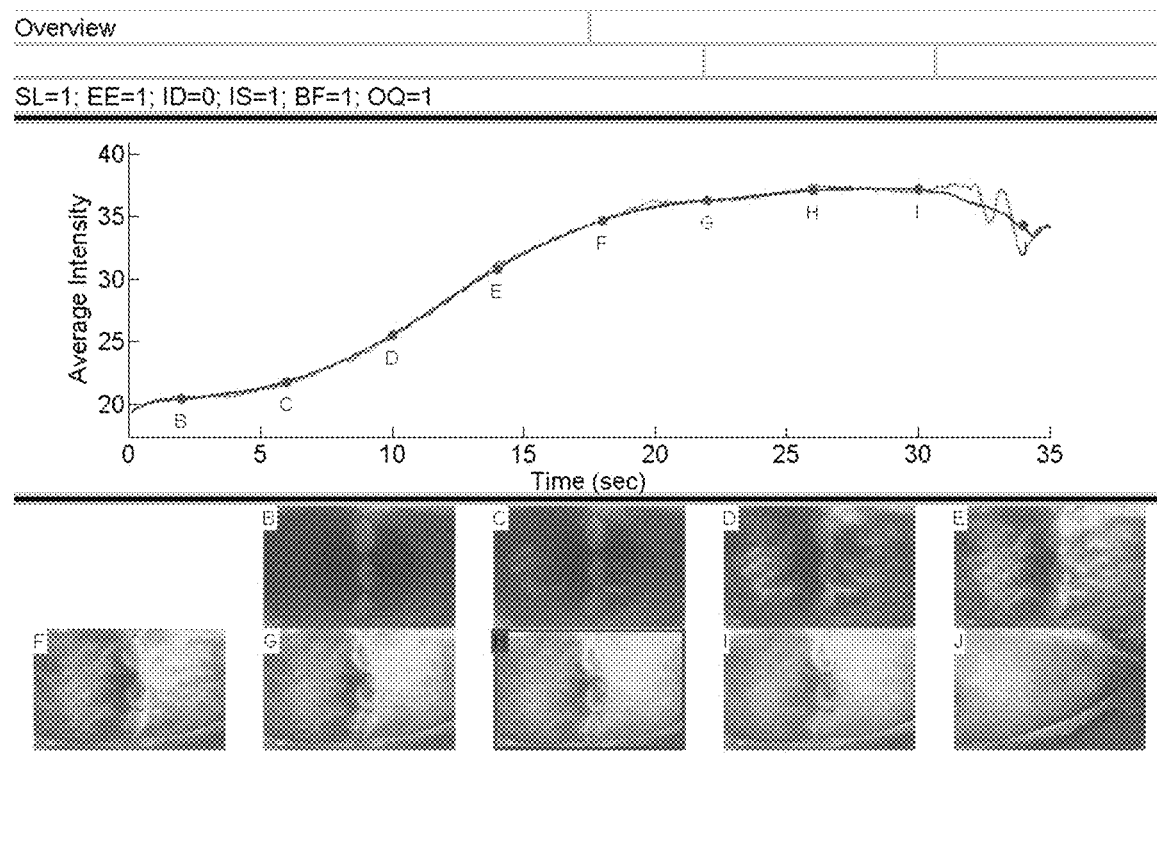
FIG. 4 illustrates full phase angiography (FPA) in the esophageal surgery application, according to various embodiments of the present invention.

FIG. 4 illustrates FPA in the esophageal surgical application. In similar fashion to FIG. 3, in FIG. 4 the peak of the average fluorescence intensity for this CAW is in panel H. These data are fundamental to the Combined Angiographic and Perfusion Analysis (CAPA) core analysis platform. This Overview Display uses the color scheme designed to highlight perfusion. The image data from the IDS are the same, however, regardless of the display presentation color scheme. Note the IDS in this case is 16 seconds.

Figure 5:
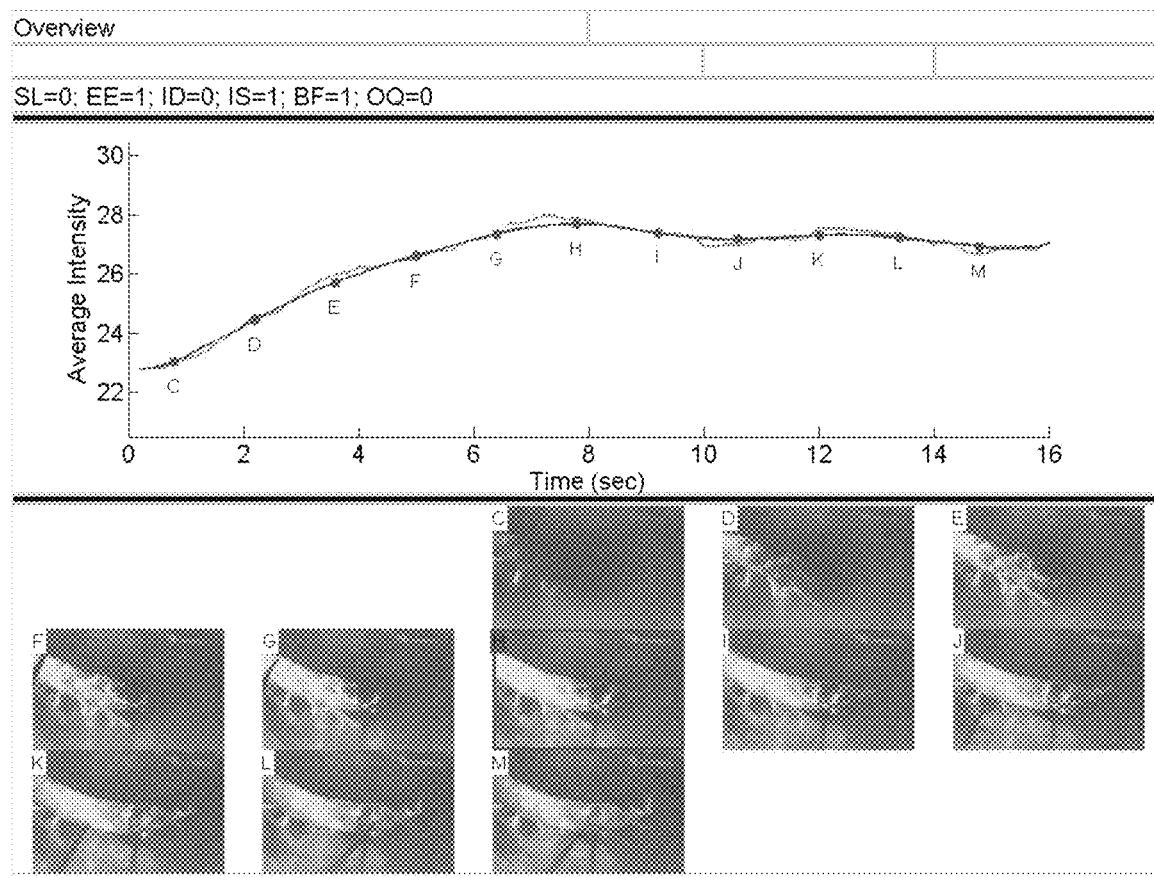
FIG. 5 illustrates the full phase angiography (FPA) in the context of breast reconstruction surgery in accordance with various embodiments of the present invention.

FIG. 5 illustrates the FPA in the plastic surgery breast reconstruction application. As in FIG. 4, in FIG. 5 the Overview Display uses the color scheme designed to highlight perfusion, and again, the peak of average fluorescence intensity for this CAW is in Panel H. These data are fundamental to the Combined Angiographic and Perfusion Analysis (CAPA) core analysis platform. Note compared to FIG. 2-FIG. 4, the venous phase of the FPA doesn't fall, suggesting venous congestion in this breast reconstruction. Note the IDS in this case is 35 seconds.

Figure 6:
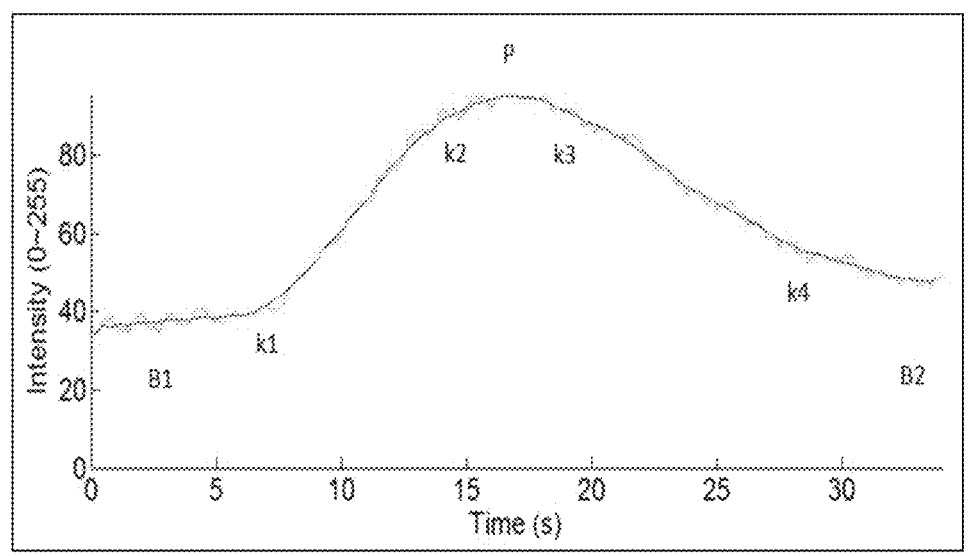
FIG. 6 shows a definition of FPA using an average intensity vs. time curve.

The modeling of a generic FPA, and the modifications for its application to a specific CAA, is as follows. The definition of FPA using an average intensity over time curve is detailed in FIG. 6.

Let B1=the average baseline intensity before the arterial phase, let P=the peak intensity, and let B2=the average baseline intensity after the venous phase. The Arterial phase starting time is defined as when the average intensity first increases to $$B1+(P-B1)\times k1 \quad \text{Equation 1}$$

And the Arterial phase ending time is defined as when the average intensity first increases to $$B1+(P-B1)\times k2 \quad \text{Equation 2}$$

Where k1 is a percentage defining the beginning of arterial phase (e.g. 5%), and k2 is a percentage defining the ending of the arterial phase (e.g. 95%).

The Venous phase starting time is defined as when the average intensity first decreases to $$B2+(P-B2)\times k3 \quad \text{Equation 3}$$

And the Venous phase ending time is defined as when the average intensity first decreases to $$B2+(P-B2)\times k4 \quad \text{Equation 4}$$

Where k3 is a percentage defining the beginning of arterial phase (e.g. 95%), and k4 is a percentage defining the ending of the arterial phase (e.g. 5%).

The Micro-vascular phase is defined as when the average intensity ranges between $$B1+(P-B1)\times k2 \quad \text{Equation 5}$$

and $$B2+(P-B2)\times k3 \quad \text{Equation 6}$$

nearby the peak.

The percentages will be somewhat different across different CAAs. The collection and analysis of clinical data is used to validate these percentages and to increase the specificity of these percentage values for each CAA utilization of the FPA 'filter.'

Figure 7:
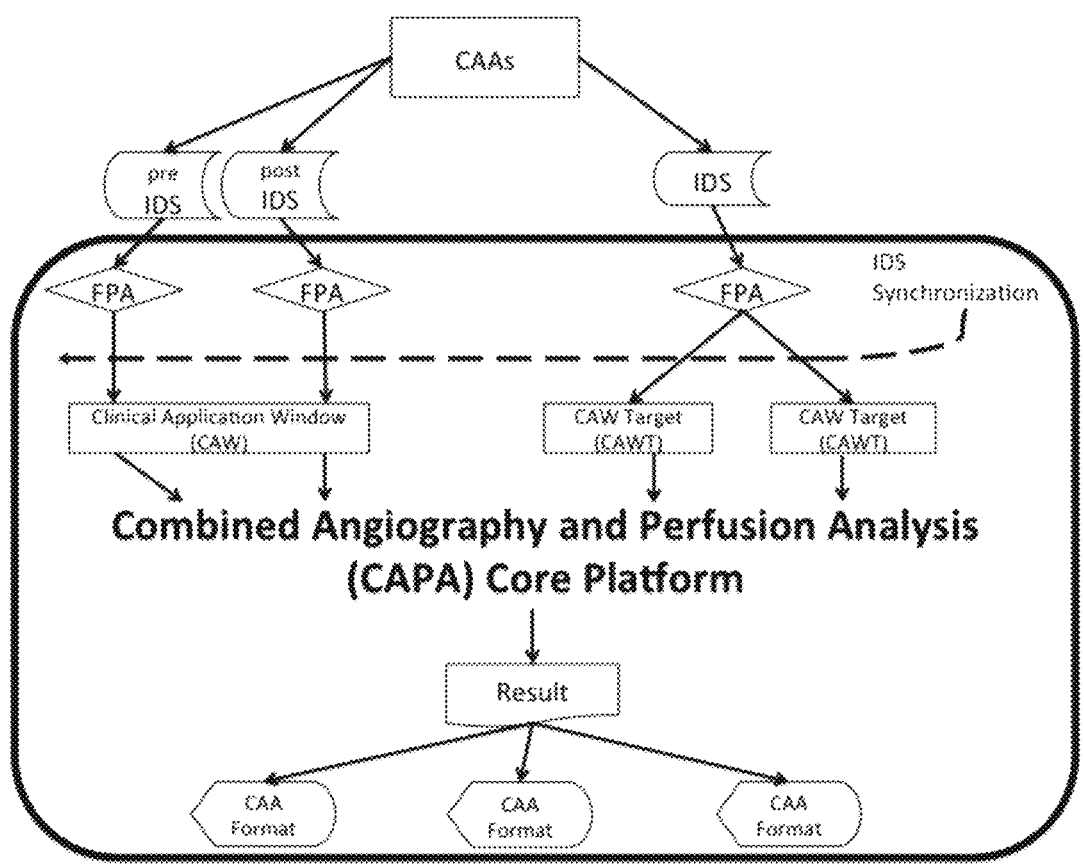
FIG. 7 is a block flow diagram of how different CAAs rely on the same Combined Angiography and Perfusion Analysis (CAPA) core platform, in accordance with various embodiments of the present invention.

FIG. 7 illustrates the Core Platform and all its component parts, including the FPA, the CAW/CAWT, the synchronization, and the analysis and results reporting. In FIG. 7, on the left side, sequential IDSs are obtained, 'filtered' through the same FPA intensity vs. time curve, synchronized, and matched according to the same Clinical Application Window (CAW). This process allows for a post- vs. pre-comparison between two IDSs to quantify the perfusion change. On the right, a single IDS in a different CAA can be 'filtered' with the FPA, and within the same CAW two different targets (CAWTs) (usually different areas) can be compared after synchronization, using the same core platform. The result output from the CAPA core platform analysis is then formatted specifically for the appropriate CAA.

FIG. 7 illustrates how the FPA acts as a 'filter' for the IDS data in particular CAAs. In some CAAs, an angiographic and perfusion comparison is made by comparing two (or more) sequential IDSs (left side of diagram), as for example before and after coronary bypass grafting. It is important that these two IDSs be captured using the same Image Data Acquisition Protocol (IDAP), and are 'filtered' with the same, CAA-specific FPA. Furthermore, the Clinical Application Window (CAW) for both needs to be the same, that is, the camera window and position of the camera (CAW) needs to be consistent between the two IDSs. This illustrates the need for a detailed and specific IDAP, since this CAW application cannot occur accurately if the IDAP generated two IDS s with different CAW information. More importantly, in the next step the core CAPA analysis cannot be reliably executed and a quantitative analysis comparison performed if this CAW isn't equally applied to both IDS+ FPA datasets.

FIG. 7 also shows a different CAA on the right, where comparative angiography and perfusion information is derived from a single IDS (such as the GI CAA). In this instance, the CAA-specific FPA 'filter' information is applied to two or more Clinical Application Window Targets; a target can be a specific area or region of the CAW (see FIG. 11), and can be manually selected or automatically selected by the FPA, and then analyzed with the platform.

Importantly, the IDS synchronization step occurs before the CAW/CAWT step, to avoid comparing data that are inadequate for analysis.

The Results of the analysis are reported in a format that is most applicable to the specific CAA, to assist the surgeon with new, real-time information in the operating room with which to make better decisions and decrease the incidence of complications.

Figure 8:
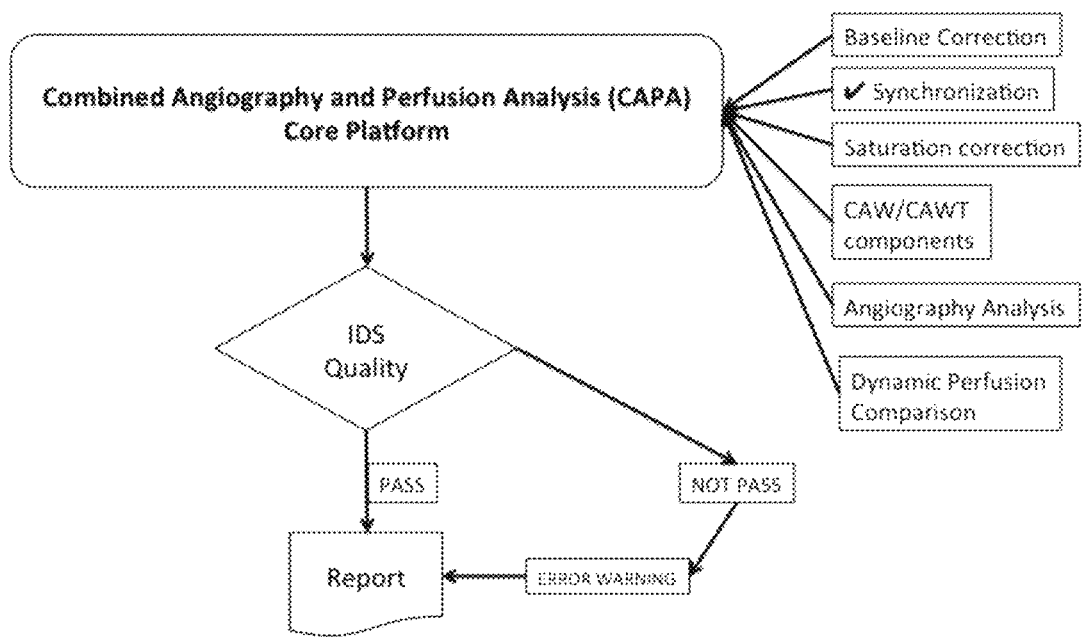
FIG. 8 illustrates the combined analytical components (baseline correction, synchronization accuracy check, angiography characteristic assessment, and dynamic perfusion comparison) that are part of the CAPA core platform, in accordance with various embodiments of the present invention.

FIG. 8 illustrates the unique attributes of this analysis platform. These include: 1) baseline correction algorithm; 2) synchronization validation; 3) saturation correction; 4) CAW/CAWT component application(s); 5) angiography analyses (where applicable); and 6) the dynamic and quantitative perfusion comparison(s). Importantly, this CAPA is a dynamic, as opposed to static, analysis platform, accurately reflecting the underlying physiology as captured in the FPA construct. It contains in addition the following attributes: 1) a dynamic analysis of both angiography and perfusion in the same construct; 2) real-time, intraoperative image analysis capabilities, based on unmodified image data captured with the ICG Fluorescence system; 3) built-in image data quality checks and evaluation processes with which to frame the analysis results; 4) image and analytical results displays that reflect the concept and principles of FPA as critical to understanding and visualizing the underlying physiology being studied and evaluated during these surgical procedures; and 5) real-time 2-D and 3-D displays of the analyzed data for rapid, visual-based documentation of the analytical results, some in the format of a dynamic movie. Additionally, the CAPA analysis and display can be used for new and technologically-sophisticated information documentation in healthcare. This includes information sharing among healthcare professionals and with patients and their families, in which the dynamic visualization of the revascularization and/or devascularization conditions of the surgical procedure can be displayed. In addition, this CAPA infrastructure creates the opportunity for longitudinal analysis of the metadata contained in the analyzed information.

In FIG. 8, some of these combined analytical components (baseline correction, synchronization accuracy check, angiography characteristic assessment, and dynamic perfusion comparison) are used across all CAAs; others are specifically emphasized for other CAAs because of the underlying physiology being imaged. The IDS Quality check was placed post-analysis, so as not to place the surgeon in the position of having no analysis generated following data acquisition; however, if the IDS(s) do not meet the data quality checks, assuring that the IDAP was adhered to and that other physiological conditions were met as well, the Report will contain and Error Warning indicating that the following image quality metrics were not met.

Figure 21A:
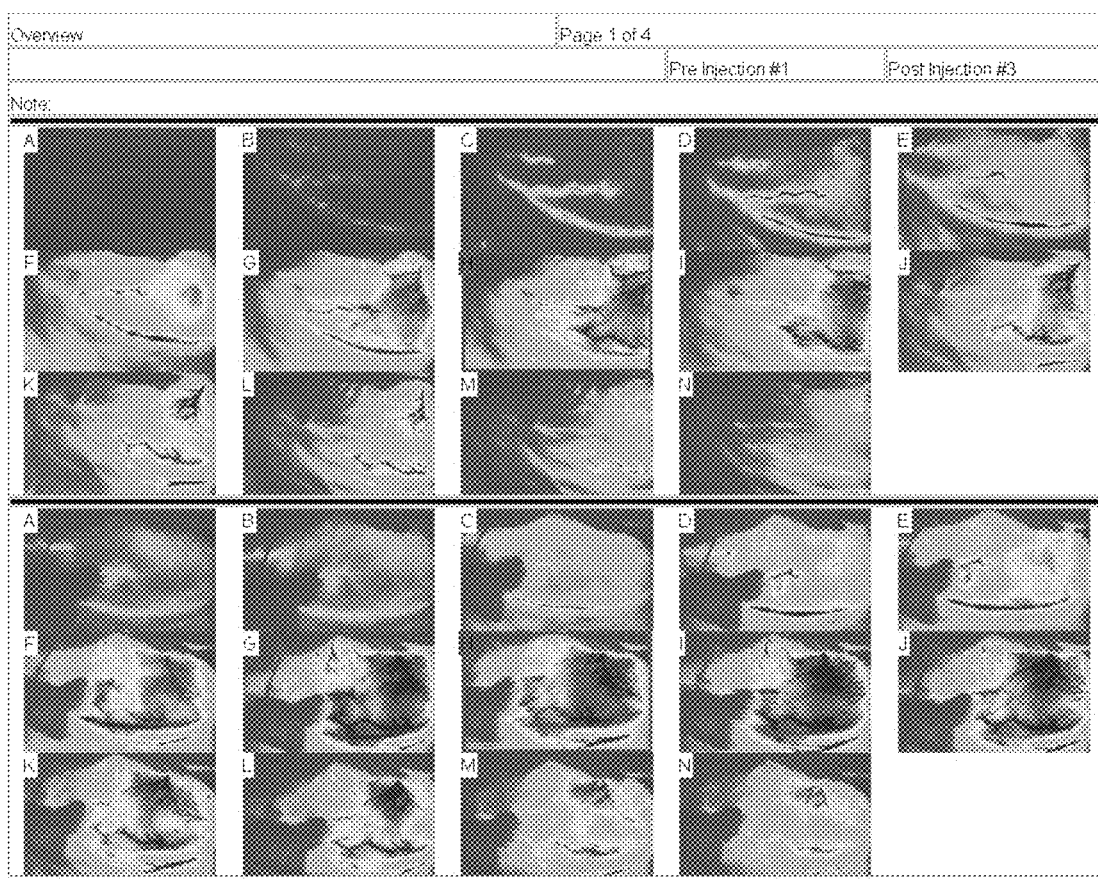
FIG. 21 A-D illustrates the CAPA core platform report format in accordance with various embodiments of the present invention.
Figure 21B:
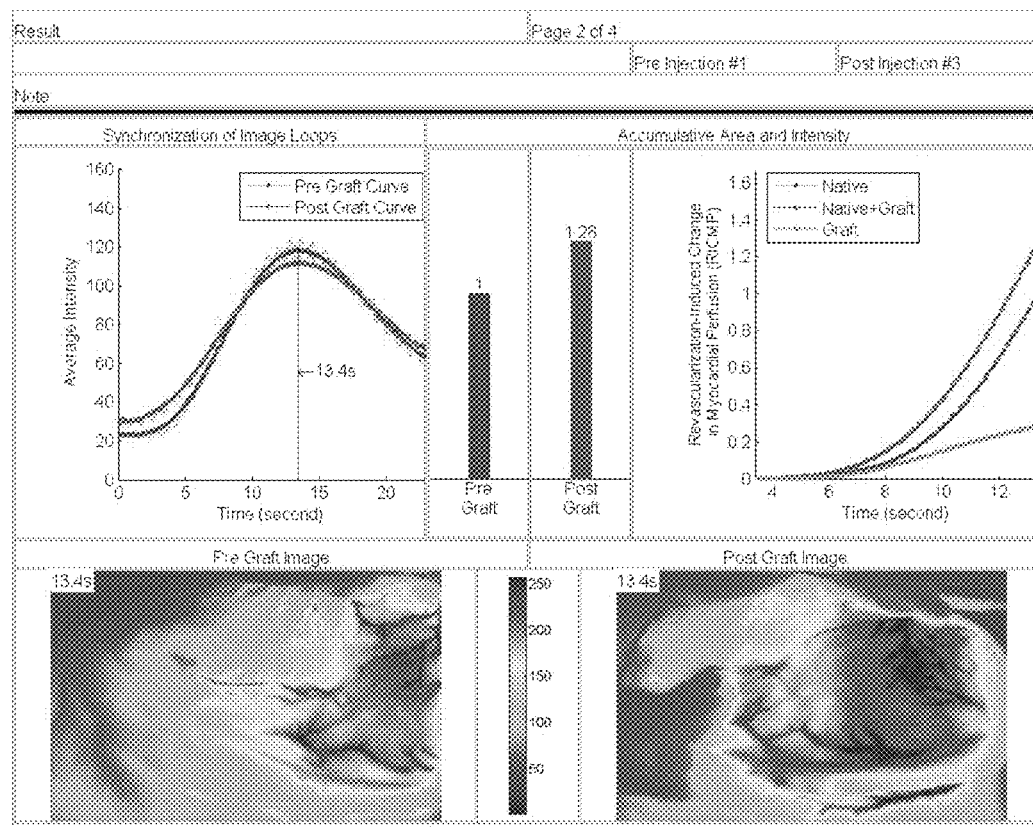
Figure 21C:
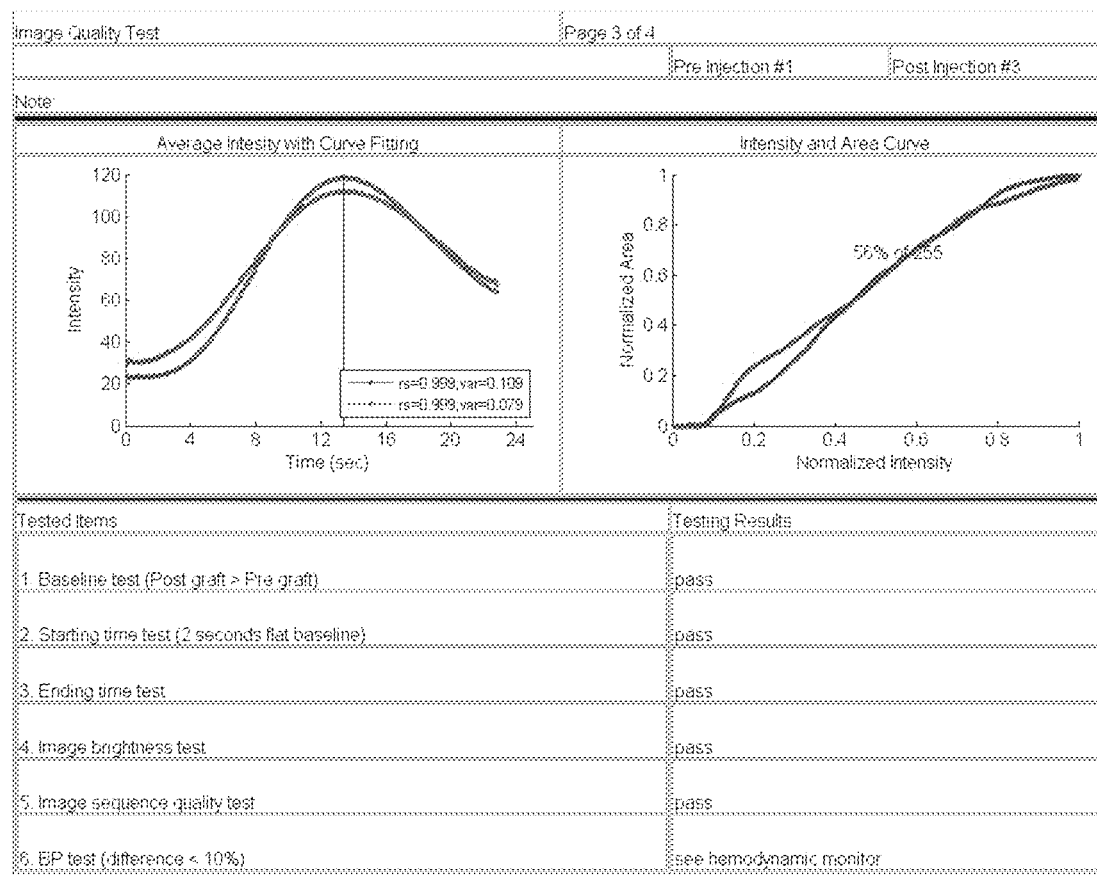

Fluorescence angiography relies on low-energy, NIR laser excitation of ICG in blood vessels and perfused tissues, with capture of the intensity of fluorescence based upon the ICG infrared absorption and emission spectra. Importantly and in addition, imaging and its interpretation are influenced by a number of physiologic and/or pathophysiologic circumstances. The imaging data are captured as standard AVI and/or DICOM video loops at 30 fps, which can be directed imported into the core analytical platform. These standard image formats make the analytical platform widely applicable from a technical perspective. The frame rate was accounted for in the development of the CAPA core platform, as it limits the fidelity of the image analysis. An example of this is shown in FIG. 21 A, where the "movement" in the images on the Display results from the movement of the heart exceeding the frame rate of the camera at that point in the IDS video.

The known behavior of ICG dye in the blood has established that on the first pass through the heart, the fluorescence intensity is proportional to the concentration of ICG, which in turn is directly related to the injected dose. This allows for tailoring of the ICG dosage/injection for specific Clinical Application Areas and procedures within those areas. Importantly, this behavior also creates the possibility of fluorescence saturation, where the quantification of the intensity exceeds the 0-255 scale. This creates a problem of being unable to quantify how much greater than 255 the actual fluorescence intensity actually is; this is particularly a problem in other ICG-NIR-FA analysis approaches. As demonstrated, the CAPA analysis accounts for saturation correction when it does occur.

The known behavior of ICG dye as a bolus injection, with or without a saline flush, allows for specific detailing of how the ICG injection should be administered in order to optimize image quality. This understanding has specific importance in those CAAs where the angiography analysis is of particular relevance. The ICG bolus stays relatively undispersed as it passes through the central cardiac circulation, and ultimately out to the peripheral tissue microvasculature. Even at this anatomic location extremely distant physiologically from the heart, the FPA and its phase components can be readily identified in the ICG-NIR-FA IDS sequences. This documented discovery creates the opportunity to establish the CAPA core platform as an independent claim applicable across all ICG-NIR-FA applications involving angiography and perfusion. Now and in the future, supplemental analytical components that are specific to the existing and new CAAs can and will be developed as dependent claims.

The known behavior of ICG dye in blood and in circulation is fundamental to this imaging technology and analysis. ICG binds to the circulating proteins in serum, and to endothelial proteins attached to the inner surface of arterial and venous blood vessels. The half-life of ICG in humans is about 3 minutes, and the dye is metabolized by the liver and excreted in the kidney. Because the surface area on the venous side of the circulation is so much greater than the arterial side, there is more endothelial binding on the venous side, creating residual fluorescence, which typically is 'washed out' in 4-5 minutes after an injection. As demonstrated, our discovery and analysis of FPA, however, led to the understanding of how to deal with residual, background fluorescence in a physiologically-accurate manner that meets the time frame for this imaging technology to be adopted and used clinically by surgeons during complex operative procedures.

As with any imaging technology, image data acquisition is key to sustained, successful analysis across multiple providers in multiple settings. The standardization of these image acquisition parameters for each Clinical Application Area is critical for the analysis claim of the invention to be used appropriately and for the results to be used accurately in the clinical setting. As related to the invention, it is critically important that the image acquisition process for each CAA enables the complete capture of the FPA information, which is, as demonstrated, a key component for the CAPA platform analysis of angiography and perfusion in that CAA, and that surgical procedure.

We have defined the term Image Data Sequence (IDS) as the captured video loop with all the imbedded metadata. This IDS may be of variable duration, depending upon the application. As shown in FIG. 7, the use and management of the IDS is specific for each CAA.

We have defined the term Image Data Acquisition Protocol (IDAP) as the specific, step-by-step process of coordinated capture of the IDS. This includes: 1) machine setup and positioning of the field of view, specific to the application and procedure; 2) the dosage, administration route and timing of administration of the ICG fluorescent dye coupled with management of the data capture software on the ICG Fluorescence machine; and 3) any specific technical, clinical or hemodynamic management processes necessary for optimization of the IDAP.

In addition, there are specific subset applications of the IDAP, depending upon the relative predominance of the arterial, microvascular and venous phases in that particular CAA and surgical procedure application. In these cases, the IDAP needs to be designed and executed so as to assure the time frame of data capture encompasses the necessary FPA spectrum. For example, in a CAA that is dependent upon the arterial phase, starting the video capture without a stable baseline makes a comparative analysis unfeasible. Similarly, truncating the video capture, or moving the machine, or shining the surgeon's headlight into the field, before the necessary venous phase information is captured creates an analytical problem. The specific IDAP must reflect a very real understanding of the FPA, its principles, and the CAPA platform.

In certain CAAs, specific IDAPs are developed for imaging purposes specific to either angiography or perfusion. For example, in the cardiac application, at the end of the revascularization procedure, with the heart in the anatomic position in the mediastinum, the 'aortic root shot" is obtained, to illustrate flow and subjective rate of flow down the graft conduits, and to assess the anastomoses constructed to the ascending aorta, and to identify subtle technical issues (air bubble, low flow rate vs. other grafts) (FIG. 9).

Figure 9:
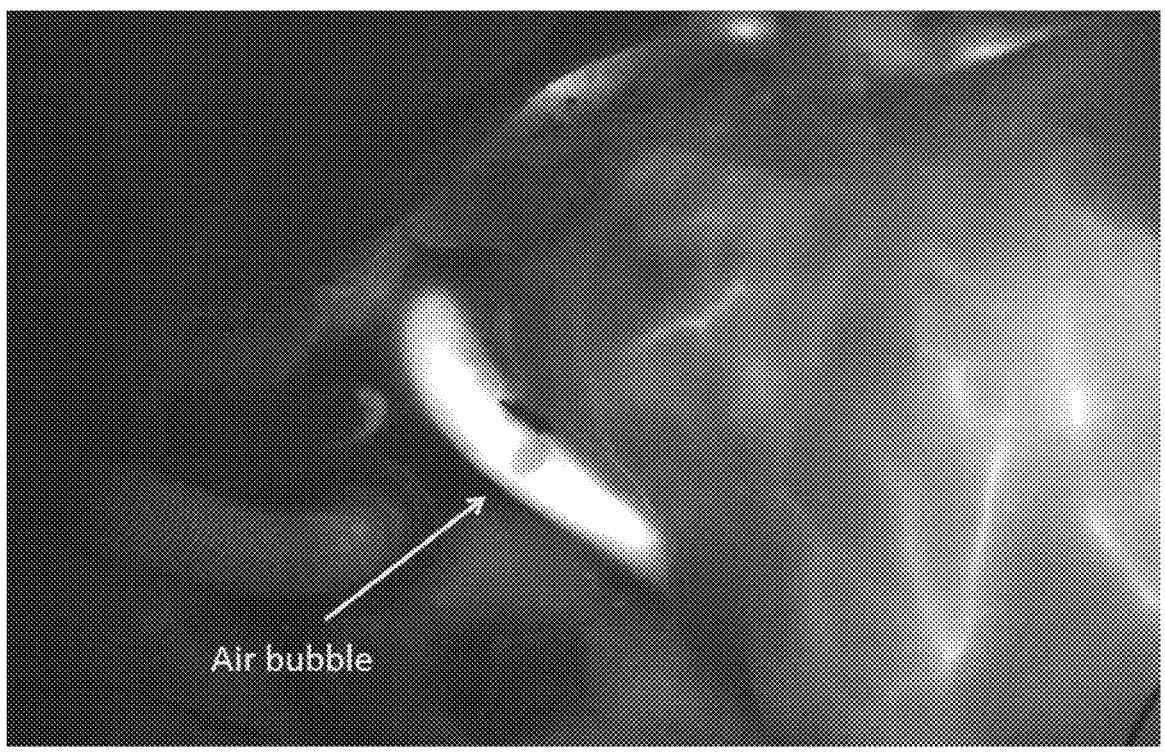
FIG. 9 illustrates in the cardiac application the 'aortic root shot," identifying an air bubble in a bypass graft attached to the ascending aorta, in accordance with various embodiments of the present invention.

As is demonstrated in FIG. 9, this bubble could not have been recognized without ICG-NIR-FA imaging, and was aspirated before it could embolize down the bypass graft to the heart and cause heart damage.

Figure 10:
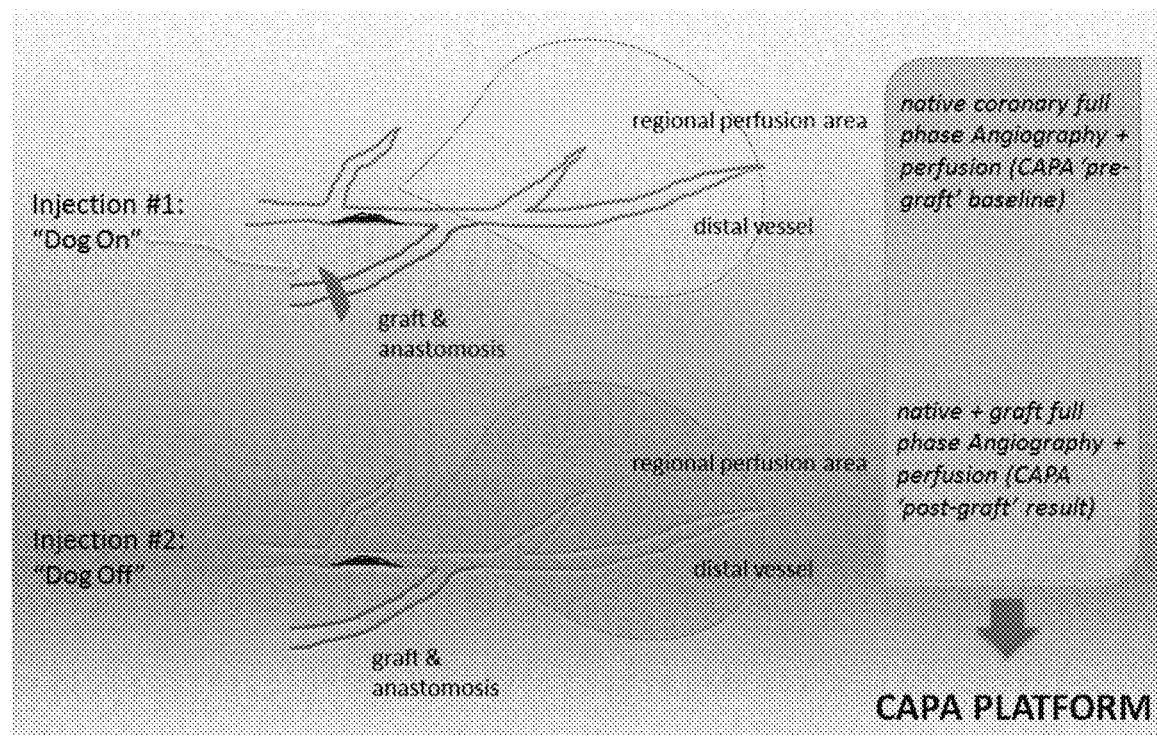
FIG. 10 shows the Coronary Bypass Graft Image Protocol (CBGIP) according to various embodiments of the present invention.

Also in certain CAAs, intraoperative techniques have been developed to specifically facilitate IDS capture in a framework that enables subsequent analysis. For example, in the cardiac application, we have determined that the most reliable approach to consistent angiography and perfusion analysis is the following Coronary Bypass Graft Image Protocol (CBGIP) (FIG. 10). In FIG. 10, the CBGIP sequence consists of: a) graft anastomosis construction; b) first IDS acquisition with a soft-jawed clamp on the bypass conduit ("dog on") to assess visually native coronary flow and perfusion to confirm that the native circulation has not been interrupted by the anastomosis, reflux up the bypass conduit as an index of anastomotic patency, and any other technical issues (air bubble, dissection flap in epicardial coronary artery); c) saving the first IDS image with removal of the soft-jawed clamp from the graft conduit; then d) second IDS acquisition with both the native coronary flow and graft flow together. In this way, all of the following FPA-derived and related important information can be captured by adhering to the IDAP, CAA-specific protocol: 1) visual assessment of evidence for adequate flow down the conduit; 2) the presence of competitive flow between the native and graft conduits; 3) the briskness of washout of ICG-blood from the graft conduit; 4) any other technical issues (air bubble, poor outflow, dye 'hang up' at the anastomosis); and 5) the subsequent CAPA platform analyses.

FIG. 10 illustrates the important connectivity between the present invention(s) of the FPA and CAPA analysis platform, and the methodology for collecting the ICG-NIR-FA image data. These two processes must be aligned by the clinical/ experimental providers to optimize the accuracy and fidelity of the analytical and display results, as is the case with any imaging and analytical technologies.

As shown in FIG. 1 and FIG. 7, the CAPA platform extends across all the CAAs identified thus far. Moreover, since the principle of FPA embodiments has been identified in all applications of ICG-NIR-FA thus far studied, we expect that it will apply to any ICG-NIR-FA application area where angiography and perfusion are critically important.

The dynamic and flexible nature of the FPA in this context is reflected in various embodiments of the embodiments in the present invention(s).

We define the image area to which the FPA 'filter' intensity vs. time curve is applied as the Clinical Application Window (CAW), and/or to a sub-set of this window, termed the Clinical Application Window Target (CAWT).

Figure 11:
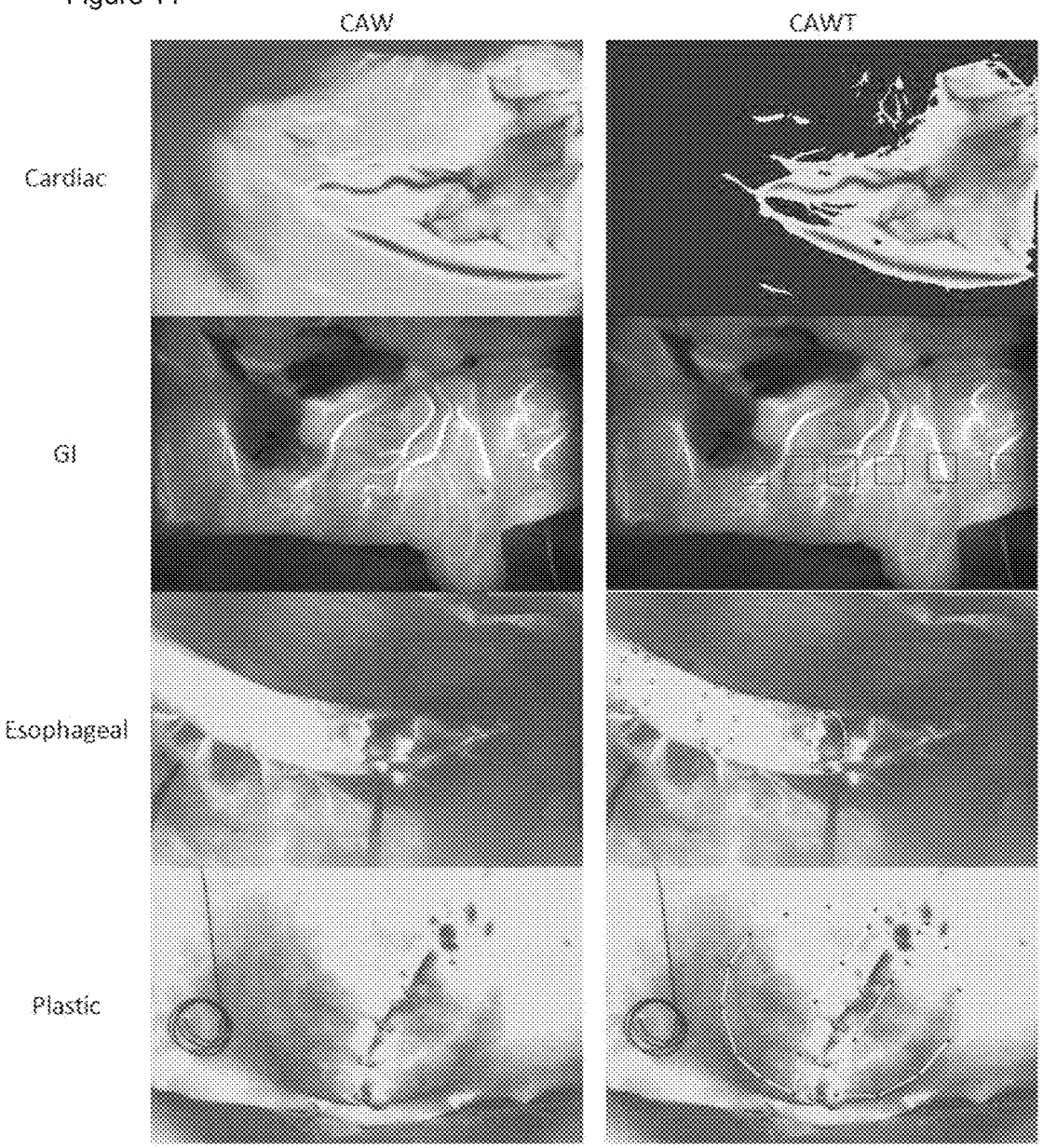
FIG. 11 is an illustration of the CAW (clinical application window) and CAWT (CAW target) as applied to a variety of CAAs identified thus far, in accordance with various embodiments of the present invention.

FIG. 11 is an illustration of the CAW and CAWT as applied to a variety of CAAs identified thus far. As shown in FIG. 11, the CAWT can be selected automatically (as in cardiac by the analysis algorithm) or manually.

This CAW is the area of clinical interest for imaging, and will be variable from application to application, but as shown in FIG. 7 the core CAPA platform uses information from this CAW to further define the parameters of the analysis beyond the FPA 'filter,' and to make sure that the comparisons being made are accurate and reflective of the underlying physiology.

The CAWT can be individual image pixels in a CAW, a certain selection and/or identified grouping of pixels, or an anatomic subset of the CAW as defined by the clinical application. The target can be manually selected, or automatically computer generated. The physiology of arterial flow and perfusion predicts that different CAWTs will, at any point in time, have different intensity vs. time curve characteristics.

Because the opportunity inherent in FPA and the CAPA is a dynamic analysis that reflects physiology, an important observational finding present in all CAAs studied thus far and critical for the analytical platform is that the predominant blood supply source engages the tissue being imaged be identified. This allows identification of a proximal (nearest to the blood supply origin) and a distal end (farthest away from the proximal end). The perfusion analysis must account for the entirety of the arterial and micro vascular phases in real time rather than just a single static frame from the image sequence. As mentioned, if the CAWT is defined as a certain selection and/or identified grouping of pixels in a CAW, during a single ICG injection that selection/grouping of pixels image arterial, micro-vascular and venous phases of full phase angiography. For that pixel CAWT and for the CAW as a whole, the image characteristics are very different from phase to phase. Since adjacent CAWT will have different characteristics, these differences in intensity and time can be used to derive comparative and contrasting data throughout the CAW.

Due to the limitations of 8-bit cameras, the intensity of fluorescence measurement in any IDS is limited to 255. At times, based on physiological or pathophysiologic circumstances, the same dose and concentration of ICG dye could in theory create saturation (intensity>255) in the IDS for part of the sequence. This saturation effect has been observed, especially with multiple injections, and this might jeopardize the accuracy of the perfusion comparison. To address this, we created an algorithm to estimate "real" intensity of the saturated pixels from the image histogram and approximate their distribution above intensity 255 by estimating the distribution of the pixels with intensity smaller than 255. Their geographical locations can be also estimated using non-saturated frames previous to the saturated frame.

Figure 12:
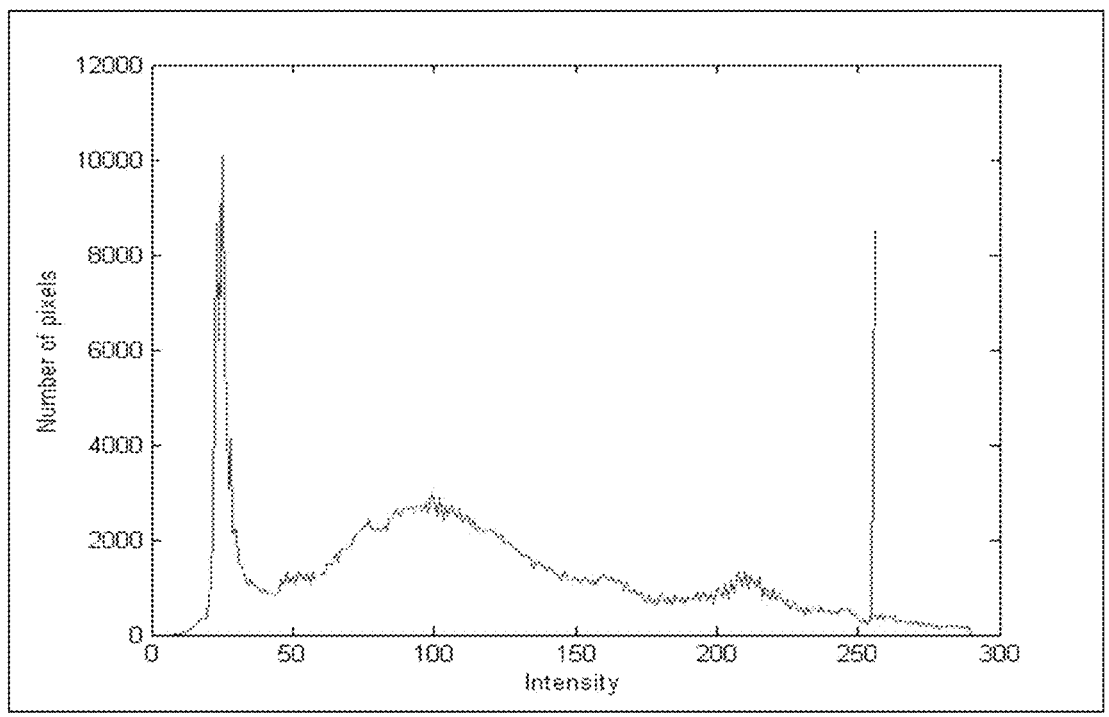
FIG. 12 is an illustration of a method for Saturation Correction, according to various embodiments of the present invention.

FIG. 12 illustrates the method for saturation correction. In this figure, the blue color curve is the histogram of a saturated still frame and the red color curve is the estimated intensity distribution of the saturated pixels.

Figure 13:
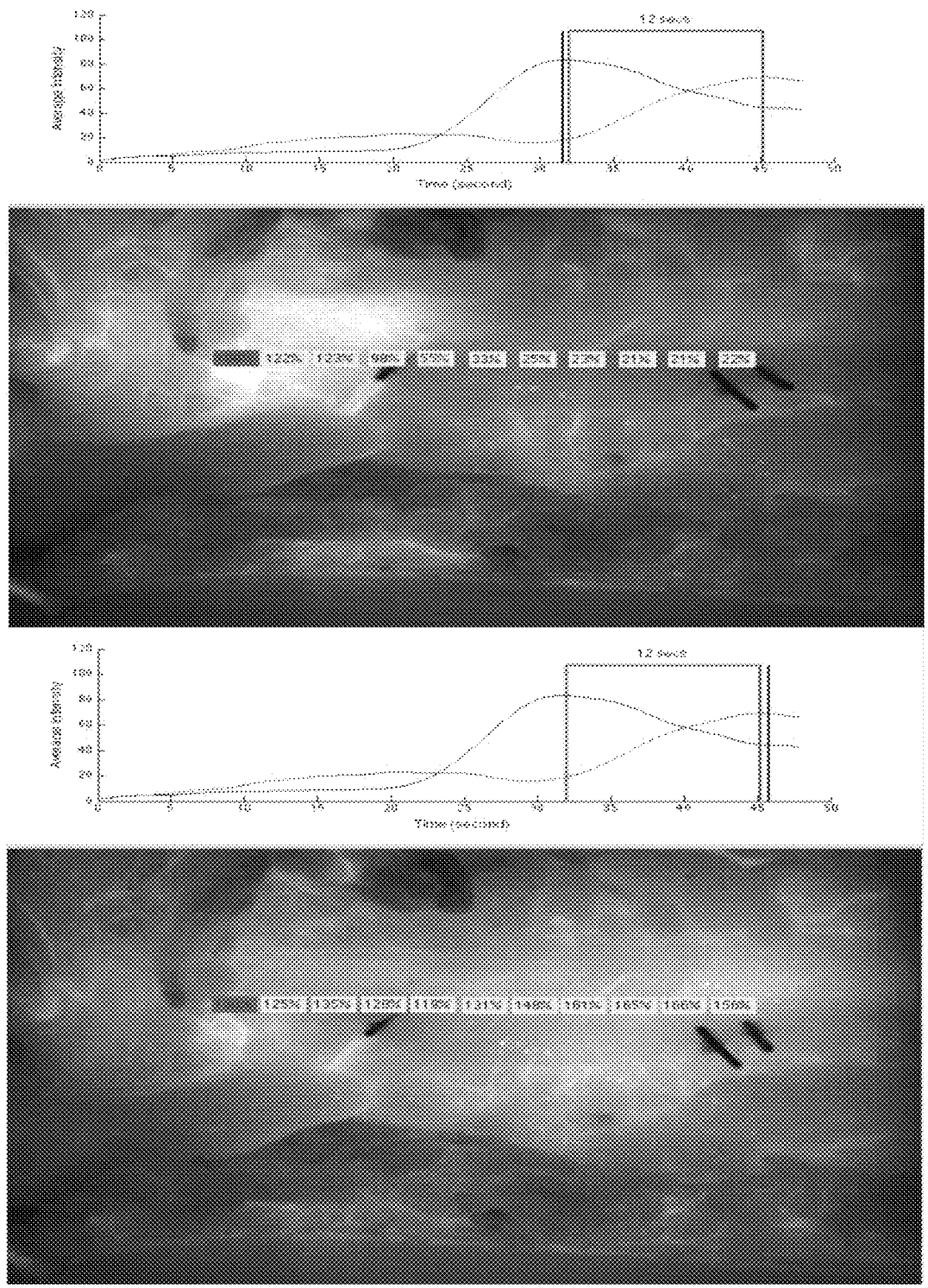
FIG. 13 is an illustration of the static vs. dynamic analytical approach, in accordance with various embodiments of the present invention.

In FIG. 13, for this example, the fluorescence progresses from left to right of this large bowel IDS. The same IDS and data are shown in both panels (note the intensity vs. time curves). The CAW is the segment of large bowel, and the CAWTs are each of the green linear points along the long axis. The blue line is the intensity vs time curve for the red reference point at the extreme left; the red line is the intensity vs time curve for the farthest right green box. The static black line (at 33 sec on the top panel, and at 41 sec on the bottom panel) represent what would be 'static snapshots' taken at these two points in this dynamic imaging an analysis process. At the 33 second mark on the top panel, the fluorescence wavefront has reached the left part of the bowel (blue curve»red curve) so the intensities of the right side the bowel are smaller compared to the left side. At the 42 second mark on the bottom panel, the fluorescence wave front has passed the left part of the bowel and reached right part (red curve»blue curve); the fluorescence intensities of the left side are now relatively smaller compared to the right side.

The same imaged segment of large bowel is analyzed to emphasize this point. The bowel segment takes 12 seconds to perfuse the left-sided CAWT reference point (red box) to the CAWT point on the far right. The blue curve is the intensity vs time curve for the left-sided CAWT, and the red curve is the right-sided CATW. In the top panel, if a static reference point is chosen (black line at 46 sec), then the red CATW is higher than the blue CATW, reflected by the normalized percentage of 156% for this point. However, on the bottom panel, if the reference point is chosen at the 32 second point, a completely different normalize result occurs, despite the fact that the same blue CATW reference was used in both analyses. The visual appearance of the dynamic image sequence is dependent upon these physiologic arteriography and perfusion characteristics, depending on which part of the tissue the fluorescent wave front will reach first.

Figure 14:
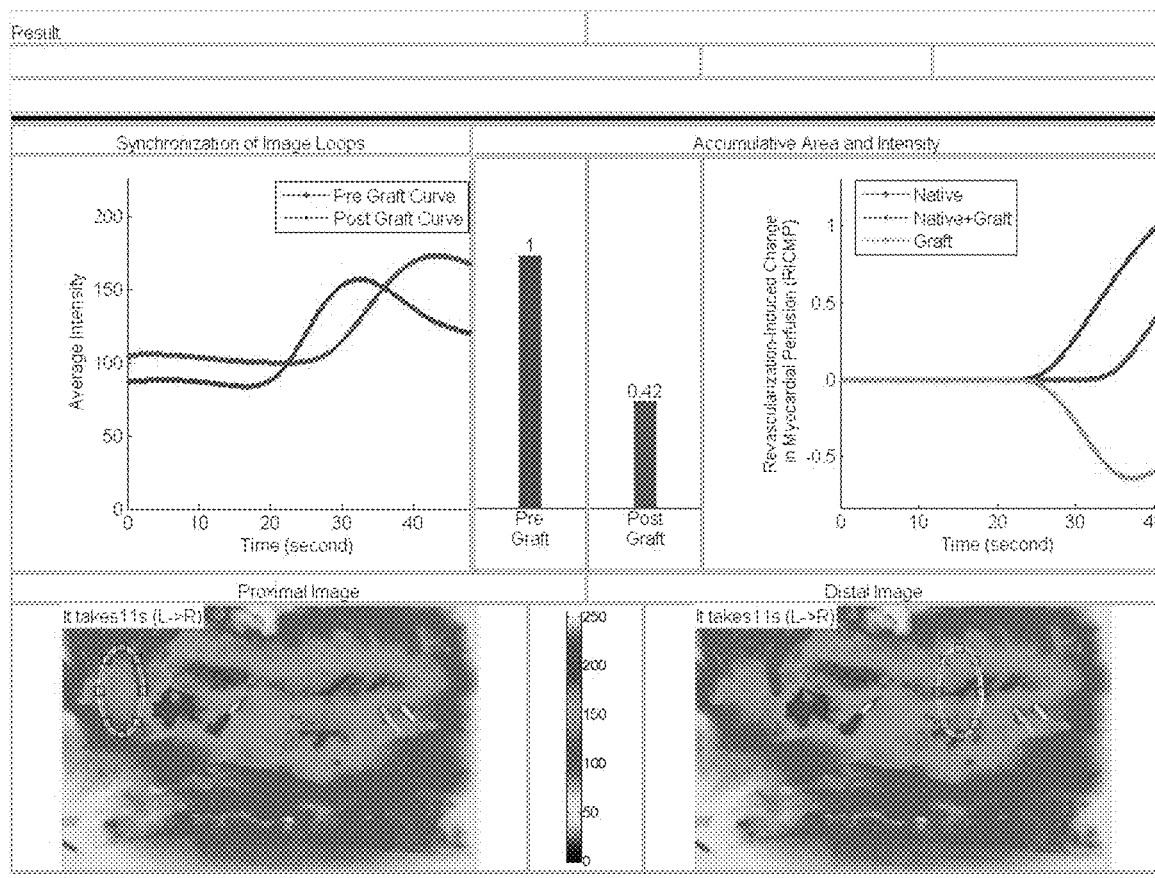
FIG. 14 illustrates a method for the formatting the comparative display of perfusion, applied to a segment of bowel pre and post operatively, in accordance with various embodiments of the present invention.

Only by synchronizing these CAWT curves by some parameter (time, distance) can the perfusion of different part of tissue can be quantified and validly compared in a dynamic manner. FIG. 14 illustrates this same principle with the analytical output from the CAPA. As shown in FIG. 14, on the upper Left are the average intensity vs. time curves; as applied to this GI large bowel evaluation, there is an 11-sec delay between the CAWC on the lower Left panel (blue oval) and the CAWC on the right panel (red oval), pre-synchronization. In this case, the fluorescence intensity of the CAWC on the right panel is less than 50% of the CAWC on the left panel, as shown by the green line in the upper right panel. This is also displayed by the relative perfusion bar data in the upper middle, where the 'post-graft' right panel of 0.42 is compared to the normalized value of 1 for the left (pre-graft) value.

Also as shown here in FIG. 14, at first glance there appears to be a substantial difference between these two CAWTs in this bowel segment, where the 'quantified perfusion' to the right (red) CATW is 0.42, compared to the normalized value of 1.0 for the left CAWT. Because this analysis result didn't include the synchronization step, however, these results are invalid. Our definition of FPA provides the basis to synchronize the ICG dye fluorescence peak in different parts of the tissue, at different times and combinations of arterial microvascular, and venous phases of angiography and perfusion, as appropriate.

Therefore, for a valid perfusion comparison, the corresponding phases have to be accurately aligned by a common parameter, whether the comparison is between different IDS s with the same CAW, or between different CAWCs within the CAW, derived from a single IDS (FIG. 7). This synchronization of phases, possible only with the recognition of the multiple phases in the FAP embodiments. Importantly, this recognition and incorporation of the FPA embodiments also greatly improves the visual display as well as the analysis.

Figure 15:
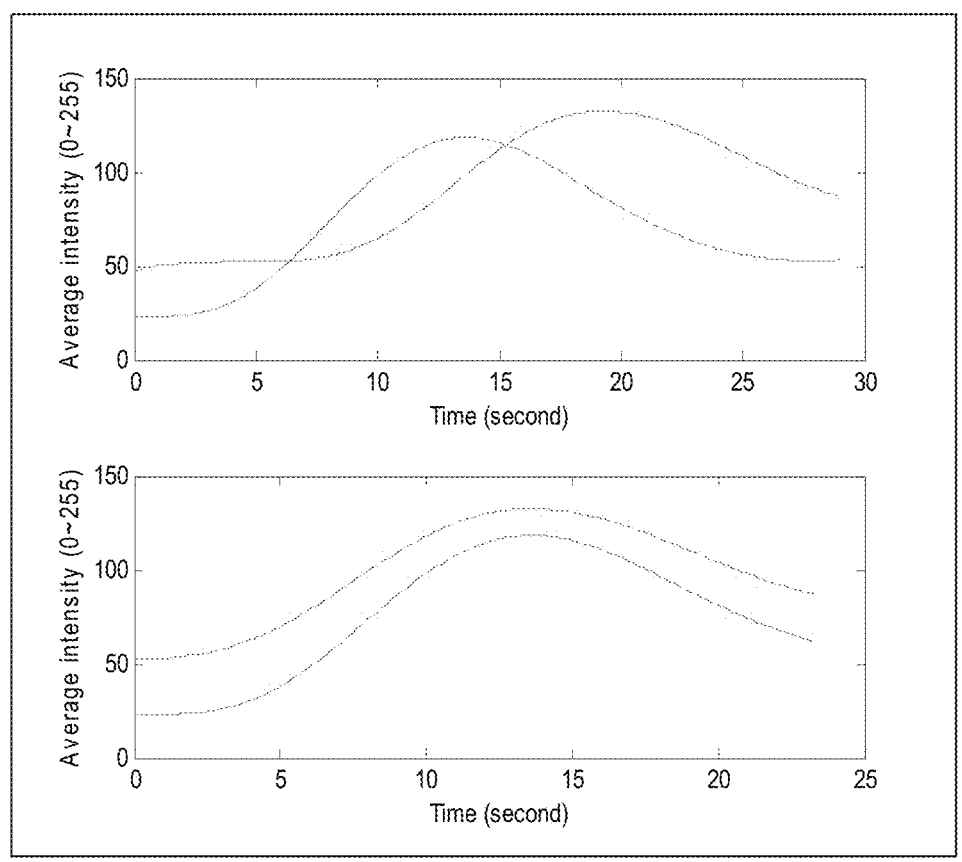
FIG. 15 is an illustration of a method for synchronization according to peak fluorescence intensity, in accordance with various embodiments of the present invention.

An illustration of a method for synchronization is shown in FIG. 15. This figure is an illustration of using the FPA cycle average intensity vs. time curves to synchronize two IDS obtained with the appropriate IDAP. The blue curve is pre-grafting, while the red curve is post-grafting. Synchronization is based on the peak fluorescence intensity for the CAW, or for each component of the CAW. Top panel: average intensity vs. time curves of Pre (blue) and post (red) IDSs before synchronization; bottom panel: average intensity vs. time curves of Pre (blue) and post (red) IDSs after synchronization.

The effect of curve synchronization impacts on both analysis and display components of CAPA. Using average intensity vs. time curves, a correlation coefficient is calculated at each alignment time position and the largest correlation coefficient yields the optimal synchronization result. The extra segments in the beginning and/or end of the IDSs will be truncated. Therefore a fundamental principle of this present invention(s) is that the intensity vs time curve is the basis for synchronization of the phases of FPA.

This venous residual creates the need to account for residual fluorescence in any type of comparative analysis. In this core analytical platform, we define the baseline as described in FIG. 6 and the present disclosure. The management solution inherent in the CAPA platform allows for accounting of the residual fluorescence when sequential injections are compared, and/or when multiple injections are used during a procedure. Moreover, this solution allows for the data capture and analysis to be performed in a time-frame that is critical for surgeons collecting image data in real time during complex surgical procedures.

During multiple ICG-NIR-FA dye injections, the residue of dye accumulates and images acquired later tend to be brighter than the previous ones, mostly due to binding in the venules.

To investigate how residue of fluorescent dye from the previous injection affects intensity of the current IDS, we performed multiple sequential, paired IDSs without any change to the tissue or position of the camera. Since these two IDSs are recorded under same physiologic and CAW conditions, by studying their average intensity vs. time curves the optimal baseline management strategy was developed.

Figure 16:
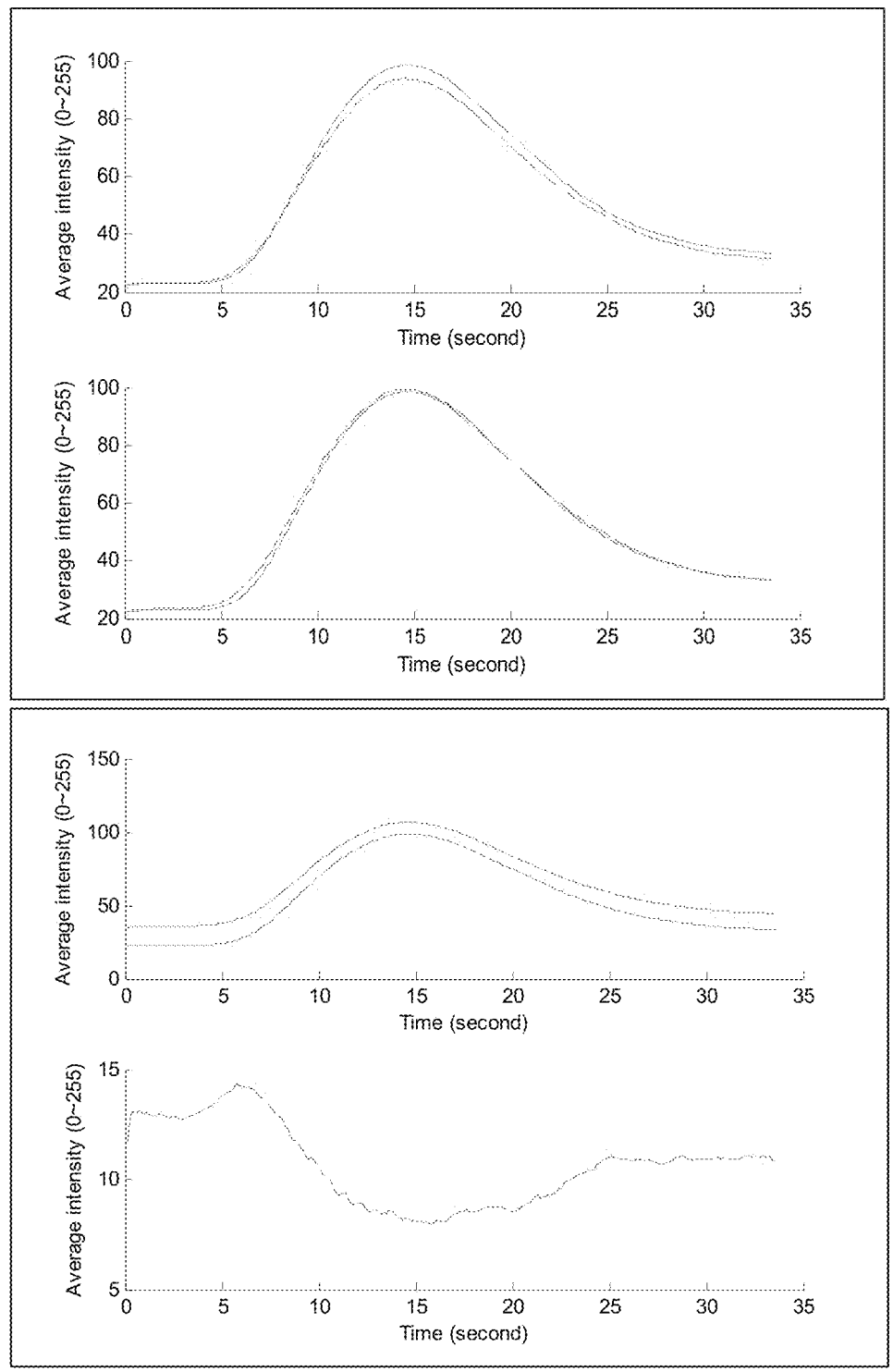
FIG. 16 illustrates a method for Fluorescence Baseline Correction, in accordance with various embodiments of the present invention.

In FIG. 16, the top panel is an illustration of average intensity vs. time curves of the pre (blue color) and post (red color) fluorescence IDSs. The bottom panel is an illustration of baseline difference between average intensity vs. time curves of the pre and post IDSs.

Importantly, from FIG. 16 we can tell that baseline difference between two CAWS/CAWTs is not constant across the IDS acquisition window. As the FPA average intensity vs. time curve is increasing and approaching the peak intensity, the baseline difference keeps decreasing. Based on these observations, we use Equation 7 to estimate the change of the baseline fluorescence intensity difference over the IDS time:

$$BD(x, y, t) = C(x, y) \times \frac{\sqrt{AIC_{post}(0)}}{\sqrt{AIC_{post}(t)}} \quad \text{Equation 7}$$

Where BD is the baseline difference between pre and post IDSs with x, y as pixel coordinates and t as time; C(x, y) is the constant background difference between pre and post images estimated from the first few seconds of the IDSs; $AIC_{post}(t)$ is the average intensity curve of the post image acquisition and $$\frac{\sqrt{AIC_{post}(0)}}{\sqrt{AIC_{post}(t)}}$$

is used to adjust the baseline difference across time. From FIG. 16 we can tell that treating vArcp$_{os}$at) the baseline line difference as a constant will lead to "over subtraction" causing loss of useful signal from the post image acquisition sequence.

Examples of two important novel paradigms are documented herein. These are 1) the ability to recognize and document arterial-phase competitive flow between native and grafted sources of blood flow under physiologic conditions, and 2) the ability to recognize microvascular-phase collateral flow in adjacent and/or related areas of perfused tissues.

Figure 17:
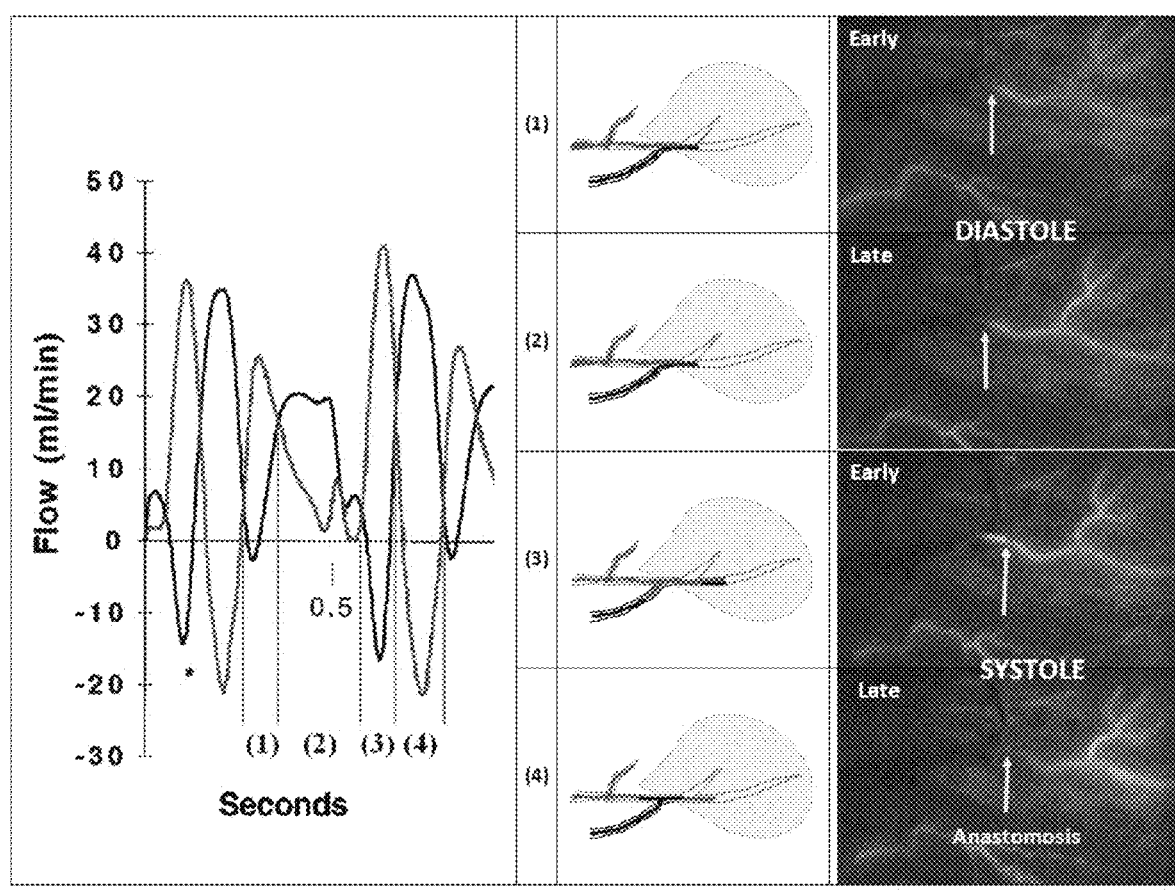
FIG. 17 is an illustration of one type of Complex Angiography Analysis, namely, competitive flow, in accordance with various embodiments of the present invention.

In FIG. 17, visual documentation of competitive flow between a native epicardial coronary artery and a patent bypass graft to that artery, beyond what was thought to be a flow-limiting stenosis is presented. The physiology-based and dynamic analysis using the FPA embodiment makes the documentation of competitive and potentially-significant competitive flow identification at CABG a reality for the first time.

Competitive flow is currently most appropriately understood in the context of the arterial phase of FPA, although extension into the microvascular phase is being examined. FIG. 17 shows documentation of competitive flow in man in real time at CABG. This figure clearly illustrates the reversal of flow between the native coronary and the widely patent bypass graft in early and late systole that is diagnostic of competitive flow. In these sequential frames from the IDS separated by 24 sec intervals, there is washout of the ICG+ blood in the native coronary by the blood without ICG from the graft; the competition also causes the ICG+ blood to reflux back across the anastomosis into the distal end of the bypass graft. This is new and very important information to now have available in real time, at the setting of surgical revascularization.

Figure 18:
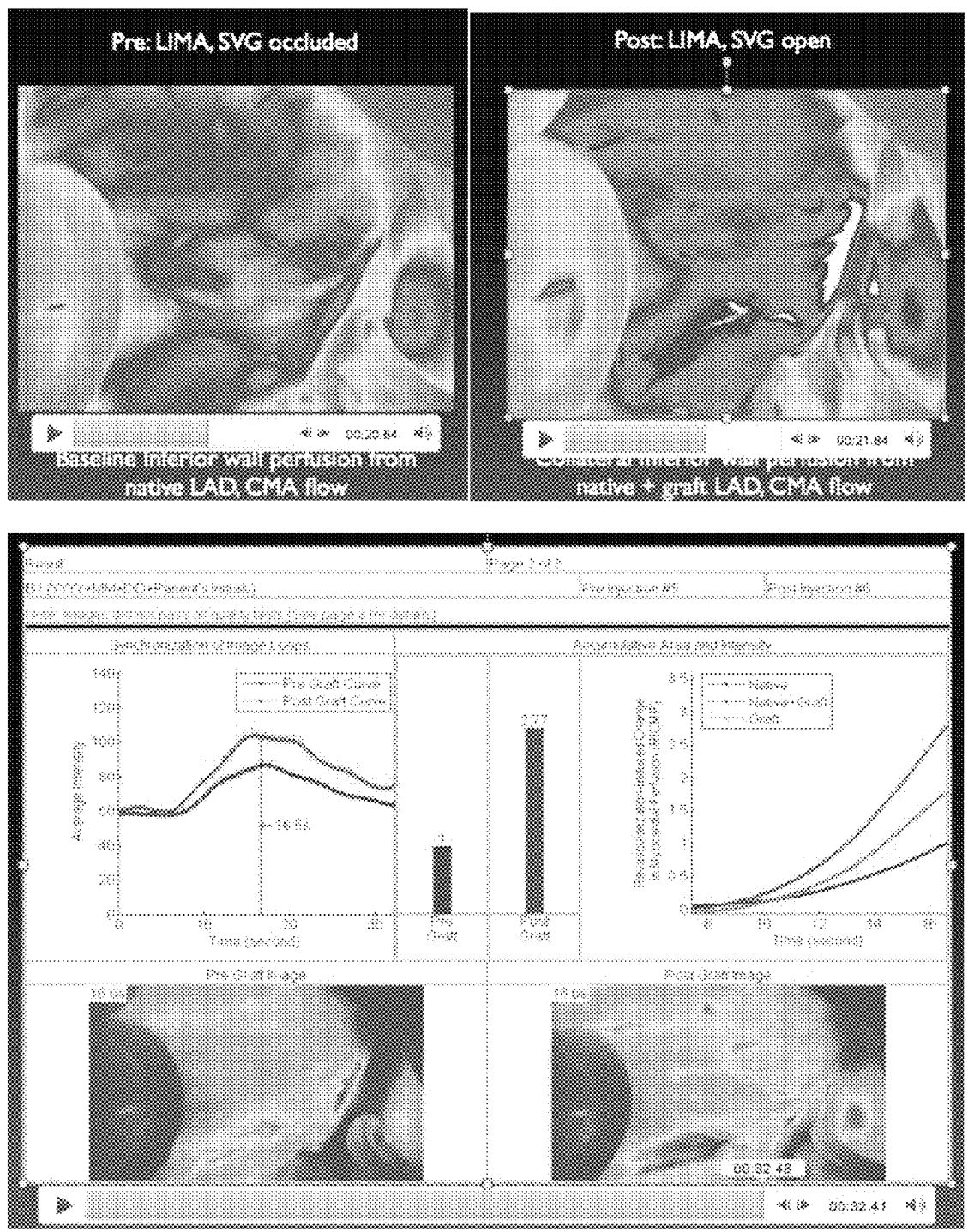
FIG. 18 illustrates another type of Complex Angiography Analysis, namely collateral flow, in accordance with various embodiments of the present invention.

In, FIG. 18 visual documentation and quantification of the effect of collateral flow in the heart as a result of bypass grafts and increases in perfusion to territories supplying the collateral flow, is presented. The top panel shows the comparison of the two, sequential IDS s, pre-grafting (left) and post-grafting (right). The bottom panel is the quantification display (see FIG. 21A for full explanation of the display). Note, in this case there was a 2.5-fold increase in the inferior wall of the heart as a result of bypass grafts placed to the anterior and lateral walls. The ability to use ICG-NIR-FA to capture and then to analyze these images to document in real-time this collateral flow is dependent upon the FPA embodiment.

Collateral flow is currently most appropriately understood in the context of the microvascular phase of FPA. Again the cardiac application is used as an example, in part because the heart is typically able to develop collaterals with non-acute, regional occlusions of the blood supply to a territory of the heart. FIG. 18 shows collateral flow imaged in real time in man at CABG. The top panel shows the same CAW from two sequential IDSs; the CAW is imaging the inferior wall of the heart, before and after placing bypass grafts to the anterior and lateral walls of the heart. The left panel images the native coronary perfusion to the inferior wall (with the grafts temporarily occluded), while the right panel images the inferior wall, with the grafts to the anterior and lateral walls open and perfusing their respective territories. Visually, there is a substantial increase in fluorescence and hence perfusion to this inferior wall as a result of these bypass grafts; this increase in perfusion comes from collateral flow from the anterior and lateral territories to the inferior territory in this patient's heart. The bottom panel shows the CAPA platform analysis and quantification of the perfusion difference before and after bypass grafting. There was a 2.5-fold increase in perfusion to the inferior wall as a result of this collateral perfusion increase. This is new and very important information to have available in real time, at the setting of surgical revascularization.

The CAPA perfusion quantification is a relative measurement based on a comparison, as illustrated in FIG. 7 and FIG. 8. To increase the sensitivity of the analysis results, only pixels with intensity above certain value are used to estimate relative perfusion. The still frame located at the peak of the average intensity vs. time curve in one IDS is used to determine this threshold by $$k = \text{mean}(I_{max}) + m \times \text{std}(I_{max}) \quad \text{Equation 8}$$

Where '$_{max}$ is the still frame that has the maximum average intensity in one IDS; mean is the average function; std is the standard deviation function; m is a constant parameter between 0-1 to adjust this Equation 8. The threshold k is used in one or several IDSs depending on the application and only pixels with intensity above the value are used in the perfusion calculation. The arterial phase of IDS records perfusion as a process of blood being delivered by arteries to the tissue. Correspondingly, this process starts from the beginning (baseline part) to the peak (maximum) of the average intensity vs. time curve. Visually, this process includes arterial and part of micro vascular phases in the IDS. We are assuming not only the Verfusion strength" (corresponds to the average intensity above the threshold) but also the Verfusion area" (corresponds to the number of the pixels with intensity above the threshold) should be included in estimation of the perfusion level. Equation 9 is applied in all the still frames of the IDSs till the maximum of the average intensity curve is reached.

$$A1(t) = \text{Num}(I(x,y,t) > k) \times \text{mean}(I(x,y,t) > k) \quad \text{Equation 9}$$

Where A1 is a number representing combination of perfusion strength and area at time t. 1(x, y, t) is a still frame at one time location of an IDS; Num is the function to calculate the number of pixels; mean is the average function.

Then we estimate the accumulation effect of the A1 (t) from the beginning (baseline part) to the peak (maximum) of the average intensity vs. time curve as $$A1(T) = \sum_0^T [A1(t) - A1(0)] \quad \text{Equation 10}$$

Where T is any time at the peak (maximum); A1 (0) is the residue from baseline. In the cardiac application we calculate this area-intensity value in sequential IDSs of the same CAW tissue area. In other CAAs identified thus far, we calculate this area-intensity value relatively across two or more CAWTs identified in one CAW identified in one IDS. Notice that this is a relative value in both cases, and it does not reflect the estimation of perfusion directly. In the cardiac application, to estimate the perfusion change, we normalized the post area-intensity value by the pre one by $$A1 = \frac{A1(T)_{post}}{A1(T)_{pre}} \quad \text{Equation 11}$$

In the other CAAs identified thus far, to estimate the perfusion change, we normalize the current CAWT by the reference CAWT $$A1 = \frac{A1(T)_{CAWT-current}}{A1(T)_{CAWT-ref}} \quad \text{Equation 12}$$

The opportunity inherent in FPA and CAPA extends to image and image analysis display. The NIR part of the spectrum is outside the visible color spectrum, and therefore is inherently a black and white, 255-level grey scale image. This is actually quite sufficient for imaging the arterial phase of full phase imaging, but is not optimal or optimized for microvascular or venous phase imaging. We have developed different color schemes to optimize the display for combined (arteriography and perfusion) display using a modified RGB format, and for the microvascular (perfusion) image display and analysis. This in turn means that in many CAAs combination of displays of the same NIR image data is optimal for understanding the context and content of the image(s) and analyses for decision-making.

Figure 19:
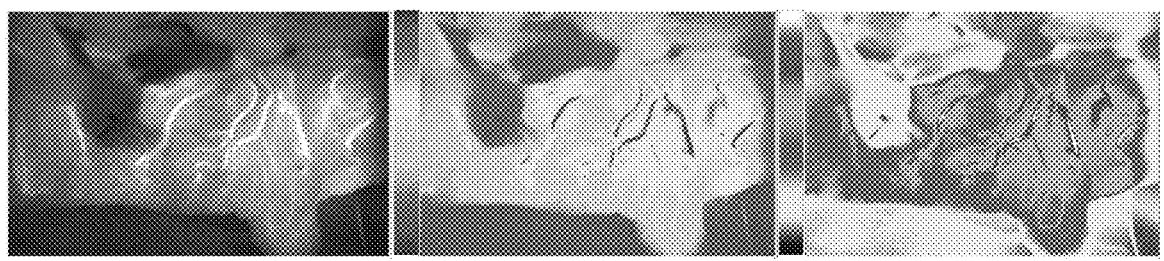
FIG. 19 is an illustration that compares perfusion visualization with the NIR B & W (left), a standard RGB (middle), and the perfusion visualization scheme (right) used as part of the CAPA core analysis platform, in accordance with various embodiments of the present invention.
Figure 19:
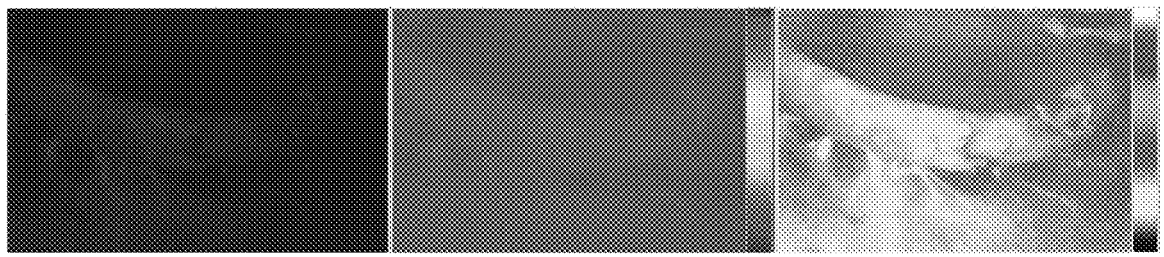

As illustrated in FIG. 19, our experience has demonstrated that the NIR is more optimized for angiography, the RGB presentation is more optimized for BOTH angiography and perfusion, and the BI-YR-G-B-W display is optimized for perfusion. On the top panel is shown a segment of large colon. On the bottom panel is shown is a segment of stomach used to create a neo-esophagus in the esophageal application (same as FIG. 4).

FIG. 19 also shows the comparison of these three displays. It is important to understand that these displays all render the same image metadata; the NIR B & W is the 'raw' NIR presentation; the same image data are simply colorized according to the different 0-255 scales, optimized for combined (arterial and perfusion) and microvascular (perfusion) presentation and display. Specifically the perfusion display range is black, yellow, orange, red, green, blue and white for intensity of fluorescence ranging from 0-255. Comparably, the NIR grey scale and other RGB-based ranges are too narrow between the low and high intensities that they are not visually sensitive enough to reflect the subtle but important perfusion changes.

Figure 20:
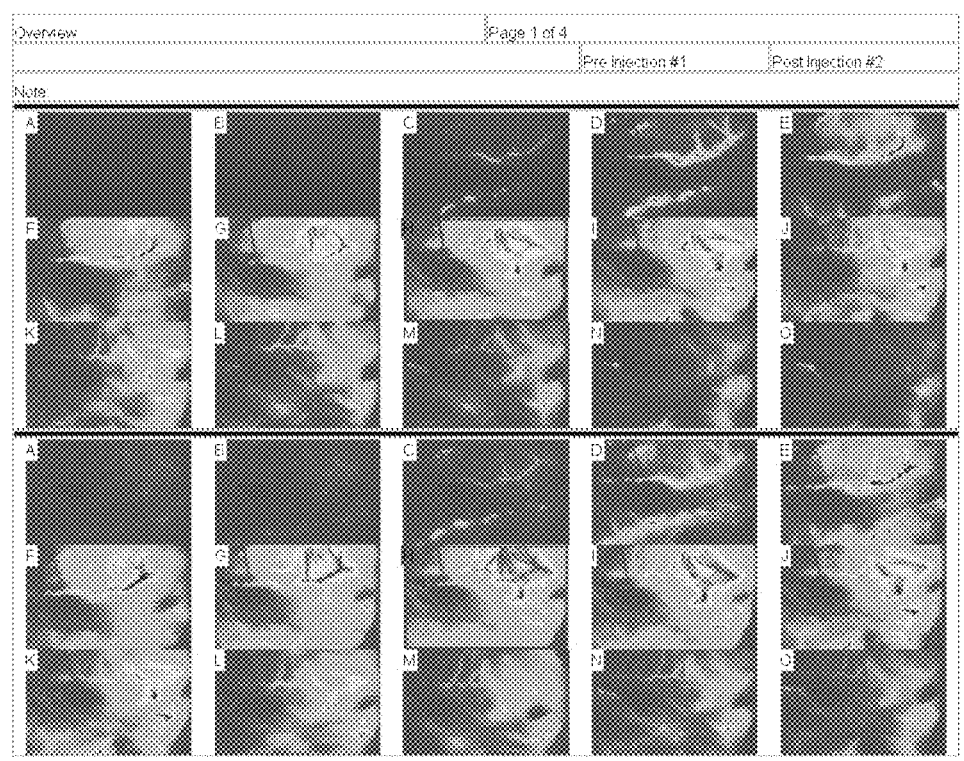
FIG. 20 illustrates the Overview Display as used in the cardiac application, in accordance with various embodiments of the present invention.

We also designed an Overview Display as a unique way to visualize the IDS+FPA data. In FIG. 20, this Overview Display compares pre-grafting perfusion with post-grafting perfusion, after synchronization of the two IDSs. Panel H in each sequence again reflects the peak average intensity in the two CAWS, which by design and by the Image Data Acquisition Protocol (focusing on both Angiography and Perfusion) used in cardiac, image the same area on the anterior perfusion territory of the heart. In this case, an internal mammary artery was grafted to the left anterior descending coronary artery. Note the obvious increase in fluorescence intensity in the panel H post-grafting (bottom) compared to pre-grafting (panel H, top). The quantified difference in fluorescence intensity is directly proportional to the difference in myocardial perfusion.

However, as previously articulated, to visually capture the inference of the FPA and CAPA construct requires that two points can be accurately compared. As depicted in FIG. 13 and FIG. 14, (colon), however, we CANNOT use time alone to establish this comparison. Therefore this Overview Display uses the same IDS synchronization described above to accurately provide this intuitive visual comparison. The frame in the red box (labeled H) represents the peak intensity on the average intensity vs. time curve, which corresponds to the micro vascular phase. The frames before it (labeled from A to G) are the baseline and arterial phase and the frames after it are the venous phase and the fluorescent dye residue; each frame is separated by 1.5 sec from the peak, in either direction. This display is physiologically organized, and because of the synchronization technique is possible to reliably make visual comparisons to accompany the CAPA platform analyses. This same principle is used in the analysis display.

FIG. 21, panels A-D, show the display format as applied to the cardiac CAA. There are four components to the analysis presentation. Panel A comes up first, and is the Overview Display discussed above. Panel B is the Quantified result display.

In FIG. 21, Panel A is the Overview Display of the synchronized IDSs in standard color display (both angiography and perfusion). The pre images are in the upper panel and post images are in the lower one (see synchronization section for details). Compare the fluorescence intensity in the panels labeled H, top vs. bottom. There is visually much more fluorescence intensity post-grafting than pre-grafting to the perfused territory supplied by this grafted vessel on the anterior wall of the heart.

FIG. 21, Panel B, includes all the analysis results. In the upper left hand corner are displayed the synchronized average intensity vs. time curves with time line indicating the peaks. The left and right bottom panels correspond to the colorized pre- and post-images at the peak of the curves with time labels on the upper left hand corners. Note these time labels are identical, indicating the time synchronization between the pre- and post-images is based on peak intensity, even though the image sequences are not synchronized based on the cardiac cycle. The two bars on the upper panel are calculated from the accumulated area and intensity curves. The pre-graft perfusion status is represented by the blue colored bar, which is always normalized to one for comparison to the post graft perfusion status, represented by the red color bar. To better illustrate the quantification of change in perfusion over time, and to illustrate the contribution of the bypass graft, the perfusion changes over time are generalized in the chart at the upper right hand corner with blue, red and green color curves representing the accumulated perfusion changes over time caused by native, native plus graft and bypass graft respectively. Also shown in Panel B is the final quantification result at 13.4 sec, which is the time point of peak fluorescence. Finally, the pre-graft perfusion level is normalized to 1, for comparison to the post-graft perfusion (in this case, 1.28) in a bar chart format.

FIG. 21, Panel C is the Quality Report for the data and analysis. This includes all the quality criteria that each IDS is subjected to in order to further support and validate the CAPA results. If there is an IDS quality issue, the error warning message displays on this page and on Page B as well, to avoid misinterpretation of the results.

FIG. 21, Panel D provides Explanation data, including Error Warning feedback on the Data Quality check.

An additional opportunity inherent in the FPA and CAPA invention is to analyze angiography and perfusion as a dynamic process, rather than assuming that a selected static image accurately represents these physiologic processes. In some CAAs, multiple CAWS (for example, bypass grafts to the anterior, lateral and inferior territories of the heart) can be captured and analyzed individually; following this, the CAPA analysis metadata can be combined into 2-D and 3-D reconstructions to more accurately display the physiologic effects of perfusion increases or decreases, reperfusion, and/or devascularization.

The importance of this component of the present invention is in the ability to modify the CAPA core analysis display capabilities to specifically represent the critical information display that is necessary to optimize real-time decision-making by the surgeons in the operating room. The display results must be entirely accurate, intuitively presented, and simple enough to be grasped and understood in a visual display format from across the operating room.

Figure 22:
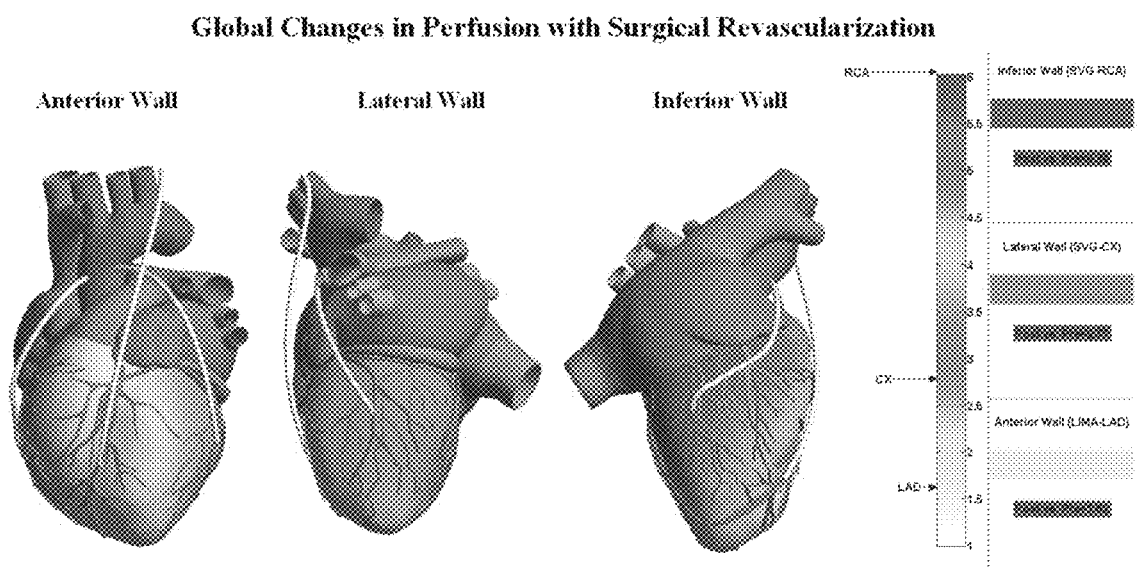
FIG. 22 illustrates one application of the cumulative and additive presentation capabilities of the CAPA analysis and display in accordance with various embodiments of the present invention.

As an example of this display capability, we can use the cardiac application of the 3-D model for revascularization-induced change in myocardial perfusion (FIG. 22). We typically measure the perfusion change in anterior, lateral and inferior territories of the heart after a 3-vessel CABG procedure. We can map the perfusion change onto each specific territory of the 3D heart model, along with the corresponding grafts. This creates a complete physiologic picture (combined anatomic and functional changes as a result of CABG), illustrating the global change in myocardial perfusion that results from the illustrated grafts after CABG. We use colorization to represent the results of perfusion analysis in each different territory, derived from the individual perfusion analyses obtained on a per-graft basis. In our methodology, we can visualize anatomy (3D structure of the heart and grafts) and physiology (perfusion change in each different area of the heart in color representation) at the same time.

As an image analysis platform, it is necessary to be able to assess the quality of the IDSs for subsequent analysis. This is part of the analytical platform, and consists of the IDS Image Quality Test (FIG. 8) As discussed, the validity of the perfusion analysis depend on if IDAP criteria has been met. Practically, in clinical setting sometimes a case failed the IDAP standard might go unnoticed and the following invalid analysis result could be confusing and misleading. To prevent this, quality of IDS is examined before the final report is generated. The following components of the Image Data Quality are automatically tested:

Baseline Test
  a. Check if baseline is smooth enough.
  b. In cardiac application, baseline of post graft image should be larger than the one of pre graft image.
Timing test
  c. If image acquisition starts too late thus arterial phase gets truncated.
  d. If image acquisition ends too early thus venous phase gets truncated.
Brightness test
  e. Check if image is too dark.
  f. Check if image gets saturated.
IDS overall quality test
  g. Check the shape and smoothness of the average intensity over time curve. The quality of the curve could be potentially compromised by external factors such as fluorescence from the lung or contamination from the headlight.

The foregoing is illustrative of the present invention and is not to be construed as limiting thereof. Although a few exemplary embodiments of the present invention have been described, those skilled in the art will readily appreciate that many modifications are possible in the exemplary embodiments without materially departing from the novel teachings and advantages of this invention. Accordingly, all such modifications are intended to be included within the scope of the invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method for visualizing blood flow in tissue before and after a surgical intervention, the method comprising:
   receiving a first image data sequence comprising a plurality of fluorescence images of the tissue before the surgical intervention, wherein the first image data sequence encompasses at least one full phase angiography cycle of blood flow through the tissue;
   receiving a second image data sequence comprising a plurality of fluorescence images of the tissue after the surgical intervention, wherein the second image data sequence encompasses at least one full phase angiography cycle of blood flow through the tissue;
   synchronizing the first and second image data sequences based on peak fluorescence intensities of average intensity vs. time curves of the first and second image data sequences to align at least a portion of the full phase angiography cycle of the first image data sequence with the corresponding portion of the full angiography cycle of the second image data sequence;
   determining, in real time, an amount of perfusion change in the tissue based on the synchronized image data sequences; and
   displaying, in real time, the synchronized image data sequences and the determined amount of perfusion change on a display.

2. The method of claim 1, wherein the tissue is a blood vessel, and the blood vessel is a coronary artery bypass graft.

3. The method of claim 1, wherein the tissue is selected from the group consisting of myocardium during revascularization, breast tissue during reconstruction and bowel tissue during anastomosis.

4. The method of claim 1, wherein the full phase angiography cycle of blood flow comprises an arterial phase, a microvascular phase, and a venous phase.

5. The method of claim 4, wherein synchronizing the first and second image data sequences comprises correlating, between the first and second image data sequences, at least one of the arterial phase, microvascular phase, and venous phase.

6. The method of claim 1, wherein synchronizing the first and second image data sequences comprises calculating a correlation coefficient at each alignment time position and synchronizing the first and second image data based on the largest correlation coefficient.

7. The method of claim 1, wherein determining, in real time, an amount of perfusion change in the tissue based on the synchronized image data sequences comprises comparing relative fluorescence intensity between the synchronized first and second image data sequences.

8. The method of claim 1, wherein determining, in real time, an amount of perfusion change in the tissue based on the synchronized image data sequences comprises estimating a change of baseline fluorescence intensity difference over the synchronized image data sequences, and adjusting the synchronized image data sequences based on the change in baseline fluorescence intensity.

9. The method of claim 1, wherein determining, in real time, an amount of perfusion change in the tissue based on the synchronized image data sequences comprises estimating the perfusion level based on average fluorescence intensity above a threshold.

10. The method of claim 9, wherein determining, in real time, an amount of perfusion change in the tissue based on the synchronized image data sequences further comprises estimating the number of image pixels having fluorescence intensity above the threshold.

11. A system for visualizing blood flow in tissue before and after a surgical intervention, comprising:
    a processor that:
       receives a first image data sequence comprising a plurality of fluorescence images of the tissue before the surgical intervention, wherein the first image data sequence encompasses at least one full phase angiography cycle of blood flow through the tissue;
       receives a second image data sequence comprising a plurality of fluorescence images of the tissue after the surgical intervention, wherein the second image data sequence encompasses at least one full phase angiography cycle of blood flow through the tissue;
       synchronizes the first and second image data sequences based on peak fluorescence intensities of average intensity vs. time curves of the first and second image data sequences to align at least a portion of the full phase angiography cycle of the first image data sequence with the corresponding portion of the full phase angiography cycle of the second image data sequence; and
       determines, in real time, an amount of perfusion change in the tissue based on the synchronized image data sequences; and
    a display for displaying, in real time, the synchronized image data sequences and the determined amount of perfusion change.

12. The system of claim 11, wherein the full angiography cycle of blood flow comprises an arterial phase, a microvascular phase, and a venous phase, and the processor synchronizes the first and second image data sequences by correlating, between the first and second image data sequences, at least one of the arterial phase, microvascular phase, and venous phase.

13. The system of claim 11, wherein the processor synchronizes the first and second image data sequences by calculating a correlation coefficient at each alignment time position and synchronizing the first and second image data based on the largest correlation coefficient.

14. The system of claim 11, wherein the tissue is a blood vessel and the processor determines, in real time, an amount of perfusion change in the tissue based on the synchronized image data sequences before and after the surgical intervention by comparing relative fluorescence intensity between the synchronized first and second image data sequences.

15. The system of claim 11, wherein the processor determines, in real time, an amount of perfusion change in the tissue based on the synchronized image data sequences before and after the surgical intervention at least in part by estimating the perfusion level based on average fluorescence intensity above a threshold.

16. The system of claim 15, wherein the processor determines, in real time, an amount of perfusion change in the tissue based on the synchronized image data sequences at least in part by estimating the number of image pixels having fluorescence intensity above the threshold.

\* \* \* \* \*